US008114660B2

(12) United States Patent
Pawliszyn

(10) Patent No.: US 8,114,660 B2
(45) Date of Patent: *Feb. 14, 2012

(54) CALIBRATION PROCEDURES AND DEVICES FOR INVESTIGATION BIOLOGICAL SYSTEMS

(76) Inventor: Janusz B. Pawliszyn, Waterloo (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/938,876

(22) Filed: Nov. 3, 2010

(65) Prior Publication Data

US 2011/0104027 A1  May 5, 2011

Related U.S. Application Data

(60) Division of application No. 11/706,167, filed on Feb. 15, 2007, now Pat. No. 8,008,064, which is a continuation of application No. 11/208,933, filed on Aug. 23, 2005, now Pat. No. 7,232,689, and a continuation-in-part of application No. 10/506,827, filed as application No. PCT/CA03/00311 on Mar. 6, 2003, now Pat. No. 7,384,794, said application No. 11/208,933 is a continuation-in-part of application No. 10/506,827.

(60) Provisional application No. 60/604,631, filed on Aug. 27, 2004, provisional application No. 60/421,001, filed on Oct. 25, 2002, provisional application No. 60/421,510, filed on Oct. 28, 2002, provisional application No. 60/427,833, filed on Nov. 21, 2002, provisional application No. 60/364,214, filed on Mar. 11, 2002, provisional application No. 60/393,309, filed on Jul. 3, 2002.

(51) Int. Cl.
C12M 1/34 (2006.01)

(52) U.S. Cl. .................................. 435/287.1

(58) Field of Classification Search .................. None
See application file for complete search history.

(56) References Cited

U.S. PATENT DOCUMENTS

| 4,476,231 | A | | 10/1984 | Deindoerfer et al. |
| 4,616,652 | A | | 10/1986 | Simpson |
| 5,047,437 | A | | 9/1991 | Cooke et al. |
| 5,120,510 | A | | 6/1992 | Gourley et al. |
| 5,424,187 | A | | 6/1995 | Shor et al. |
| 5,460,813 | A | | 10/1995 | Leung et al. |
| 5,464,395 | A | | 11/1995 | Faxon et al. |
| 5,479,923 | A | | 1/1996 | Rantala |
| 5,640,470 | A | | 6/1997 | Iyer et al. |
| 5,691,206 | A | * | 11/1997 | Pawliszyn ............... 436/178 |
| 5,693,228 | A | | 12/1997 | Koehler et al. |
| 6,287,521 | B1 | | 9/2001 | Quay et al. |
| 6,360,588 | B1 | | 3/2002 | Ross et al. |
| 6,558,958 | B1 | | 5/2003 | Pilevar et al. |
| 6,689,603 | B2 | | 2/2004 | Pompidou et al. |
| 6,730,096 | B2 | | 5/2004 | Basta |
| 6,743,180 | B1 | | 6/2004 | Van Bockel |
| 6,808,937 | B2 | * | 10/2004 | Ligler et al. ............ 436/518 |
| 6,871,556 | B2 | * | 3/2005 | Andresen et al. ........ 73/863.21 |
| 7,232,689 | B2 | * | 6/2007 | Pawliszyn ............... 436/178 |
| 7,259,019 | B2 | * | 8/2007 | Pawliszyn et al. ....... 436/178 |
| 7,384,794 | B2 | * | 6/2008 | Pawliszyn ............... 436/178 |
| 7,468,281 | B2 | * | 12/2008 | Kallury et al. ........... 436/178 |
| 7,605,003 | B2 | | 10/2009 | Chan et al. |
| 2002/0034827 | A1 | | 3/2002 | Singh et al. |
| 2003/0135195 | A1 | | 7/2003 | Jimenez et al. |
| 2003/0180954 | A1 | | 9/2003 | Riviere et al. |
| 2003/0183758 | A1 | | 10/2003 | Colburn et al. |
| 2004/0005582 | A1 | | 1/2004 | Shipwash |
| 2004/0171169 | A1 | | 9/2004 | Kallury et al. |
| 2005/0032237 | A1 | | 2/2005 | Sandra et al. |
| 2005/0142033 | A1 | | 6/2005 | Glezer et al. |

FOREIGN PATENT DOCUMENTS

| DE | 19905239 | 8/2000 |
| JP | 1164277 | 3/1999 |
| WO | 9115745 | 10/1991 |
| WO | 0068665 | 11/2000 |

OTHER PUBLICATIONS

Moneti et al., "Solid-Phase Microextraction of Insect Epicuticular Hydrocarbons for Gas Chromatographic/Mass Spectrometric Analysis", Rapid Communications in a Mass Spectrometry, vol. 2, 1997, pp. 857-862.
Frerot et al., "Solid-Phase Microextraction (SPME): A New Tool in Pheromone Identification in Lepidoptera", Journal of High Resolution Chromatography, Jun. 1997, vol. 20, Issue 6, pp. 340-342.
Smith et al., "Solid-Phase Microextraction as a Tool for Studying Volatile Compounds in Frog Skin", Chemistry and Ecology, 2000, vol. 17, Issue 3, pp. 215-225.
Heinze, "Ultramicroelectrodes in Electrochemistry", Angewandte Chemie International Edition in English, Sep. 1993, vol. 32, Issue 9, pp. 1268-1288.
Whang et al., "Solid Phase microextraction coupled to capillary electrophoresis", Anal. Commun., 1998, vol. 35, pp. 353-356.
Jackson et al., "Mass spectrometry for genotyping: an emergoing tool for molecular medicine", Molecular Medicine Today, Jul. 1, 2000, vol. 6, Issue 7, pp. 271-276.
Namera et al., "Analysis of anatoxin-a in aqueous samples by solid-phase microextraction coupled to high performance liquid chromatography with fluorescence detection and on-fiber derivatization", Journal of Chromatography A, 2002, vol. 963, pp. 295-302.
Lavaud et al., "Optimal anticoagulation strategy in haemodialysis with heparin-coated polyacrylonitrile membrane", Oxford Journals, Medicine, Nephrology Dialysis Transplantation, 2003, vol. 18, Issue 10, pp. 2097-2104.
Lord et al., "Development and Evaluation of a Solid-Phase Microextraction Probe for in Vivo Pharmacokinetic Studies", Analytical Chemistry, Oct. 1, 2003, vol. 75, No. 19, pp. 5103-5115.
Nie et al., "Preparation and characterization of polyacrylonitrile-based membranes: Effects of internal coagulant on poly(acrylonitrile-co-maleic acid) ultrafiltration hollow fiber membranes", Desalination, Jan. 5, 2004, vol. 160, Issue 1, pp. 43-50.

(Continued)

Primary Examiner — Ann Lam
(74) Attorney, Agent, or Firm — David A. Nauman; Borden Ladner Gervais LLP

(57) ABSTRACT

Use of calibrant in extraction phase is described for quantification of components of interest in samples in laboratory application as well as in on-site monitoring. This approach is particularly useful for in-vivo investigation of living system.

3 Claims, 42 Drawing Sheets

OTHER PUBLICATIONS

Yang et al., "Surface Modification and Blood Compatibility of Polyacrylonitrile Membrane with Immobilized Chitosan-Heparin Conjugate", Journal of Polymer Research, Sep. 3, 2002, vol. 9, No. 3, pp. 201-206.

Zhang et al., "Solid-phase microextraction integrates sampling, extraction, concentration, and sample introduction into a single step", Analytical Chemistry, Sep. 1, 1994, vol. 66, No. 17, pp. 844-852.

Mullett et al., "Direct Determination of Benzodiazepines in Biological Fluids by Restricted-Access Solid-Phase Microextraction", Analytical Chemistry, vol. 74, No. 5, Mar. 1, 2002, pp. 1081-1087.

Musteata et al., "Biocompatible Solid-Phase Microextraction Coatings Based on Polyacrylonitrile and Solid-Phase Extraction Phases", Analytical Chemistry, vol. 79, No. 18, Sep. 15, 2007, pp. 6903-6911.

Boos et al., "Alkyl-Diol Silica (ADS): restricted access precolumn packings for direct injection and coupled-column chromatography of biofluids", Fresenius J Analytical Chemistry, Apr. 1995, vol. 352, pp. 684-690.

* cited by examiner

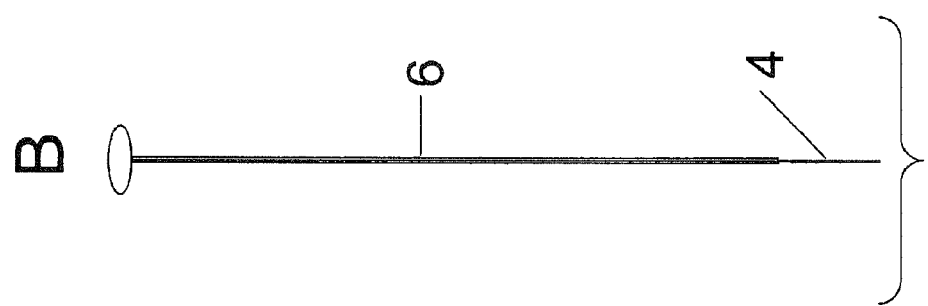
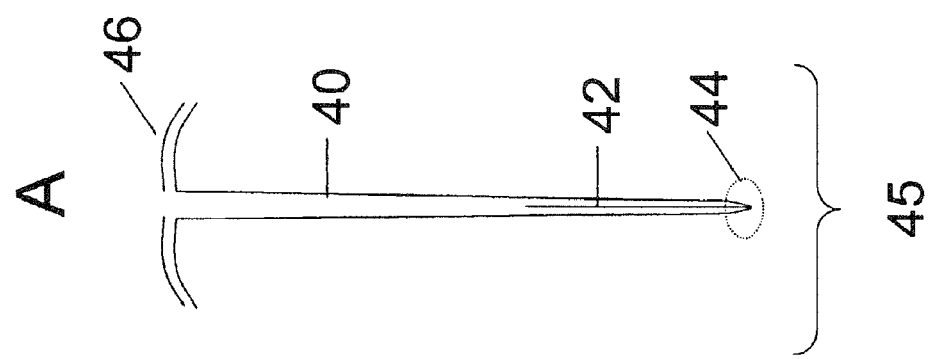
Figure 5

(×) Absorption of toluene (component);
(○) Desorption of deuterated (*d*-8) toluene (calibrant);
(▲) Sum of the component and calibrant Predicted vs. experimental uptake of fluorene with calibrant: (◇) benzene; (□) toluene; (△) ethylbenzene; (×) o-xylene (♦) Absorption of pyrene (component);
(■) Desorption of deuterated (*d*-10) pyrene (calibrant);
(△) Sum of the component and calibrant Blood = SPME extraction from whole blood
Plasma = Standard analysis of plasma
SOF-PPY = Standard in the fiber method with PPY coatings
SOF-PEG = Standard in the fiber method with PEG coatings Blood = SPME extraction from whole blood
Plasma = Standard analysis of plasma
SOF-PPY = Standard in the fiber method with PPY coatings
SOF-PEG = Standard in the fiber method with PEG coatings Blood = SPME extraction from whole blood
Plasma = Standard analysis of plasma
SOF-PPY = Standard in the fiber method with PPY coatings
SOF-PEG = Standard in the fiber method with PEG coatings

CALIBRATION PROCEDURES AND DEVICES FOR INVESTIGATION BIOLOGICAL SYSTEMS

CROSS REFERENCE TO RELATED APPLICATIONS

This application is a divisional of U.S. patent application Ser. No. 11/706,167, filed Feb. 15, 2007, now U.S. Pat. No. 8,008,064, issued on Aug. 30, 2011.

U.S. patent application Ser. No. 11/706,167 is: a continuation of U.S. patent application Ser. No. 11/208,933 filed Aug. 23, 2005; a continuation-in-part of U.S. patent application Ser. No. 10/506,827 filed Sep. 7, 2004.

U.S. patent application Ser. No. 11/208,933 has issued as U.S. Pat. No. 7,232,689 and is: a continuation-in-part of U.S. patent application Ser. No. 10/506,827 filed Sep. 7, 2004 claims priority from U.S. Provisional Application 60/604,631 filed Aug. 27, 2004; and is a National Stage Entry of PCT/CA2003/000311 filed Mar. 6, 2003.

U.S. patent application Ser. No. 10/506,827 has issued as U.S. Pat. No. 7,384,794 and is a National Stage Entry of PCT/CA2003/000311 filed Mar. 6, 2003.

PCT Application No. PCT/CA2003/000311 claims priority to U.S. 60/427,833 filed Nov. 21, 2002; U.S. 60/421,510 filed Oct. 28, 2002; U.S. 60/421,001 filed Oct. 25, 2002 and U.S. 60/393,309 filed Jul. 3, 2002; and U.S. 60/364,214 filed Mar. 11, 2002.

The entirety of each document is incorporated herein by reference.

FIELD OF THE INVENTION

The present invention relates generally to calibration methods for quantifying or identifying components of interest in a biological system, such as in an animal.

BACKGROUND OF THE INVENTION

Presently, if one wants to accurately assess the concentrations of chemicals or drugs inside a living animal a sample of the blood or tissue to be studied is removed from the animal and taken to an analytical laboratory to have the chemicals of interest extracted and quantified. Typically a first step is a pre-treatment of the sample to convert it to a form more suitable for chemical extraction. In the case of blood this may be by the removal of blood cells and/or some blood components by the preparation of serum or plasma. In the case of a tissue sample this may be by many processes including freezing, grinding, homogenizing, enzyme treatment (eg. protease or cellulase) or hydrolysis. Subsequently chemicals of interest are extracted and concentrated from the processed sample. For example serum samples may be subjected to liquid-liquid extraction, solid phase extraction or protein precipitation followed by drying and reconstitution in an injection solvent. A portion of the injection solvent is introduced to an analytical instrument for chromatographic separation and quantification of the components. This method produces accurate results with high specificity for the compound of interest, but is time consuming and labour intensive. Also, because of the large number of steps in the process there is a significant chance of errors in sample preparation impacting the results. This method has good sensitivity and selectivity and accuracy for the target compounds but is limited in that the chemical balance the chemicals exist in inside the animal is disrupted during sampling. In many cases this disruption reduces the value of the results obtained, and in some cases makes this technique inappropriate for the analysis. Where the blood volume removed is a high proportion of the total blood volume of the animal, as is commonly the case when mice are used, the death of the animal results. This means that a different animal must be used for each data point and each repeat. By eliminating the need for a blood draw in this case, fewer animals would be required for testing and a significant improvement in inter-animal variation in the results would be achieved.

Alternatively biosensors have been developed for some applications in analysis of chemical concentrations inside animals. In this case a device consisting of a specific sensing element with associated transducer is implanted and produces a signal collected by an electronic data logger that is proportional to the chemicals to which the sensor responds. The main limitations of this type of device are that they normally respond to a spectrum of chemicals rather than having specificity for only one chemical. Of the spectrum of chemicals to which the sensor responds, some produce a greater and some a lesser response. Sensors are also susceptible to interferences where another chemical present in a system interferes with the response produced by the target chemicals. For these reasons biosensors are normally limited in terms of accuracy and precision. Finally biosensors are typically not as sensitive to low chemical concentrations as state of the art stand alone detectors such as mass spectrometers that are used in the above mentioned conventional analysis techniques and in solid phase microextraction. A strength of this technology is that the chemical balance in the system under study is not disturbed.

The in vivo procedure described here is a significant departure from conventional 'sampling' techniques, where a portion of the system under study is removed from its natural environment and the compounds of interest extracted and analyzed in a laboratory environment. There are two main motivations for exploring these types of configurations. The first is the desire to study chemical processes in association with the normal biochemical milieu of a living system, and the second is the lack of availability or impracticality frequently associated with size of removing suitable samples for study from the living system. Newer approaches that extend the applicability of conventional SPME technology, where an externally coated extraction phase on a micro fibre is used, seem to be logical targets for the development of such tools. As with any microextraction, because compounds of interest are not exhaustively removed from the investigated system, conditions can be devised where only a small proportion of the total compounds and none of the matrix are removed, thus avoiding a disturbance of the normal balance of chemical components. This could have a benefit in the non-destructive analysis of very small tissue sites or samples. Finally because extracted chemicals are separated chromatographically and quantified by highly sensitive analytical instruments, high accuracy, sensitivity and selectivity are achieved.

With the current commercially available SPME devices a stationary extraction polymer is coated onto a fused silica fibre. The coated portion of the fibre is typically 1 cm long and coatings have various thicknesses. The fibre is mounted into a stainless steel support tube and housed in a syringe-like device for ease of use. Extractions are performed by exposing the extraction polymer to a sample for a pre-determined time to allow sample components to come into equilibrium with the extraction phase. After extraction the fibre is removed to an analytical instrument (typically a gas or liquid chromatograph) where extracted components are desorbed and analysed. The amount of a component extracted is proportional to its concentration in the sample (J. Pawliszyn "Method and Device for Solid Phase Microextraction and Desorption", U.S. Pat. No. 5,691,206.).

To date commercial SPME devices have been used in some applications of direct analysis of living systems. For example they have been applied for the analysis of airborne pheromones and semiochemicals used in chemical communications by insects (Moneti, G.; Dani, F. R.; Pieraccini, G. T. S. *Rapid Commun. Mass Spectrom.* 1997, 11, 857-862.), (Frerot, B.; Malosse, C.; Cain, A. H. *J. High Resolut. Chromatogr.* 1997, 20, 340-342.) and frogs (Smith, B. P.; Zini, C. A.; Pawliszyn, J.; Tyler, M. J.; Hayasaka, Y.; Williams, B.; Caramao, E. B. *Chemistry and Ecology* 2000, 17, 215-225.) respectively. In these cases the living animals were non-invasively monitored over time by assessing the chemical concentrations in the air around the animal, providing a convenient means to study complicated dynamic processes without interference.

The current commercial devices do, however, have some limitations for in vivo analysis inside a living animal. Firstly, the application to chemical analysis inside animals requires greater robustness in both the extraction phase and the supporting fibre core. In addition, most of the extraction phases currently available are better suited for more volatile and less polar compounds. Only one phase is suitable for liquid chromatography (LC) applications (carbowax/templated resin). Analytes of interest that typically circulate in living systems are less volatile and more polar and require LC analysis, so new or modified extraction phases are indicated. The overall dimension of the current device is typically too large for direct in vivo analysis and for direct interfacing to microanalytical systems, the time required for the LC extraction phase to come into equilibrium with chemicals in a sample is relatively long (typically 1 hr or more in a well-stirred sample) and analysis is sensitive to degree of convection in the sample. Also the present SPME devices cannot be conveniently coupled to positioning devices necessary for in-vivo investigation at a well-defined part of the living system.

It is, therefore, desirable to provide a method and a device that allows minimally invasive sampling, quantification or analysis of a biological system.

SUMMARY OF THE INVENTION

It is an object of the present invention to obviate or mitigate at least one disadvantage of previous devices and methods for evaluating components of interest in biological systems.

According to an aspect of the invention there is provided a method of determining the concentration of a component in a sample. The method comprising steps of: adding a calibrant to extraction phase prior to contact of said extraction phase with said sample, making said contact between said extraction phase and said sample for predetermined extraction time, terminating said contact and determining said concentration of said component using amounts of said calibrant and said component present in said extraction phase after said contact.

The invention further provides a membrane extraction method of determining concentration of a component in a sample. The method comprising the steps of: adding a calibrant to a stripping fluid prior to contact of said stripping fluid with a membrane, making contact between said membrane and said sample on one side of said membrane and between said membrane and said stripping fluid on the other side of said membrane, maintaining said contact to allow said membrane extraction to occur, introducing said stripping phase into an analytical instrument and determining said concentration of said component in said sample using measured amounts of said calibrant and said component in said stripping phase.

Additionally, the invention provides a method of delivering a compound into investigated system. The method comprising adding a well defined amounts of said compound into coating of a fiber prior to exposure of said fiber to said investigated system.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 5 shows a schematic of housing and device for soft tissue sampling.

DETAILED DESCRIPTION

Figure 1:
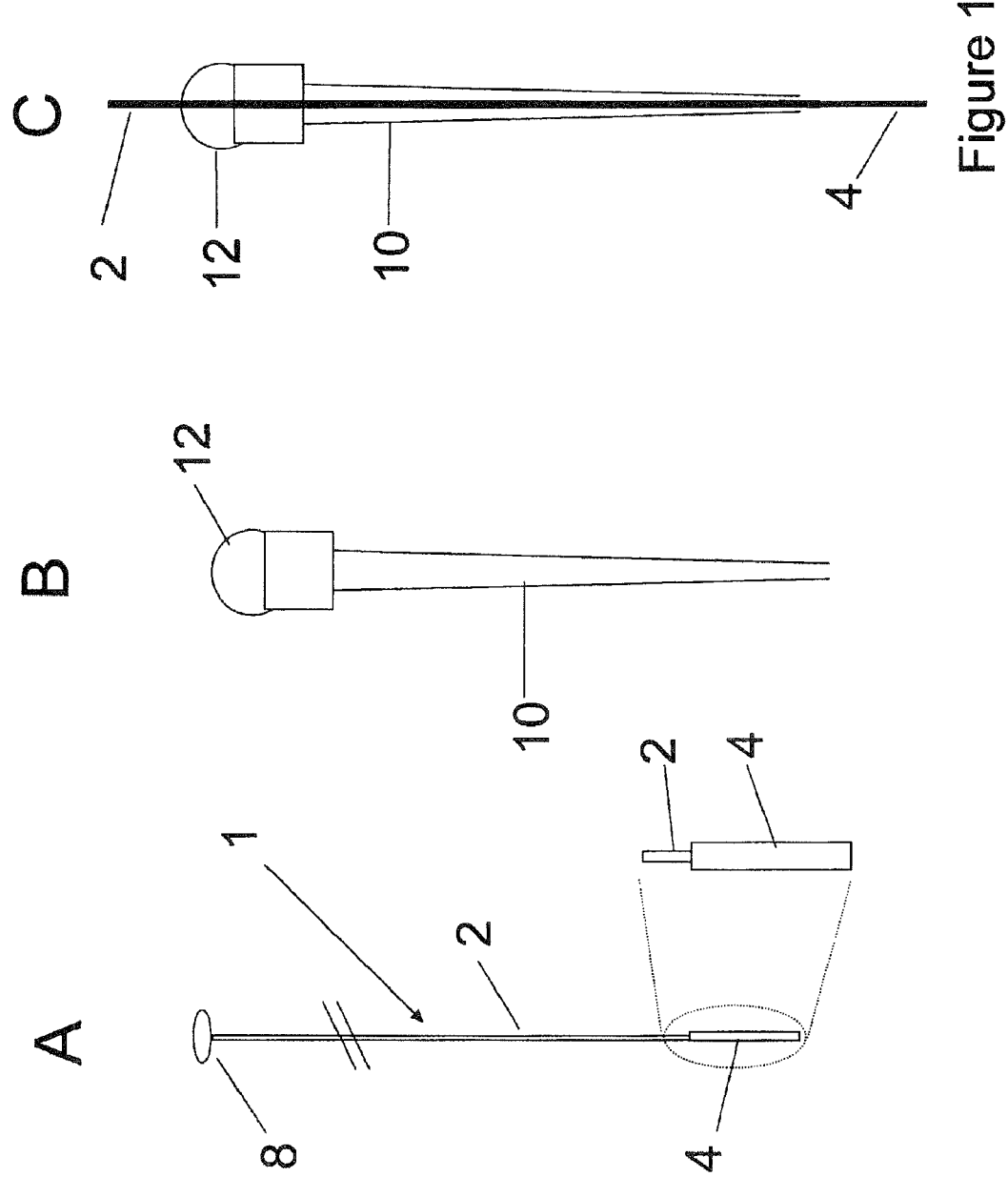
FIG. 1 shows a general schematic of device design according to an embodiment of the invention.

The invention relates to a method and device based on coated fibre, optionally in combination with a positioning device, or separation and detection technologies particularly useful for in vivo studies of compounds of interest (identities and concentrations) in animals, or parts of animals.

According to an aspect of the invention, a method of determining the concentration of a component in a sample is provided. The extraction phase contains calibrant. The extraction phase is placed in contact with the sample allowing extraction of the component of the sample into the extraction phase. At the same time the calibrant present in the extraction phase is being extracted into the matrix. After the contact between the sample matrix and the extraction phase is terminated the amount of the calibrant remaining in the extraction phase and the amount of the component extracted can be used to calculate the concentration of the component.

The extraction phase or portion of the extraction phase can be placed in analytical instrument for determination of the amounts of the amount of the calibrant remaining in the extraction phase and the amount of the component extracted during the contact of the extraction phase with the sample. Optionally determination process in the analytical instrument can include step of desorption of the calibrant and the component into organic solvent contained in wells of a multiwell plate to facilitate parallel desorption step resulting in increase of the throughput of analysis.

There are at least two options for length of predetermined extraction times. The extraction time can be equal or longer compared to the equilibration time between the extraction phase and the sample allowing full equilibration of the component between extraction phase and sample. In that case the calibration can be performed based on ratio of appropriate sample matrix-extraction phase distribution coefficients corresponding to the calibrant and the component.

As another option, the extraction time can be shorter compared to the equilibration time. In that case the amount of component extracted corresponds to the rate of mass transfer between the sample matrix and the extraction phase and the amount of calibrant remaining in the extraction phase to the rate of mass transfer between the extraction phase and the sample matrix. The calibration is performed by using the ratio of the corresponding rates.

The calibrant in the extraction phase method is particularly powerful for microextraction approach where the small volumes of the extraction phase compared to the volume of the sample matrix are used resulted in substantial amount of calibrant being transported to the sample matrix. When applying this approach to analysis of biological samples in vitro or in-vivo the preferred volume of the extraction phase is less then one milliliter.

The extraction phase can be either gas as in static or dynamic headspace techniques, or liquid as in liquid extraction or alternatively solid as in sorbent extraction.

Polymer can be used as extraction phase. Polymer can be liquid as poly(dimethylsiloxane) (PDMS) or poly(ethylene glycol) (PEG) or it can be solid, for example poly(divinylbenzene) (DVB).

The extraction phase can be made in different shapes to facilitate convenience of use or increase mass transfer between the extraction phase and the sample matrix. Rods are easy to handle, but flat thin membranes or coatings have high surface area facilitating rapid mass transfer between the sample matrix and the extraction phase. The coating configuration benefits from the strength of the support.

Fiber geometry and in particularly small coated fiber configuration is very useful to deliver calibrant to the sample and transfer the extracted component and remaining calibrant from the sample to analysis instrument. Coated micro fibers are of particular use when sampling living systems including animals since minimum damage during sampling procedure occurs.

Tube geometry is another useful format of a support, which facilitates extraction during drawing the sample through the tube. The tube could be in a form of a needle or a cartridge.

As another option, the extraction phase can be sealed in the specially designed cartridge to avoid loss of calibrant prior to contact with the sample matrix or after the contact has been terminated to avoid loss of both calibrant and the component.

There are at least two options for the level of calibrant release from the extraction phase during contact with sample matrix. The calibrant can be fully retained during the contact. In that case the calibrant is strongly bound by the extraction phase and only released into analytical instrument during desorption. It can be used to calibrate response of the instrument or the concentration when the calibrant loading conditions are identical to the extraction conditions of the compound.

The other option is when the calibrant is partially released from the extraction phase during the contact with sample. In this case the calibration can be either based on the ratio of corresponding distribution constants when equilibrium is reached or the ratio of corresponding mass transfer coefficients for the pre-equilibrium conditions. The equilibrium case is of particular use when performing in-vitro extractions and the volume of sample is small. In that case the amount of component extracted is maximum resulting in optimum sensitivity. The pre-equilibrium case is very useful for on-site, including in-vivo extractions.

Further, the process of the extraction can be automated including step of addition of the calibrant to the extraction phase to increase throughput of the extraction and analysis. For example, the coated fiber located in a needle can be automatically exposed first to a vial containing calibrant prior to contact with the sample placed in another vial.

The calibrant is chosen to have similar physicochemical properties compared to the component, including the distribution constant and the rate of mass transfer between the extraction phase and the matrix to properly perform calibration. The best choice for calibrant is use of isotopically labelled analogue of the target component.

According to an aspect of the invention, a membrane extraction method of determining concentration for determining concentration of a component in a sample is described. The calibrant is added to a stripping fluid prior to contact of said stripping fluid with a membrane. The stripping fluid containing the calibrant is contacting one side of the membrane and sample the other side. During the contact the mass transfer of the component to the stripping phase and calibrant to extraction phase occur. Then the stripping phase is introduced into an analytical instrument for determination of amount of the calibrant and the compound present in that phase, which is used for calculation of the concentration of the component in the sample using ratio of mass transfer coefficients corresponding to the calibrant and the component. The membrane extraction and the calibration approach is particularly useful for continuous extraction process.

Additionally, according to the invention there is provided a method of delivering a compound into investigated system. The method comprising adding a well defined amounts of said compound into coating of a fiber prior to exposure of the fiber to said investigated system, which could be analytical instrument or living animal or a plant. Using fibers for delivery of the compound reduces risk of exposure to toxic compounds. The compound delivered to instrument can serve as a calibrant and provide appropriate response factor for that instrument to that compound. Alternatively the compound can be a drug or other bioactive component and it can be delivered directly to tissue of living system.

The method of the invention may be used for measuring or identifying one or more component of interest in an animal or animal tissue comprises the steps of: positioning a fibre within the animal or tissue, wherein the fibre is at least partially coated with an extraction phase for adsorbing the component of interest from the animal or tissue. The extraction phase is positioned within said animal or tissue, and thus the component of interest is adsorbed onto the extraction phase for a pre-determined period of time. Following this, the fibre is removed from the animal or tissue; and the component of interest is desorbed from the extraction phase into an analytical instrument for measurement or identification.

The method of the invention is suitable for pharmacokinetic studies, wherein observation of analyte levels in a biological system over time is desirable to conduct with little or no blood or biological fluid removal from the system. In the case where blood samples would normally be drawn periodically for pharmacokinetic studies, the invention advantageously allows similar observations without removal of blood volume from the subject.

The extraction phase may specifically adsorb the one or more component of interest, and is preferably located at a terminal end (or "distal" end) of the fibre.

The period of time for which the fibre is positioned within the animal or animal tissue can be any acceptable time allowing adsorption of a detectable amount of the component of interest. For example, this time may be equivalent to equilibration time for a component of interest, or it can be less than equilibration time for a component of interest.

The component of interest can be any desirable component. For example, it may be a bacteria, viruses, sub-cellular components, biopolymers, DNA, proteins, drugs, drug metabolites, hormones, vitamins, environmental contaminants, chemicals, or cells. Any component capable of detection can be selected.

The animal or animal tissue can be is selected from the group consisting of single cell animals, live eggs, mice, rats, rabbits, dogs, sheep, pigs, monkeys and humans. As discussed further herein, an embodiment of the invention requires only samples, and is not necessarily conducted in an animal or in animal tissue. The animal tissue could be, for example, isolated cells and organs.

The fibre may be positioned within a blood vessel, and this embodiment would allow analysis of a component of interest adsorbed from blood flowing through said blood vessel. Optionally, the step of positioning said fibre comprises guiding the fibre into position within the blood vessel using a catheter. Other areas in an animal in which the fibre may be positioned include a) muscle, brain, soft tissue, or organ of said animal; and the component of interest is adsorbed from interstitial fluid or intracellular fluid; b) an inner part of spine, scull or bone; and the component of interest can be adsorbed from the bone, inner fluids including spinal fluid, bone marrow or brain fluid; or c) a cell of an animal, and an adsorbed component is extracted from the inner cellular fluid or sub-cellular component of a single cell of an animal. Of course, the invention is not limited to these examples.

During positioning, the fibre may be disposed within a housing having a sealed penetrating end. In this case, the method may include the step of opening the penetrating end once the fibre is positioned as desired within the animal, exposing the extraction phase within said animal.

Alternatively, the fibre may be inactive during said positioning followed by activating the extraction phase using change of electrical potential or optical means to allow adsorption of said component of interest. An example of this could be if the fibre is made of a metal which can be activated to attract certain components. Other possibilities for electrical activation of the fibre are within the scope of the invention.

The invention may use one fibre, or a plurality of fibres arranged as an array or bundle. As used herein, discussion of a fibre in the singular does not preclude the use of more than one fibre, or a bundle of fibres. In the case where a plurality of fibres are used, they may be disposed in a single position within the animal, or they may be disposed in more than one position within said animal, so as to obtain readings from multiple locations simultaneously. The fibre may be one or more optical fibres, such as a bundle of optical fibres.

In one embodiment of the invention, the extraction phase may additionally comprise a strongly bound calibrant which is retained in the extraction phase during the step of adsorbing. Alternatively, a weakly bound calibrant can be used which is released from the extraction phase during the step of adsorbing according to convection conditions and diffusion coefficient. The amount of the weakly bound calibrant remaining after the pre-determined period of time can be observed. This can also be used to deliver a desired compound to the animal or animal tissue.

In another embodiment, a strongly bound reagent may be added to the extraction phase prior to extraction. This reagent may be a strongly bound reagent which reacts with the component of interest. An example of such a strongly bound reagent is one that labels the component of interest with a fluorescence tag. Another example is a reagent such as an enzyme, in which case the component of interest may be a substrate for that enzyme. Such an enzyme may be one that digests a protein directly onto the fibre, for example trypsin or a trypsin cofactor. Further, the reagent may be added to the extraction phase after the step of adsorbing, in which case the reagent subsequently reacts with the component of interest.

The reagent can be added to the extraction phase by spraying or dipping the reagent onto the extraction phase.

The method of the invention may be one in which a polymerase chain reaction (PCR) is conducted directly on the extraction phase. In such an embodiment, the components of interest are DNA or DNA fragments, the fibre is subject to periodic cycles of alternating cooling and heating, the reagent comprises polymerase and nucleic acids, and the method results in a polymerase chain reaction (PCR) on the extraction phase.

The reagent may comprise an ionization matrix utilized in matrix assisted laser desorption and ionization (MALDI). MALDI analysis of the extraction phase can be conducted with any embodiment of the invention amenable to such a method of measurement or compound identification. Any number of analytical instruments may be used with the invention, such as a spectrometer such as a time of flight instrument mass spectrometer (TOFMS) or an ion mobility spectrometer. After desorbing the component of interest from the extraction phase, measurement or identification of the component may occur in an analytical instrument such as a gas chromatograph, a liquid chromatograph, a capillary electrophoresis instrument, a capillary electrochromatography instrument and a microfluidic device.

The invention may include positioning of the fibre in an analytical instrument after the step of adsorbing. This could, for example involve laser irradiation of the fibre to desorb the component of interest from the extraction phase into the analytical instrument. In such a case, the fibre can be irradiated in a region not coated with the extraction phase, so as to desorb the component.

The invention may allow introduction of the fibre directly into a mass spectrometer prior to the step of desorbing. The fibre may be introduced into a mass spectrometer by insertion into a small solvent volume in a nanospray needle, followed by the step of desorbing, and electrospray of a desorbed component of interest.

After removing the fibre from the animal or tissue, the fibre may be exposed to a high voltage resulting in field desorption of the component of interest directly from the extraction phase into the mass spectrometer.

Separation of components of interest from the extraction phase may occur directly in a separation capillary or channel of the analytical instrument. The step of desorbing may be conducted in a small bore cartridge filled with a desorption solvent following by automated measurement or identification of a component of interest in the analytical instrument. In such a case, the fibre may be placed in the small bore cartridge immediately following the step of removing the fibre from the animal or tissue, and the cartridge can either be analysed immediately or sealed and transported or stored prior to automated measurement or identification.

The invention also relates to a device for adsorbing one or more component of interest from an animal or animal tissue. The device comprises one or more fibre having an at least partially coated end. The end is at least partially coated with an extraction phase for absorbing one or more component of interest. The device also includes a positioning device for guiding the at least partially coated end of the fibre into position within the animal or animal tissue.

Optionally, the fibre diameter can be of millimeter to nanometer dimensions, and formed of any acceptable material that would be amenable for use in the intended application. Such materials may include fused silica, plastic, carbon or metal wire. The fibre may be a plurality of optical fibres formed from fused silica.

Optionally, the fibre may be a hollow tubing having the extraction phase coated on an inside surface of the tubing. In this instance, the tubing may be in communication with a pump capable of draw up or ejecting a sample from the tubing. The pump may be of any acceptable type known for use with tubing. Alternatively, the fibre may be a hollow tubing having the extraction phase coated on an outside surface thereof. In this case, the tubing could be sealed at one end and have a pump in communication with the tubing to blow fluid, such as a gas or liquid, into the tubing. This would allow expansion of the tubing as desired, which could increase the surface area of the extraction phase as required.

The device of the invention may additionally comprise a sheath surrounding the fibre for protection and easy handling.

The extraction phase is advantageously biocompatible, as necessary. Optionally, the fibre may be additionally at least partially coated with a biocompatible protection layer, which can surround the extraction phase. Such a biocompatible protection layer may comprise polypyrrole or derivatised cellulose, or any such polymer as would provide protection.

The extraction phase itself may comprises any composition capable of binding a component of interest. It may, for example be a polymeric composition such as substituted or unsubstituted poly (dimethylsiloxane), polyacrylate, poly (ethylene glycol) or polypyrrole. Alternatively, the extraction phase may have a bioaffinity agent on its surface, such as a selective cavity, a molecular recognition moiety, a molecularly imprinted polymer, or an immobilized antibody. The extraction phase may contain any of these in combination.

The extraction phase can, alternatively be an extraction and ionization matrix for MALDI-TOFMS analysis, and may contain a calibrant molecule, as discussed above.

The fibre may be contained in a housing closed at one end, for opening and exposing the fibre when appropriately positioned within the animal or animal tissue. Such a housing may be a sealed leaf structure, or any other such openable sealant.

The positioning device itself may a catheter, for those applications where the fibre is guided into a blood vessel, such as a vein, or other tubular biological structures, as discussed in more detail below. Further, the position device may be an x-y-z micro positioning stage, for those applications wherein a tissue can be positioned on such a stage, and its movement finely controlled. The positioning device comprises an automated system, which may be rendered attachable to the animal or animal tissue. The positioning device may additionally be used to position said fibre within an analytical instrument for desorption of the component of interest from the extraction phase. The positioning device can optionally be used to place the fibre directly inside a separation capillary or channel, and could be used to couple the fibre to a laser beam facilitating desorption of a component of interest from the extraction phase. The positioning device may be used to facilitate desorption of a component of interest into an analytical instrument.

In the case where a plurality of fibres are used, these fibres may have the same or a different extraction phase coated thereon, so that more than one component of interest can be detected. More than one extraction phase can be combined on a fibre, so that a variety of components of interest can be detected.

The device may additionally comprise an agitator to cause movement of the coated end of a fibre, for example axial or horizontal movement of the fibre. In the case where the fibre comprises hollow tubing having the extraction phase coated on an inside surface of the tubing, the agitator may force the tubing to draw up a sample into the tubing. This can be effected by mechanical means or by creating a pressure differential forcing the tubing to draw up a sample into the tubing. The agitator may comprise an inflatable balloon.

The invention further relates to a method of measuring or identifying one or more component of interest in liquid samples arranged in a plurality of wells in a multiwell plate. This involves simultaneously submerging a distal end of a plurality of fibres within the plurality of wells, respectively, the distal end of each fibre being at least partially coated with an extraction phase for adsorbing the component of interest from the liquid sample. Following this, the component of interest is adsorbed onto the extraction phase for a pre-determined period of time. The fibres are then simultaneously removed from the wells, and are positioned in an analytical instrument for desorption, and measurement or identification of the component of interest from the extraction phase. Such an analytical instrument may be any of the ones noted above, such as a MALDI analytical instrument or a multichannel micromachined microfluidic device.

The inventive device for measuring or identifying one or more component of interest from liquid samples arranged in a plurality of wells in a multiwell plate, for use with the method described herein comprises a plurality of fibres, each having an at least partially coated distal end, said end being at least partially coated with an extraction phase for absorbing the component of interest. A positioning device is used for guiding the coated distal end of said fibres into a submerged position within the plurality of wells of the multiwell plate, for removing said fibres from said wells, and for positioning said fibres into an analytical instrument.

According to one embodiment, a small sterile device containing a small diameter fibre with an associated extraction phase coated thereon is used. The extraction phase has affinity for one or more compounds of interest. After exposure of the extraction phase in vivo, the device may be removed for quantitative or qualitative analysis in an analytical instrument.

A device for in vivo study of chemical concentrations consists of a fibre or wire and associated extraction phase. The fibre or wire may be made of fused silica, metal, carbon, graphite or a polymeric material. The device may or may not have an attached or removable handle. The device may have an associated or removable housing such as an outer needle sheath to provide access for the device to the tissue under study. Preferably the device is introduced to the tissue under study via a standard medical positioning device such as a catheter or microdialysis cannula. After extraction the housing may be retained if it is used in association with desorption, or discarded if it is not so-needed. Where a medical device is used to provide access to the tissue under study, multiple devices may be used with a single catheter for instance, obviating the need to puncture the skin or other tissues separately for each extraction.

A process of carrying out in vivo solid phase microextraction uses a fibre with associated extraction phase, which may or may not have an associated housing. In any case a means is provided to position the device in the tissue for the desired extraction. For extraction the device is left in contact with the tissue under study for a sufficient period of time to allow equilibration with the chemicals in the tissue, insensitivity to convective forces and/or maximal sensitivity. It is likely the device could be used to monitor chemical concentrations in humans or experimental animals such as rats, mice, dogs, sheep or rabbits. Subsequent to sampling the device is placed in an appropriate analytical instrument or desorption device so that at least one chemical component extracted is desorbed for quantification.

The device and process described are used to monitor chemical concentrations in vivo in a living animal, without causing a disruption in the dynamic balance in the animal systems. Some specific benefits can be described. Because no blood need be drawn for the analysis, animals are less stressed. This would allow for more data points to be collected for pharmacokinetic profiles, allowing for better data on which to make drug design decisions. It would also allow or for sampling of blood or tissue drug concentrations at multiple sites in an animal, to better assess the effects of differing metabolic processes in different locations in animals. Where more data points are collected from one animal, a reduction in inter-animal variation in the results arises. This variation can often obscure real pharmacokinetic trends and so by eliminating it, better pharmacokinetic data can be collected. Conventional sampling where a specific sample of blood/tissue is removed from an animal causes a disruption in the normal chemical balance of the animal. Each successive sample enhances the impact on the normal dynamics of the animal. With sampling according to the invention, where only a negligible portion of the analytes of interest are removed, the normal chemical balance remains unperturbed, thus eliminating the effect of sampling itself on the results. Genetic variation in drug metabolism within a population gives rise to differing pharmacokinetics for the same drug among individuals. The device and process described would be beneficial both in monitoring the effect of genetic variation on metabolism of existing drugs, and for directing the design of novel drugs to take advantage of variable genetic profiles for tailored drug design.

Calibration of the device may be achieved in several ways. Where equilibrium extraction is achieved, calibration by comparison to matched in vitro samples is simple and effective. Under non-equilibrium extraction or where it is not possible to match in vitro samples to the in vivo system, calibration may be achieved by pre-loading the fibre with a suitable calibrant. Direct quantification based on analyte physico chemical properties is also possible using spectroscopic analysis of the analytes directly from the fibre.

Optionally, calibrant can be added to the extraction phase to perform internal calibration to quantify components of interest. The rate of loss of calibrant from the extraction phase is used to estimate various degree of convection in the system and the matrix affect facilitating accurate in-vivo or in vitro calibration.

The device accomplishes both sampling and sample preparation during in vivo analyte extraction. Sample preparation may be limited to isolation from sample matrix and concentration in the extraction phase. It may also include additional processing on the fibre. Examples of this are derivatization of analyte to a form with higher sensitivity in detection through either a modification of product polarity or fluorescent tagging, amplification of analyte copy number in the case of DNA analysis to improve signal intensity, and protein or enzymatic digestion in the case of general biomolecules (eg. proteins) to convert them to a form more amenable to instrumental analysis (eg. peptide fragments). In all cases the goal of this on-fibre processing is to enhance detection/quantification of the target analytes.

In the conventional SPME device the overriding goal in device design was optimizing the affinity of the analyte for the extraction phase on the fibre, to maximize analytical sensitivity. In the case of in vivo analysis the issue of coating biocompatibility is equally important. Device design must take into account both biocompatibility and affinity in the extraction phase.

Because of the simplicity inherent in both the device design and the process, multiplexing in both sampling and analysis is much more practical that it has been for conventional analyses. Fibres may be grouped together in bundles, with fibres having either the same or different coatings, allowing for both sampling and quantification from many fibres at once, rather than one at a time.

Another advantage of the device and process is that quantification is performed separately from sampling, using conventional high sensitivity instrumental analysis. This allows better sensitivity and selectivity than are achievable where the detection is coupled directly to the sampling/sample preparation as is the case for biosensors. An interface is used to couple the fibre to the analytical instrument. This may be as simple as the off-line desorption of analytes into solvent filled wells in a multi-well plate, to a more sophisticated dedicated interface for thermal, field, solvent or laser desorption. In the case of a dedicated interface for solvent desorption, small internal diameter coupled with efficient solvent flow enhance desorption kinetics so that analytes may be removed from the fibre as quickly as possible.

Although the discussion thus far has focused on using a device without compounds of interest initially loaded into the extraction phase, to investigate chemical concentrations in a living system, the device described is equally suited to the delivery of a precise amount of a chemical compound to a precisely targeted tissue. If a device is first loaded with a pre-determined amount of compound of interest, it can be accurately positioned at the site of interest, where compounds will move out of the device according to kinetic and/or thermodynamic principles and thus supply the chemical to the tissue. This would be of value in targeted drug dosing where only a specific tissue is exposed to a drug compound.

FIG. 1, part A illustrates an extraction device 1 consists essentially of an extraction phase 4 coated on a fibre or wire 2 to be used with a positioning device to accurately locate the device in a tissue. The entire device is sterilizable by one or more of the conventional means of sterilization, such as autoclave, ethylene oxide, UV or gamma irradiation. The uncoated end of the wire may or may not include a handle 8 to facilitate positioning of the device. The length of the wire is variable 7 depending on the application requirements. The extraction phase 4 could be a polymeric layer prepared on the wire surface, particulate adsorptive or absorptive material glued or otherwise affixed to the wire surface, or immobilized biorecognition agents such as antibodies nucleotides or protein receptors. When constructed of the stainless steel wire described below the extraction device is quite flexible. It will follow curves in a vein or catheter and normally resume a straight configuration when removed. The device is useful for the application of monitoring concentrations of drugs and their metabolites in blood or other tissues, either in single point monitoring or in multiple point (time course) monitoring.

FIG. 1, part B illustrates standard medical catheter is shown in schematic form having a catheter body 10 and a sealing septum 12 (PRN). PRN is the commonly used term for an i.v. adapter to seal a catheter, incorporating a piercable septum, marketed by Beckton Dickinson. In the text that follows applications are described that use such a catheter for intra venous (i.v.) sampling. In practice, catheters are available for accessing other vessels as well, so applications are not limited to i.v. ones. For instance arteries, vessels within organs or capillaries may also be accessed using similar devices.

FIG. 1, part C, illustrates an embodiment comprising the extraction device alone with no support rod and no handle may be introduced to a blood vessel through a previously placed medical catheter 10 with attached PRN 12. The end of the extraction device with the extraction phase 4 may be contained in a sterile hypodermic needle that is used to pierce the PRN and provide access to the catheter. The extraction device is pushed partly into the catheter by means of the support wire 2 and the hypodermic needle is withdrawn. In this case the PRN provides a seal around the device to prevent blood loss. The extraction device 1 is then pushed into the catheter and blood vessel by an appropriate amount so that the extraction phase is exposed to the flowing blood. The catheter is then flushed with saline to prevent clotting in the catheter. After the required time for the extraction of drugs and metabolites the hypodermic needle is once again used to pierce the PRN to provide a port for removal of the extraction device. The extraction device is then removed from the housing, rinsed and packaged for transport for analysis. The coated fibre can be placed inside a micro-syringe as described in U.S. Pat. No. 5,691,206, for easier handling with a catheter or other positioning device.

Figure 2:
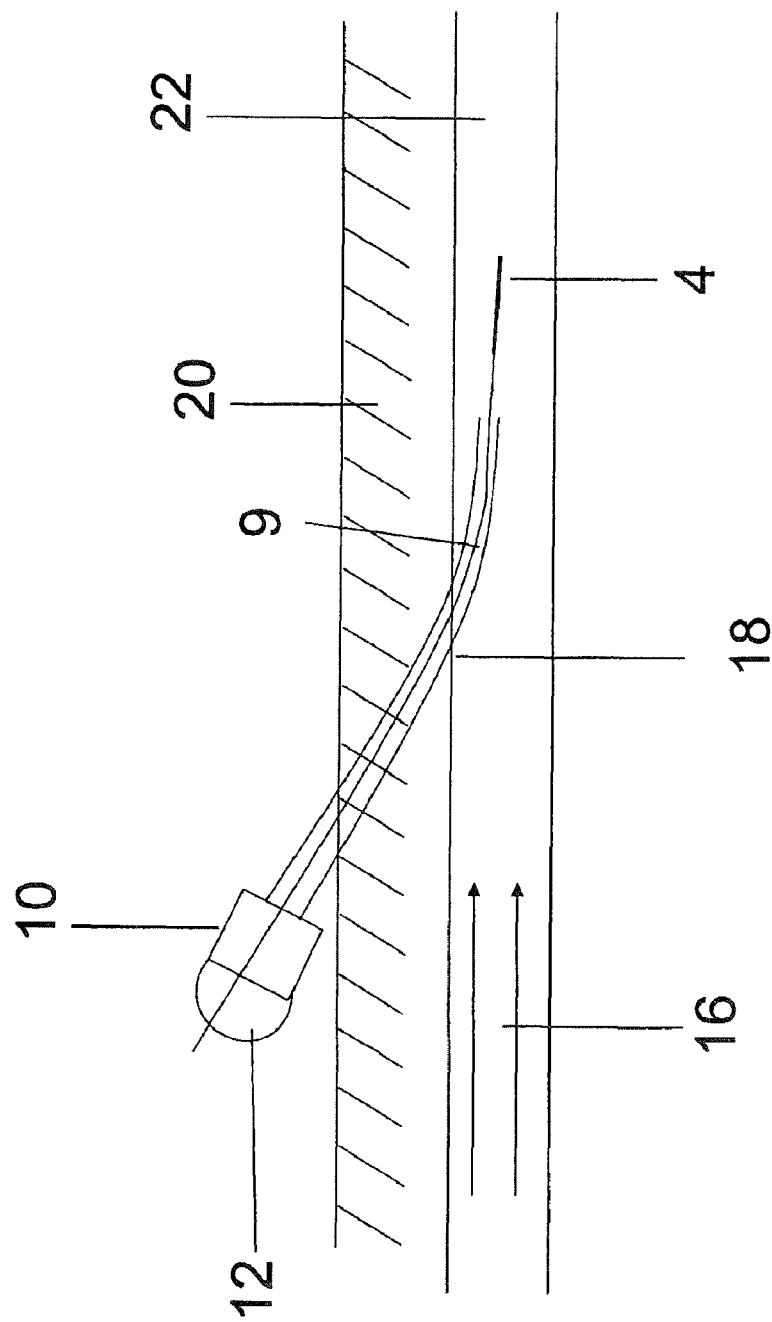
FIG. 2 illustrates the use of a medical catheter to position device accurately within a vein.

FIG. 2 shows the use of a medical catheter 10 passing through the skin 20 and vein wall 18 to position the extraction device 9 with PRN 12 inside a vein 22 with blood flow 16 past the exposed extraction phase 4. In this position the extraction device has been fully depressed through catheter so that the extraction phase is fully exposed to flowing blood outside of catheter. PRN 12 is still accessible to allow for flushing to ensure patency of the catheter.

Figure 3:
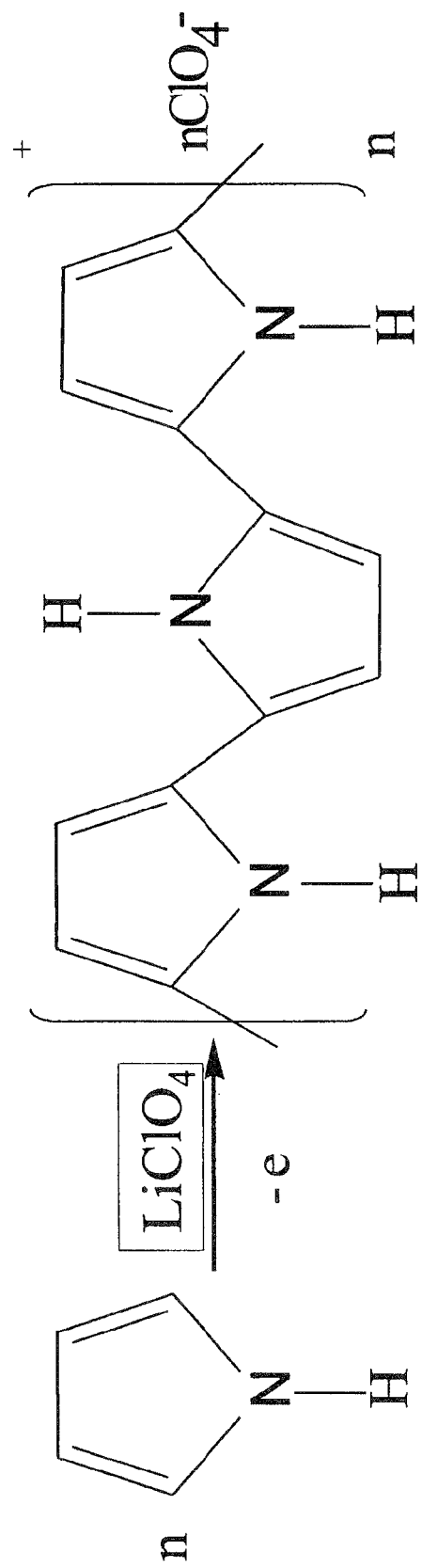
FIG. 3 shows a schematic of the polypyrrole polymerization reaction.

FIG. 3 illustrates a schematic of the polypyrrole polymerization reaction. As an example of an extraction phase, polypyrrole may be deposited onto the surface of a fine metal wire by electrolytic oxidation under conditions of controlled potential The polymer can be prepared on thin stainless steel wire as described below. The resulting polymer can then serve as the extraction phase to extract pre-concentrate drug compounds directly from blood flowing in a vessel. An exemplary preparation of coating a stainless steel wire with polypyrrole is provided in Example 1.

Medical Sampling Device

In use it may be desirable to provide a housing or sheath to allow access to the tissue site of interest. The housing is also important to ensure correct positioning of the device at a specific location in the tissue or site under study. This may be by puncture of the skin and/or blood vessel followed by positioning of the phase at a specific site for analysis, incorporation of multiple fibres and agitation means. The housing may also be required to provide a seal to prevent blood from escaping past the device during sampling. The nature of the associated housing will be dependent on the site to be sampled.

FIGS. 4 to 9 provide schematic illustration of options for the devices and described herein.

Figure 4:
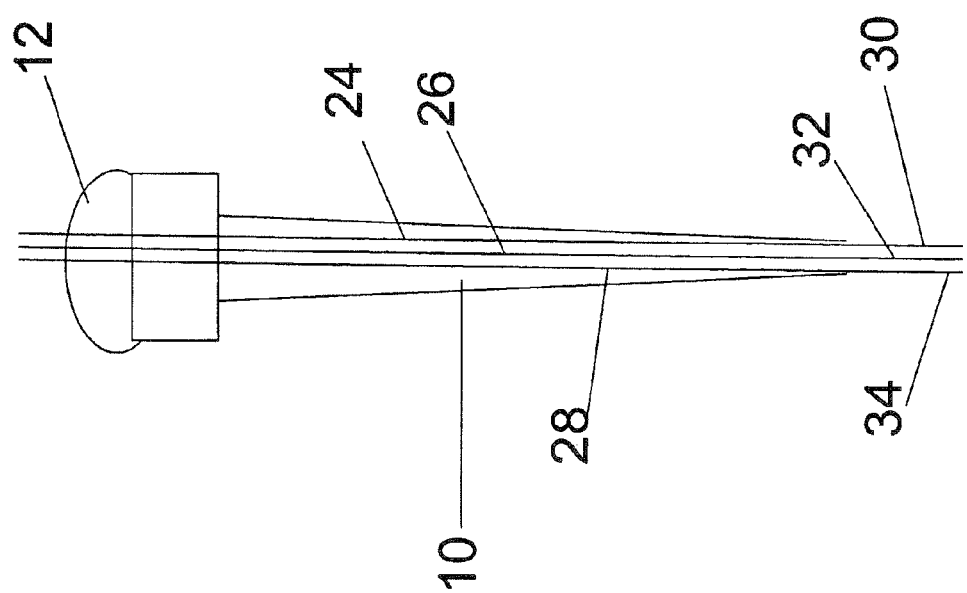
FIG. 4 is a schematic of a catheter with multiple coated fibres.

FIG. 4 shows modifications to the device and a housing for multi-fibre sampling using a commercial catheter. Fibres 24, 26 and 28 are coated by coating 30, 32 and 34 respectively, which can be the same type of coating to increase capacity of the device, or preferentially each fibre having different highly selective coatings, such as antibodies designed to recognized only defined components of interests in a living animal.

The device may also be used for sampling from an unpressurized medical port such as a microdialysis cannula. Because such a port is not pressurized, there is no need for a seal to prevent fluid from flushing past the device during sampling, which obviates the need for an additional sheath or specialized housing during sampling. The device has significant advantages over conventional microdialysis sampling because it is not necessary to either add or remove fluid from the tissue to sample. In conventional microdialysis analysis a portion of the fluid that diffuses into the cannula from the surrounding tissue may be removed for analysis. Alternatively synthetic fluid is pumped into the cannula and then to an analytical instrument for semi-continuous monitoring. In both instances the fluid balance of the tissue is disrupted during sampling, by reduction in volume in the first instance and by dilution in the second. Analysis using the device according to the invention would not disrupt the biochemical balance in the tissue as it does not cause such an imbalance.

FIG. 5 shows a modified housing in part A and extraction device in part B appropriate for sampling directly from soft tissue. When the device is in the retracted position the housing as seen in FIG. 5, part A, is constructed of a rigid tube 40 with a handle 46 and has a sealed tip 44 for penetrating soft tissue. The tip is constructed from two or more leaves separated from each other part way up the housing by a cut or slot 42 and are normally held together by spring action to seal the tip. FIG. 5, part B shows the extraction device supported in a thick tubing 6 for opening up the leaves of the needle end to allow exposure of extraction phase for sampling.

Figure 6:
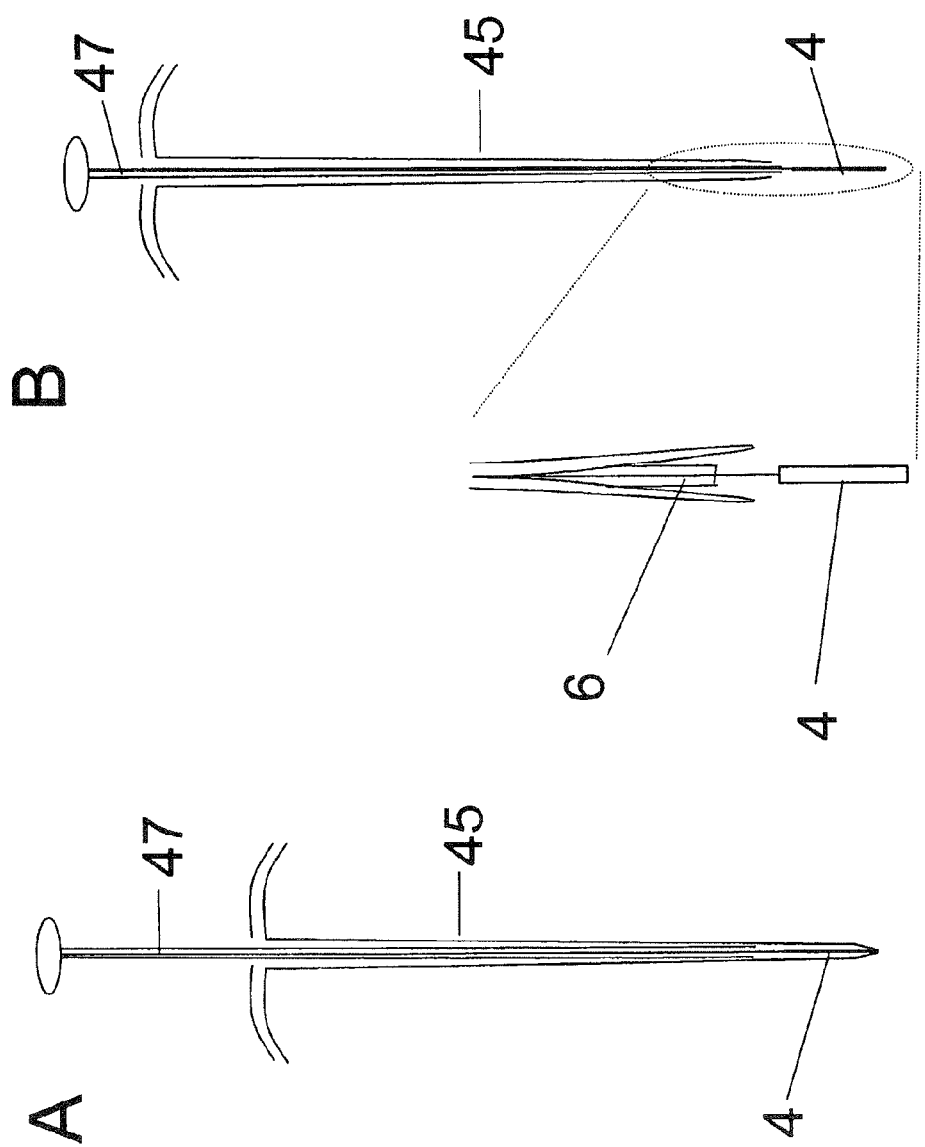
FIG. 6 illustrates operation of housing and device for soft tissue sampling.

FIG. 6 shows a schematic of the use of the extraction device and housing for soft tissue sampling. FIG. 6, part A, shows the extraction device 47 within the housing 45 in retracted position. FIG. 6, part B, shows the extraction device 47 in the housing 45 in exposed position. The supporting wire 6 moves with extraction device to force open the leaves at tip of needle to allow extraction phase on wire to pass through.

Figure 7:
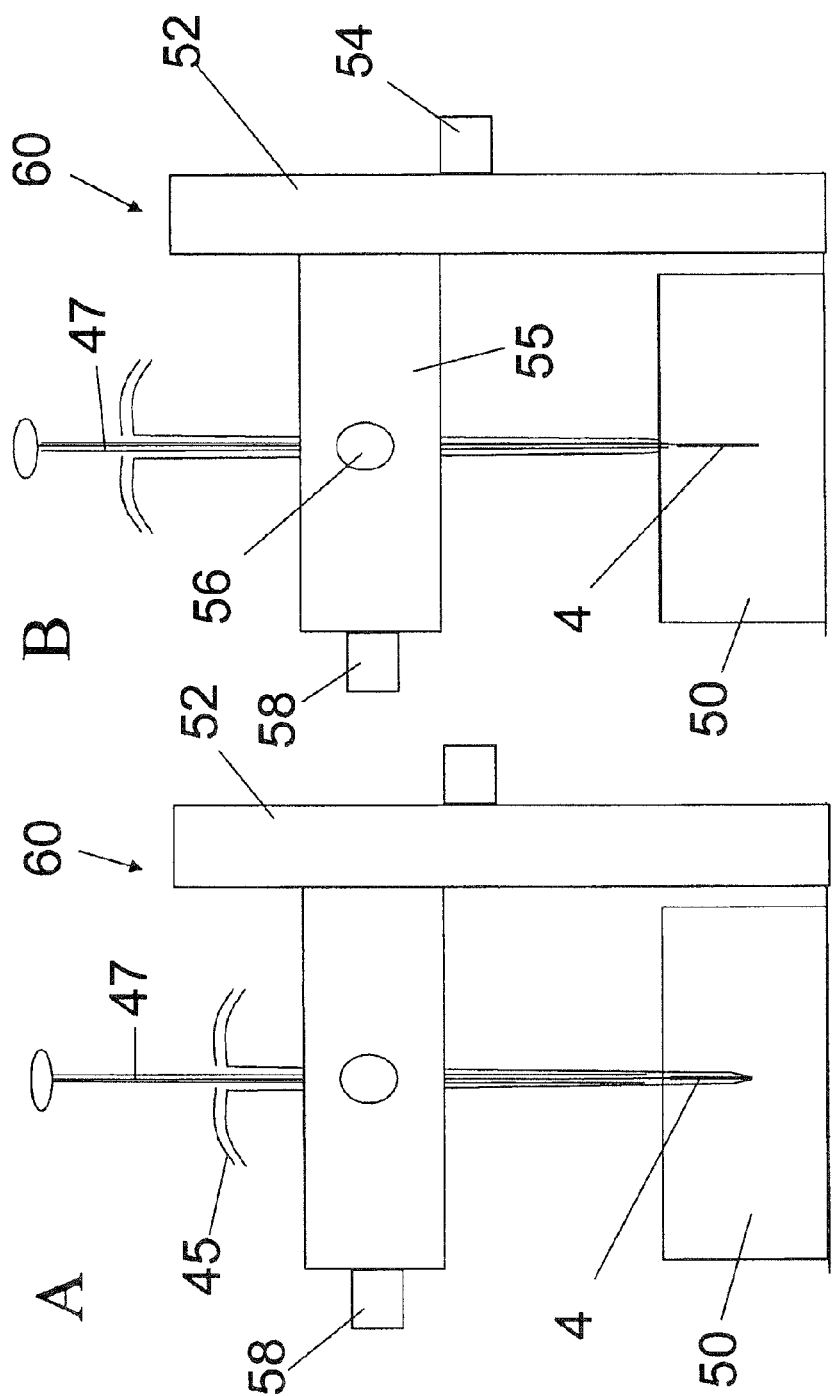
FIG. 7 shows a schematic of use of soft tissue sampling housing to position device for sampling with x-y-z stage.

FIG. 7 illustrates the housing 45 and extraction device mounted in the x-y-z positioning device 60 consisting of the "z" vertical positioning stage 52 with high resolution dial 54 and the x-y stage 55 with appropriate dials 56 and 58 allowing precise positioning of the extraction phase 4 within the sample 50. This positioning system is typically with microscope to monitor insertion and sampling process. The housing is first used to prepare a channel for the device at the required position for sampling (FIG. 7, part A). The housing is then withdrawn slightly while the extraction device 47 is held still. In this way the extraction phase of the device comes into contact with the tissue surrounding the channel prepared by the housing, thus avoiding a plug of tissue from traveling into the housing, and avoiding having the extraction device itself have to bore the channel in the tissue. In this case the device is used to monitor the concentrations of chemicals in the interstital or intracellular fluids in the tissues, as it would not sample chemical that is bound to tissue proteins or membranes. This would be preferred to tissue biopsy both in terms of the simplified sampling and reduced tissue damage.

Figure 8:
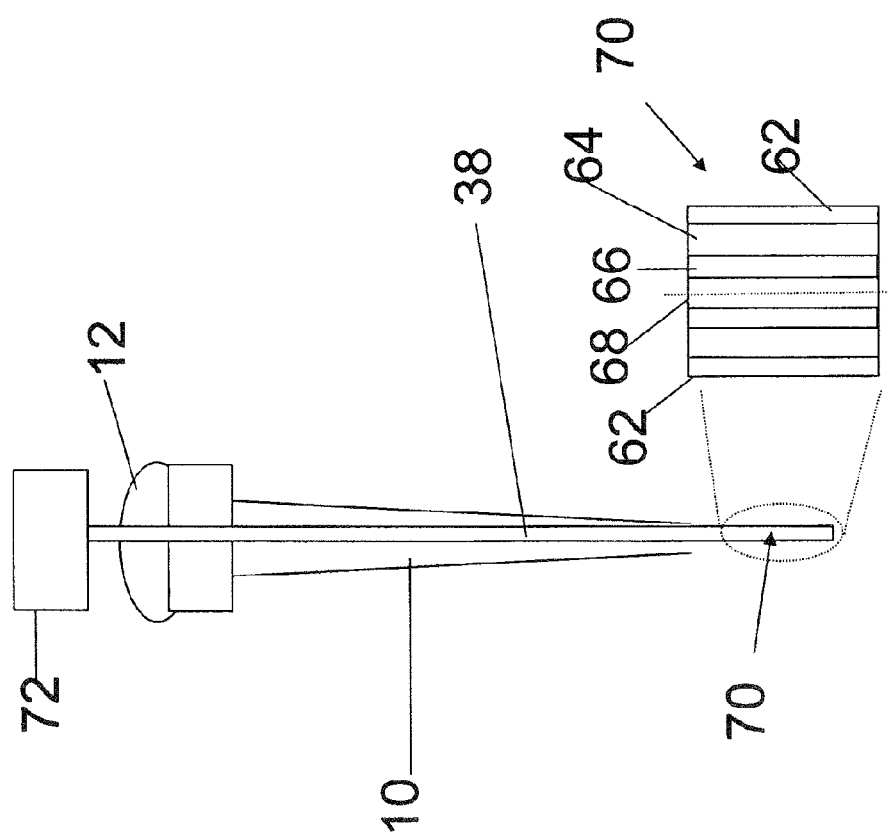
FIG. 8 illustrates a device according to an embodiment of the invention with hollow fibre with inner coated surface with catheter positioning device.

FIG. 8 shows the catheter with the hollow fibre 38 coated on the inside wall surface at the lower portion 70 of the fibre. The schematic cross sectional view shows the two layer coating 66 ad 64 on the inner fibre surface 62. The outer coating 66 is chosen to be biocompatible to eliminate absorption of proteins, while the inner coating 64 is the extraction phase facilitating removal of well defined components from sample introduced to the inner fibre via channel 68. The sample is drawn into the hollow fibre by using the device 72 generating pressure differential, such as syringe or metering pump connected to the hollow fibre. The action of drawing and ejecting sample produces agitation and therefore accelerate the extraction rate. The tubing is mounted in catheter, but can also be mounted in a positioning device illustrated in FIG. 7.

Figure 9:
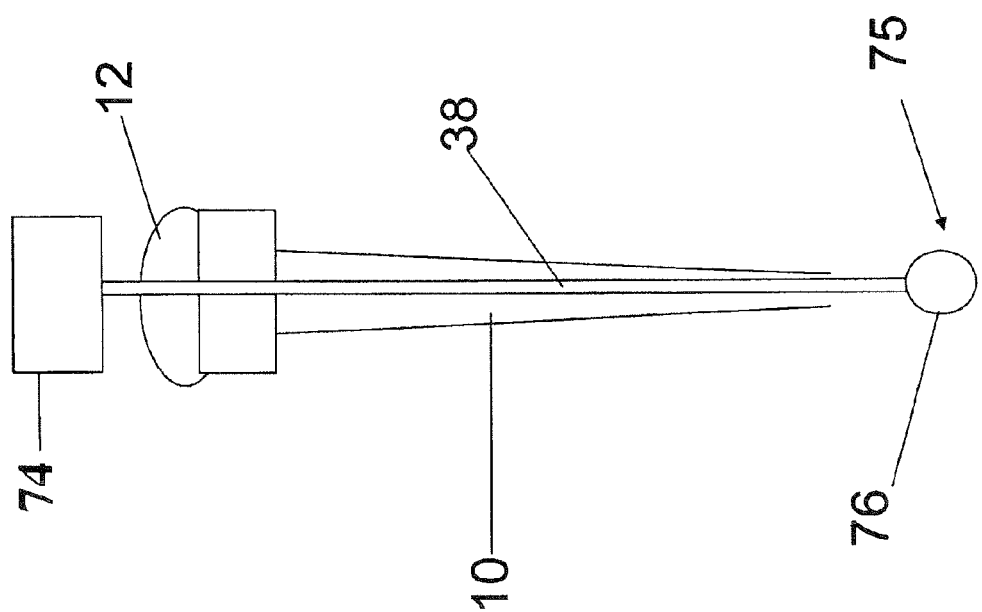
FIG. 9 illustrates a device according to an embodiment of the invention with hollow fibre sealed at one end with flexible extraction phase.

FIG. 9 shows the catheter with the hollow fibre 38 and stretchable coating sealing one end that can be blown out forming a small balloon structure 75 using the pressurized gas delivery device 74, such as small compressor or cylinder with carbon dioxide and micro-regulator connected to the free end of the hollow fibre. The material of the coating or its modified surface 76 can be designed to extract compounds from sample. The expended coating has higher surface area resulting in extraction rate enhancement. In addition repeated expansion and retraction of the coating cause induction of the convection currents and further increase in the extraction rate.

Miniaturization

While the device described is quite small (127 μm diameter), further miniaturization would be beneficial, particularly for the study of single cells. As probe size is reduced, the effect of the size of the theoretical boundary layer around the extraction phase on the rate of extraction is diminished, as is the case with microelectrodes (Heinze, J. *Angew. Chem. Int. Ed. Engl.* 1993, 32, 1268-1288.). In practical terms, this means the degree of convection in the sample has less effect on the rate of extraction. This is important for sampling of any system where static extraction must be conducted, as it would in single cells, or where degree of agitation is variable as it is for intravenous sampling. In addition, the dimension of the extraction phase also impacts extraction equilibration. Thinner extraction phases equilibrate faster and are less dependent on sample convection. Devices with overall dimensions in the range of 1-10 μm would be suitable for monitoring the interior of single cells while devices in the sub-micron range would be useful for monitoring organelles within cells. There are currently no feasible means to accurately assess chemical concentrations occurring within cells. All currently available methods either require that the cell is killed (eg. cell lysis followed by CE of cytosolic components in microchannels), which may produce an erroneous result, or suffer from poor accuracy (fluorescence tagging of specific compounds). The main strength of the coated fibre technology is that it can monitor cellular process in a non-disruptive manner. Only a negligible portion of the chemical is removed, allowing cellular processes to continue unperturbed. Commercially available micropositioning devices using x-y-z stage coupled to microscope can be used to position coated end of the fibre in the well defined part of the investigated system.

Technology that has been developed for genetic manipulation of cells uses fine capillaries to sample and introduce genetic material in cells, controlled by micromanipulators and monitored by stereomicroscopes. Cells are maintained in isotonic environments during the manipulations, typically by being contained in dishes or vials filled with suitable buffers. Similar instruments could be employed for positioning and sampling cells with fibre probes.

Portable Automated Sampling

Because the device and process described simplifies sampling and sample preparation significantly, it provides the opportunity for automated sampling of tissue concentrations without the need for continual human involvement. In on-line microdialysis sampling an animal being monitored is tethered to a stationary support and tubing conducting fluid to and from the microdialysis cannula and analytical instrument (CE or LC) is included in the tether. In the embodiment, an animal being monitored does not need to be tethered, but rather can carry a device for automatically moving probes in and out of a catheter, cannula or other sampling port at prescribed times. After sampling the device would hold the probes for retrieval and quantification at a later time. This embodiment would have similar advantages to the microdialysis system in terms of reduced human intervention and hence reduced sampling errors, with the additional advantage that animals in a study would be less restricted and stressed, and experiencing a more normal environment. This would reduce stress impacts on the integrity of the results.

Strategy of Single Use Devices

Up to now SPME devices have been designed to be re-used numerous times. While it is possible to re-use the polypyrrole coated fibre (wire) device described above, it is advantageous that this device be employed as a single-use device. Particularly in implementations where the device is exposed to blood, it would not be practical to clean the device and associated housing sufficiently for re-use. The goal of manufacture should be to minimize cost so that users find it cost-effective to dispose of the device after use.

Coating Strategies

There are a number of additional coating strategies that would be desirable in the design of these devices, under certain circumstances. These would extend the usefulness of the devices for the purposes described and allow them to be applied for additional purposes.

Improved biocompatibility in the extraction phase would be beneficial to extend either the time period the phase can be in contact with tissues, or increase the number of samplings that can be made from one site. This can be achieved in two different ways. Either new phase with better biocompatibility could be selected or a biocompatible outer layer could be used in conjunction with an inner extraction phase having lower biocompatibility.

Polypyrrole itself has good biocompatibility. It has been used for several years in biosensor devices without any evidence of toxicity, immunogenesis (initiation of an immune response) or thrombogenesis (initiation of clotting response). It is an example of an extraction phase that is suitable for exposing directly to the investigated system. If it is desirable to use a less biocompatible extraction phase the device could be rendered biocompatible by coating the extraction phase with an outer biocompatible layer such as derivatized cellulose. Analytes of interest would diffuse freely through this outer layer and be extracted by the extraction phase on the inner layer. This may be useful if more traditional extraction phases such as poly (dimethylsiloxane), polyacrylate or poly (ethylene glycol) are of interest for extractions.

Biorecognition entities that either comprise the extraction phase or are immobilized in another phase having low extraction affinity could provide both higher selectivity and higher sensitivity in these analyses. Higher affinity would provide higher sensitivity and more easily allow for shorter probe residence times. Higher selectivity would allow for reduced disturbance of the system under study, further enhancement of sensitivity and reduced concern for competition in extraction. This would permit the quantitative analysis of one compound present at low concentration when a competing compound is present at high concentration.

Biorecognition in the extraction phase may be accomplished by entrapment of antibodies or another molecules capable of biorecognition in an inert biocompatible extraction phase. This is demonstrated this in the use of polypyrrole to entrap antibodies specific for diazepam.

Figure 10:
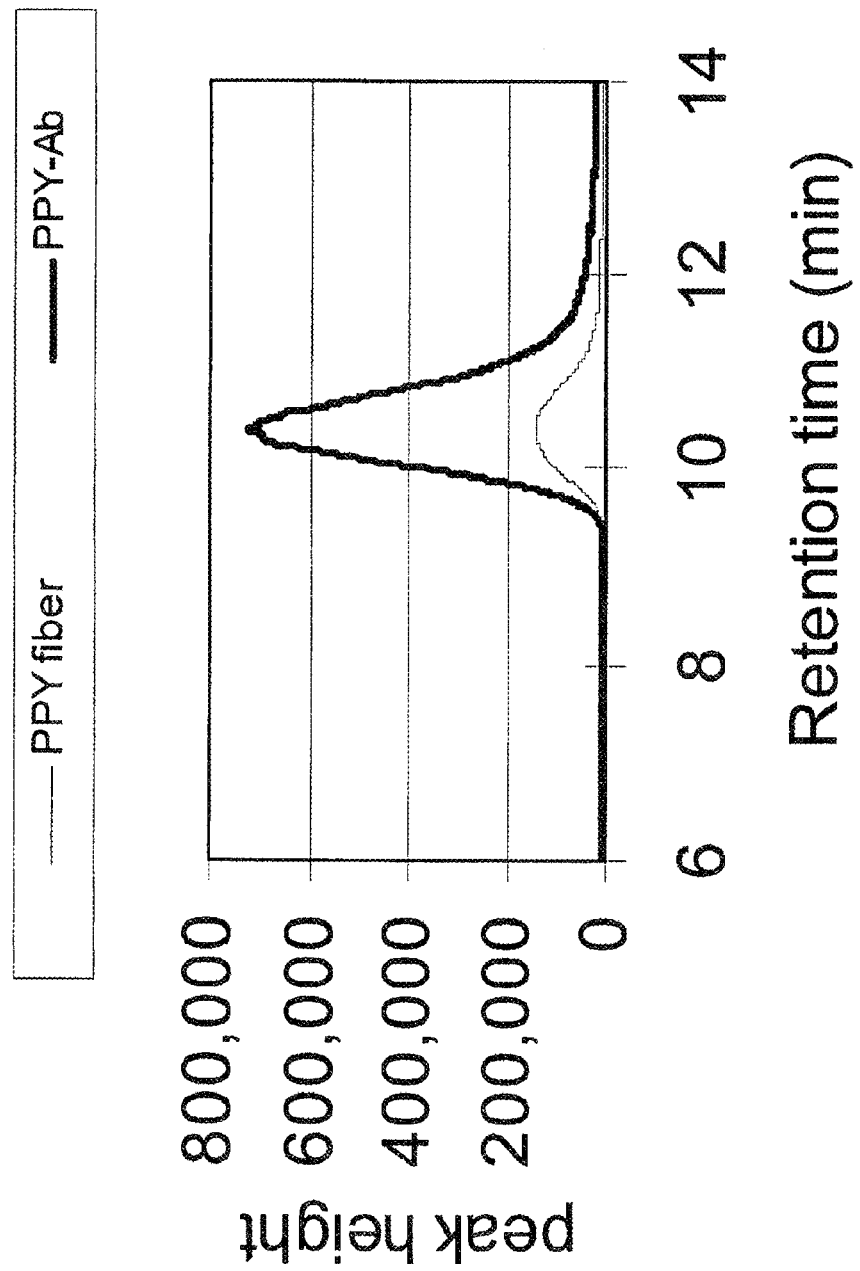
FIG. 10 shows a chromatogram comparing diazepam extraction from fibre with polypyrrole only versus fibre with anti-diazepam antibody entrapped in polypyrrole.

FIG. 10 shows a chromatogram comparing extraction of a sample containing diazepam, with a device with polypyrrole only, versus a device with entrapped anti-diazepam antibody. In this case the analyte affinity to the antibody is much higher than it is to the polypyrrole. Alternatively antibodies, nucleic acids or other molecules may be covalently attached to the fibre using typical immobilization strategies or they may be electrostatically immobilized by means similar to the immobilization of nucleic acid to nitrocellulose used in current blotting technologies. For covalent immobilization either random or oriented strategies may be used in one application or another.

Figure 11:
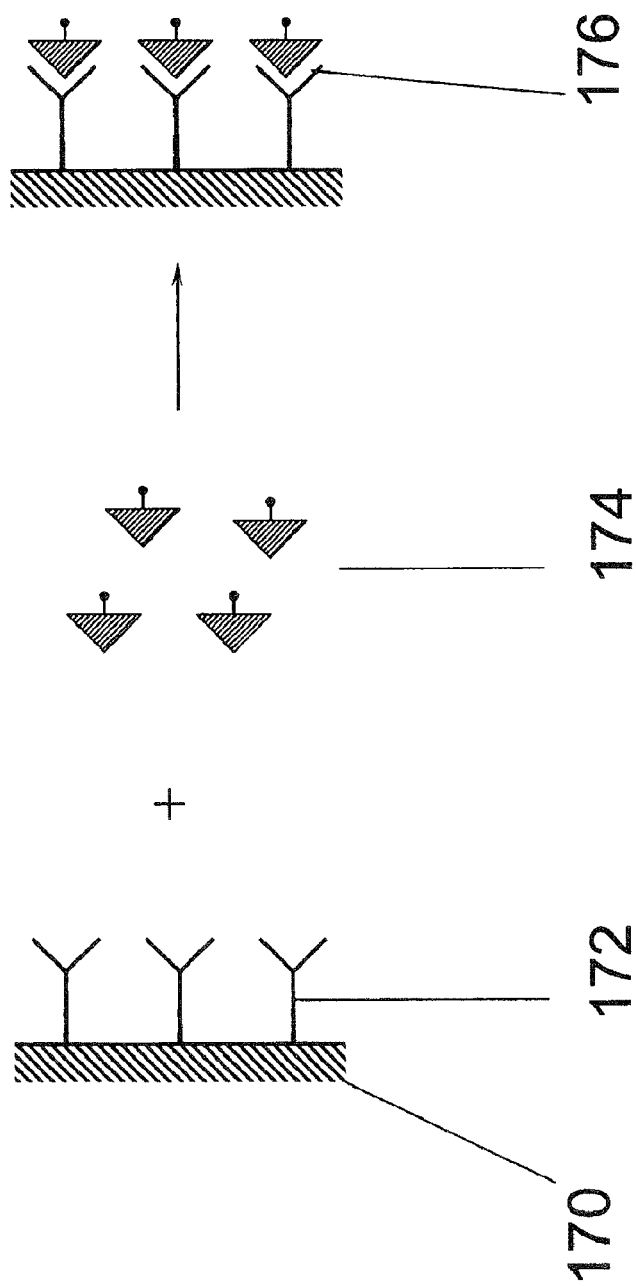
FIG. 11 illustrates selective extraction of diazepam using anti-diazepam antibodies immobilized on surface.

FIG. 11 shows a schematic of the oriented immobilization of antibody 172 on a surface 170, and attraction of antigen 174, to form an antibody-antigen complex 176. The diazepam may be liberated from the complex for quantification by temporary or permanent denaturation of the antibody protein.

If a probe with very high selectivity was developed, it could potentially extract only the compound of interest, which would eliminate the need for chromatography in the analysis. Direct introduction to a mass spectrometer for quantification would further simplify the analytical process. Such entities may include antibodies or antibody fragments, proteins, protein subunits or peptide sequences, DNA, RNA or polynucleotides or the antigens or substrates that bind with any of these. Such biorecognition entities may be immobilized by adsorption, electrostatically, covalently or by entrapment within another matrix. Covalent immobilization may be by either random or oriented means.

Biorecognition may also be achieved by using molecular imprinted polymers. In this case a polymer is prepared in the presence of the analyte of interest. The polymer contains functional groups that interact electrostatically with the analyte. After polymerization the analyte is removed and cavities remain in the polymer, with appropriate functional groups located inside. When used for extraction, analyte freely soluble in the sample is attracted to the cavities and held there by electrostatic forces. These polymers are seen by some as synthetic antibodies due to their high selectivity for the analyte of interest. Such polymers provide enhance selectivity when used as extraction phases in devices according to the invention.

It is also possible to prepare a coating that can have its extraction efficiency gated or activated just prior to extraction. This would allow for the pre-positioning of the device in a specific site, and then activate the extraction phase just as extraction is to start. Because polypyrrole is a conducting polymer, this may be accomplished by applying a small charge to the fibre. This is useful for the extraction of ionic compounds through controlling of the oxidation state of the polymer. Alternatively this may be accomplished using the device shown in FIG. 8 for soft tissue sampling. The device could first be positioned in the desired location, but the exposure of the fibre to the tissue could be delayed until the proper time to initiate sampling.

Use of Indicator Compound

A common and valuable tool in bioanalytical analysis is the monitoring of the appearance or disappearance of an indicator compound that is specific for a biochemical pathway. This is used for instance to monitor for the presence of specific cells or bacteria, or for the presence of free enzymes. In the typical chemical reaction a substrate (S) is transformed into a product (P) by interacting with a single enzyme or an enzyme system with associated cofactors. Enzymes may or may not be transformed in this process. The indicator may be the substrate, in which case its disappearance is monitored, or it may be the product, in which case its appearance is monitored. The amount of indicator formed in a specific time is correlated to both the amount and activity of the target enzyme present. If the indicator has an affinity for the extraction phase, enzyme activities and/or metabolic rates may be monitored in situ. The substrate may be either loaded onto the fibre or placed into a cell suspension or enzyme solution. When the fibre is placed into the solution, indicator will become immobilized in the fibre, and can be subsequently quantified by an analytical instrument.

Pre-Loading of Fibre with Calibrant

For conventional SPME analysis, a common difficulty is in devising accurate means of quantification. For in vitro analysis quantification is often achieved by adding a known amount of standard to the sample, and then performing the analysis. This is referred to as calibration by internal standard or standard addition. The amount of the standard recovered is assumed to be correlated with the amount of unknown analyte recovered and the ratio is calculated in order to determine the original concentration of unknown. For in vivo and in situ analysis it is typically not practical to add a standard to the system under analysis. Until now the most practical means of calibration is by preparing a series of synthetic standards that match the sample as closely as possible, and comparing the results from the standards analysis with that of the unknown. This approach was described above for the calibration of polypyrrole devices in the in vivo pharmacokinetic study with reference to FIG. 12. In this case whole dog blood was obtained from a commercial supplier and samples were prepared with various drug concentrations. Upon analysis a calibration curve is constructed and this curve is used to interpolate unknown detector responses to estimate unknown drug concentrations. While the method is conceptually simple, it is not always highly accurate as it cannot accommodate the impact of slight changes in the in vivo site for impact on the results.

As an alternative to conventional internal standard calibration, a standard may be loaded onto the fibre (extraction phase) prior to analysis and the loss of standard from the fibre is monitored instrumentally. Where the kinetics of absorption of the internal standard analyte to the fibre is equivalent to the kinetics of desorption (binding is reversible), absorption and desorption are controlled by diffusion in the sample and the rate of loss of standard from the fibre will be correlated with uptake of analyte by the fibre. The amount of analyte lost may be correlated with the amount absorbed, and consequently with sample concentration of unknown also. Using this strategy variation in sample convection may be controlled for by referencing unknown analyte to the amount of calibrant lost from the fibre. Alternatively, where the convection conditions and hence rate of mass transfer and are known or controlled, the use of an irreversibly bound calibrant on the fibre may be used. The fibre would first be exposed to a matrix-matched standard with a known concentration of analyte. The fibre would subsequently be exposed to the unknown sample. The ratio of unknown to standard extracted by the fibre would accurately reflect the ratio of unknown to standard sample concentrations. (G. Xiong, Y. Chen and J. Pawliszyn "On-site calibration method based on stepwise solid-phase microextraction", *J. Chromatogr.* A 999, 43-50 (2003)).

Pre-loading of compound onto the fibre may also be used for calibrated delivery of compound to a precise tissue region. Where the compound pre-loaded has low to moderate affinity for the fibre, compound will partition out of the fibre and into the surrounding tissue during exposure. This may be used as a means of dosing only one targeted tissue region with a drug or other compound of interest, avoiding dosing of the whole animal as is commonly the case in therapeutic drug regimens. Tissue dosage control may be attained by precisely controlling the exposure time. Dosage may then be confirmed by desorbing remaining analytes into an analytical instrument to quantify the amount remaining, allowing the calculation of the amount delivered.

An exemplary use of calibrant is discussed below with reference to Example 4.

Standards in the Extraction Phase

Internal standard and standard addition are important calibration approaches, which are very effective even when quantifying target analytes in complex matrices. They compensate for additional capacity or activity of such a matrix. However such approaches require delivery of the standard to the matrix. This adds additional steps to the sample preparation, which makes the process longer and is sometimes prohibitive, for example in the case of on-site or in-vivo determinations.

According to an aspect of the invention, an alternative approach may be used where the standard is delivered together with the introduction of the extraction phase. This approach is not practical to implement for exhaustive extraction techniques, since large volumes of the extraction phase having a high affinity for the target analytes are used in these approaches to facilitate as complete removal of the analytes from the matrix as possible. However, in microextraction a substantial portion of the analytes is present in the matrix during the extraction and after equilibrium is reached. This presents an opportunity to add the standard to the investigated system together with the extraction phase. For example, when performing small volume (a few mL) sample analysis involving microextraction step, as is frequently the case with automated analysis, placing the extraction phase/standard mixture in the vial with the sample can be combined with addition of a standard. In this way, the step of spiking the sample with a standard is eliminated.

Desorption and re-equilibration of a standard originally present in the matrix can occur simultaneously with the mass transfer and equilibration of the target analytes from the matrix to the extraction phase. Thus, the standard delivery process according to this aspect of the invention does not add substantially to the extraction time. For example, in automated fiber SPME analysis the standard can be introduced onto the coating during an automated analysis process by exposing the fiber to a vial containing the standard. Alternatively, multiple fibers containing standards can be used each for single analysis. In addition, the standard can be generated in or released from the coating by way of a chemical reaction in the coating.

A significant impact of the standard in the extraction phase approach for calibration would be realized for on-site, in-situ or in-vivo investigations. However, it is desirable to minimize the amount of foreign substances added to the investigated system. For this reason, direct standard spike into the matrix is typically not possible. Full re-equilibration of standards present on the fiber is frequently not feasible because of the potential for contamination and large dilution which could occur in on-site investigations. However, successful calibration can be accomplished by investigating kinetics of the desorbtion/sorption process. Since the rate of extraction for most practical types of extractions is controlled by mass transfer through the boundary layer, the desorbtion rate or the standard can be used as an indication of the extent of the boundary layer (existing either in the matrix or in the extraction phase, or both). This information can be used for calibration of the target analytes.

In an advanced approach, standards can be added to balance the analyte loss from the matrix during extraction, similar to methods which may be used in dialysis, in order to minimize the impact of standards on the investigated system. This objective may be accomplished by adding the same amount of the standard as the amount of analyte being removed from the matrix. The standard chosen may be an isotopically labeled analog of the target analyte, in order to minimize impact on the investigated system. In addition, this approach can allow study of the physicochemical partitioning and adsorption phenomenon among sample matrix components.

When employing a standard in the extraction phase, calibration can be accomplished in any microextraction or steady state approach including Solid Phase Microextraction (SPME), micro liquid phase extraction (MLPE), and membrane extraction or headspace extraction. In SPME, a standard can be used to dope the solid/polymeric extraction phase. In MLPE, a standard would be present in the liquid extraction phase. In membrane extraction, the standard would be present in the striping phase and in headspace extraction in the gaseous headspace. In some cases the standard can be delivered by other components of the extraction system. For example, in the fiber SPME the standard can be delivered from a needle by first sorbing the standard onto the needle material. Also the standard could be delivered together with the vial, for example by including the standard on or in the wall of the vial.

An exemplary use of calibrant is discussed below with reference to Examples 6, 7, 8, 9, 10 and 11.

Use of Multiple Fibres

The development of multiple fibre coating strategies has several benefits. In addition to providing more flexibility in selecting devices for a particular application, multiple devices could be used in parallel to provide for a more complete profiling of the types and amounts of compounds present in a sample. This may be accomplished either by exposing multiple fibres to a sample in parallel, or by preparing one fibre with multiple sorbents.

Fibres for Conducting Micro-Chemical Reactions

On-fibre reaction can significantly enhance the detection of components of interests. For example on-fibre fluorescence labeling has been has improved detection limits for detection of toxins at trace level (A. Namera, A. So, J. Pawliszyn "Analysis of Anatoxin-a in Aqueous Samples by Solid-Phase Microextraction Coupled to High-Performance Liquid Chromatography with Fluorescence Detection and On-Fiber" Derivatization *J. Chromatogr.* 963, 295-302 (2002)). Two of the most important chemical reactions for molecular characterization in genomics and proteomics research are DNA amplification and enzymatic protein digestion. Both processes are enzymatic reactions that are conducted in vitro, with the products either being carried on to a further processing step or analysed directly.

In DNA amplification a small number of DNA or polynucleotide fragments are amplified by the enzyme DNA polymerase. Through the action of the enzyme and suitable substrates, the copy number of DNA fragments can be increased exponentially in just a few hours. The process is characterized by high fidelity so that the end product is a very pure solution of identical DNA fragments. Typically the amount of DNA originally present is insufficient for further processing and/or analytical characterization whereas the concentration in the final product is sufficient. The product may either be characterized for nucleotide content and sequence or used for the preparation of peptides or proteins coded by the DNA sequence.

For enzymatic protein digestion a protein sample is digested by enzymes that cleave the polypeptide chains at specific sites. The resulting polypeptide fragments may be characterized for molecular weight or peptide content and sequence. Typically the intact protein is too large for direct characterization and so a protein is characterized by a 'fingerprint' analysis of the pattern of polypeptide fragments produced by one or more enzymatic cleavages. Alternatively the polypeptides may be sequenced and the sequence of the original protein reconstructed. This allows for example, that the DNA sequence coding for the protein may be determined either for the purpose of identifying its location in the genome or for development of an expression system to produce the protein in quantity.

With the continued miniaturization of genomic and proteomic analyses through the use of micromachined or µTAS devices, there is a need to miniaturize the sample preparation and introduction steps that come up front. These types of miniaturized analyses are increasingly important in the fields of genomics and proteomics where sample sizes are small due to the high cost of these samples. Also the miniaturization allows for parallelization and higher throughput in analysis to more efficiently process the very large number of samples made possible by the completion of the human genome project. A porous polymer attached to a fine fibre or wire makes an ideal medium in which to conduct these enzymatic reactions in miniature scale, with the added advantage that when the reaction is complete, the device is also suitable for introduction of the reaction products directly to a microanalytical system.

Interfaces

As described above one of the strengths of the device and process described is that once sampling and sample preparation (pre-concentration and elimination of matrix) have been completed, the device of the instant invention is ideally suited for directly introducing the extracted analytes to an instrument for separation and quantification.

Conventional SPME devices are interfacing to GC or LC equipment for quantification of amount of compound extracted. In the case of GC equipment the fibre is desorbed in the heated injection sleeve similarly to the way a conventional syringe injection is conducted. Analytes for GC analysis are necessarily volatile at the temperatures normally used in a GC injector and are efficiently desorbed in the hot carrier gas flowing through the injection sleeve and into the separation column. Compounds analysed by LC are typically non volatile and/or thermally unstable and so heat cannot be used for desorption. For LC desorption a dedicated interface is required to first remove analytes from the fibre and transfer them to a solvent. A portion or all of this solvent is then injected into the instrument for analysis. In the commercial interface the fibre is desorbed in a solvent filled chamber in a valve connected to the instrument inlet. After desorption the valve is switched in line with the pressurized solvent flow of the instrument and the entire volume of the desorption solution with dissolved analytes is introduced to the instrument.

Modification for Efficient LC Quantification

Figure 13:
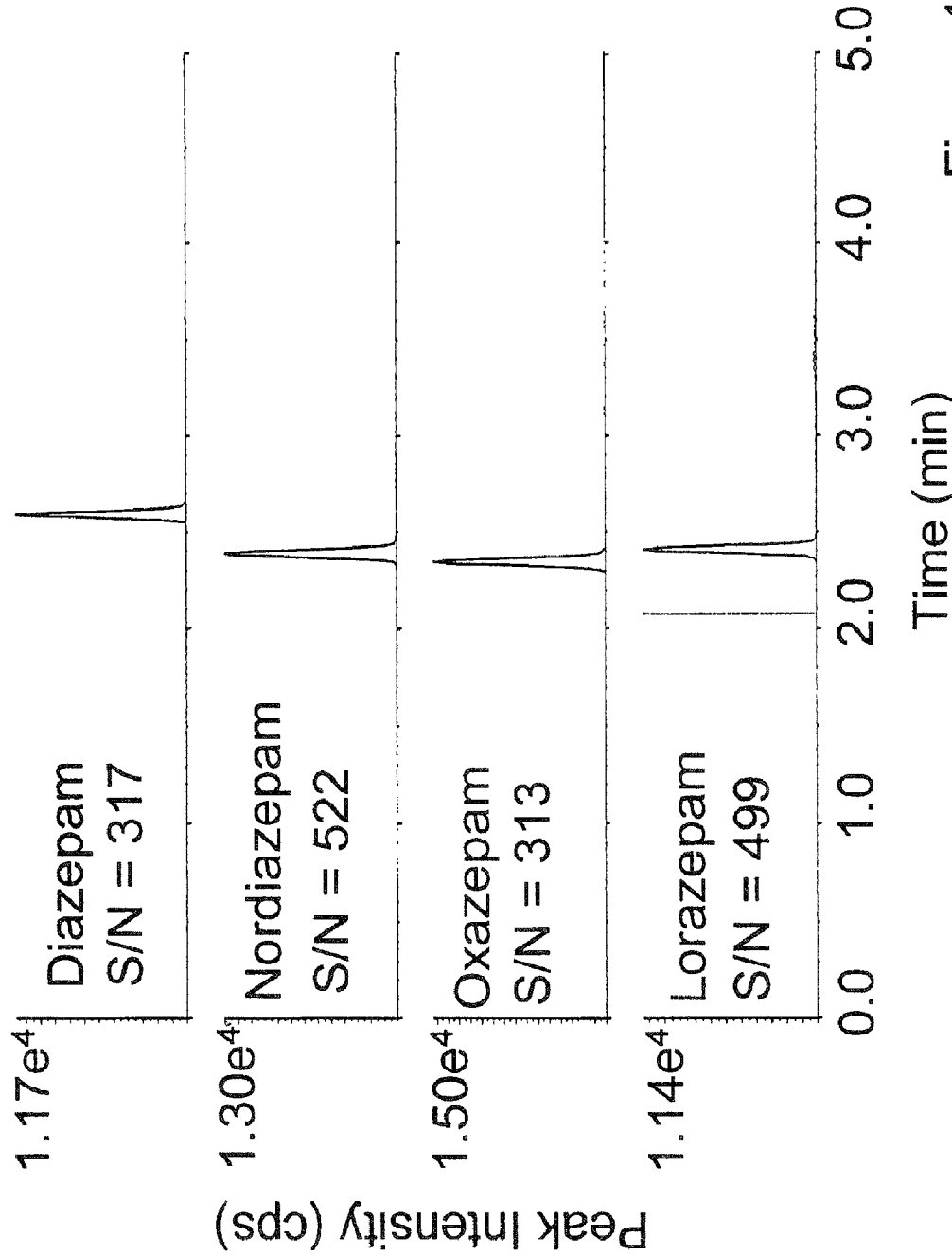
FIG. 13 illustrates an example chromatograph obtained after LC/MS/MS quantification of device extraction from plasma.

The technique has been limited by the relatively large volume of the commercial desorption interface (100 µL). Because of the phase thickness of the commercial SPME devices for LC (ca. 50 µL) this large volume is required. If desorption volume is reduced a significant proportion of the analytes are not removed from the fibre. Carryovers in the range of 20% are common (depending on the specific analyte and desorption solvent used) as the volume of desorption solvent is reduced below 50 μL. These volumes, however, are too large for typical LC applications as injection volumes are in the 10-20 μL range, particularly for LC/MS applications. Large injection volumes in these analyses typically produce unacceptably broad chromatographic peaks and poor resolution. When only a small portion of the total desorption solvent is injected, inferior sensitivity results. One strength of device of the instant invention is the ability to introduce all of the extracted analyte to the instrument for quantification. This allows for maximal sensitivity. Fibres with significantly reduced phase thicknesses, such as the polypyrrole coated wire described for the pharmacokinetic analyses, may be efficiently desorbed in 10-20 μL of desorption solvent. The entire desorption volume may then be injected for quantification. The result is sharp, symmetrical peaks as are shown in FIG. 13, which may be accurately integrated and produce good chromatographic resolution.

The foregoing described the use of static desorption, but dynamic desorption of analytes is also of interest in certain applications. This is achieved by passing desorption solvent over the fibre during desorption. Because the fibre is continuously exposed to fresh desorption solvent, quantitative desorption is theoretically possible. The rate of desorption is governed by the rate of solvent flow over the fibre. Faster flow results in faster desorption. To achieve the fastest desorption possible and to avoid ending up with an overly large solvent injection plug, it is necessary that the inner diameter of the desorption chamber is as small as possible. When volumetric flow is constant, faster linear flow is achieved in a smaller diameter chamber. This results in a shorter desorption time and hence a minimized total desorption volume.

Automation of LC Quantification

While the reduced volume HPLC interface used to date allows for efficient transfer of analytes from the fibre to the instrument, the process is only partially automated. To date the introduction and removal of the probe wire to/from the interface must be performed manually for each injection.

Figure 14:
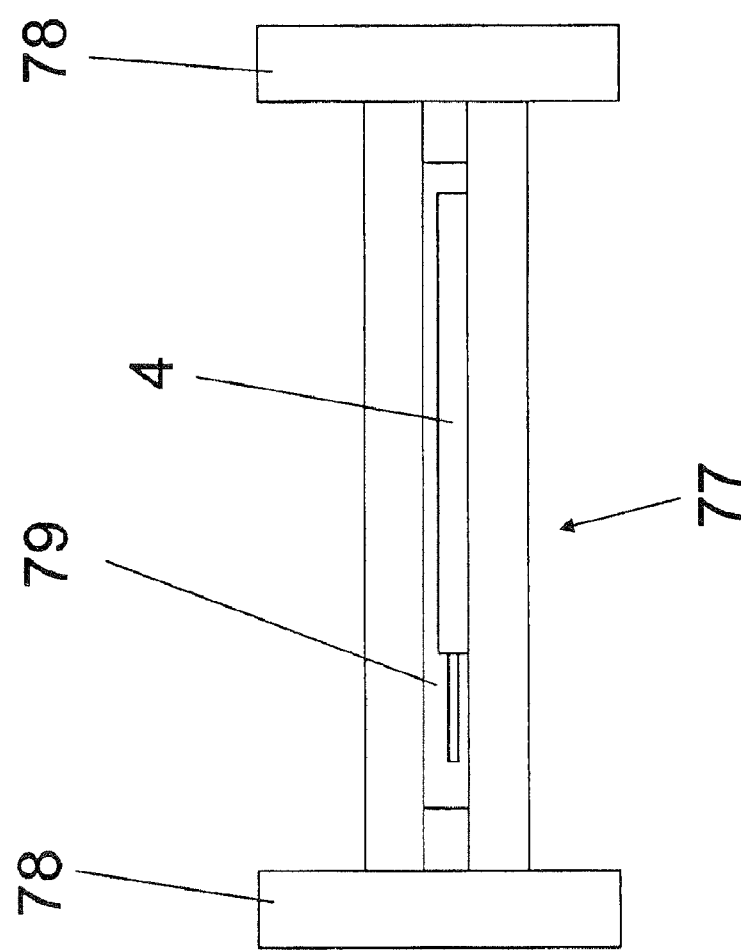
FIG. 14 shows a cartridge holding a fibre.

FIG. 14 illustrates a micro-cartridge 77, which contains coated piece of fibre in its small cavity 79 and sealed with plugs 78. The cavity 79 can be filled with desorption solvent. After extraction the coated piece of fibre containing the coating 4 is placed in a cavity 79 of the cartridge 77 for protection during storage and transport. Determination of extracted components can be performed in an automated instrument adopted for use with cartridges.

Interface for CE, Use of Electrokinetic Stacking

As discussed above, the device of the instant invention provides an ideal means for interfacing sampling and sample preparation to microanalytical instruments, particularly when devices much smaller than the commercially available SPME devices are employed. In capillary electrophoresis and related technologies, analytes are separated in a capillary typically 50 μm in diameter. This is too small for conventional syringe injection. Injection is typically by hydrodynamic or electrokinetic means. With hydrodynamic injection a sample is placed in the buffer reservoir associated with one end of the capillary. That end is then lifted above the opposite end by a prescribed amount for a prescribed time. The volume of sample entering the capillary may be calculated from the time, the elevation difference, the capillary diameter and the solution viscosity. The sample solution is then exchanged for running buffer solution prior to applying the separation voltage. While simple, the technique suffers from inaccuracies in injection volume and poor reproducibility from one analysis to the next. With electrokinetic injection a sample is again placed in the buffer reservoir associated with one end of the capillary. An injection voltage is applied across the reservoir and capillary and analytes in solution move into the capillary by electromotive force. Once sufficient material has been injected the voltage is removed and the sample solution is again exchanged for running buffer solution prior to applying the separation voltage. This method suffers from inaccuracy in injections due to the variation in electrophoretic mobility between analytes. This results in different amounts of the different compounds present being injected. A small diameter fibre with extracted analytes may be introduced directly inside a CE separation capillary filled with running buffer (Whang, C. W., Pawliszyn, J. Anal. Commun., 1998, 35, 353-356). This allows for accurate, quantitative introduction of analytes for separation.

As an improvement to this technique for CE analysis, by carefully matching the outer diameter of the fibre and the inner diameter of the separation capillary, a stacking of analytes occurs prior to separation results. This allows for much superior resolution. Electrophoretic velocity is inversely proportional to the cross-sectional area inside the separation capillary. When this area is reduced, increased velocity results because of an increase in electric field gradient. When a fibre is introduced inside a CE capillary, the space between the fibre and the capillary wall has a much smaller cross-sectional area than the space after the fibre where only buffer is present in the capillary. When a fibre is present and separation voltage applied, the analytes move out of the fibre and along the restricted channel quite quickly. When they reach the area of open capillary mobility drops significantly and the analytes are concentrated in a narrow band. During separation a higher resolution is achieved than would otherwise be possible.

Figure 15:
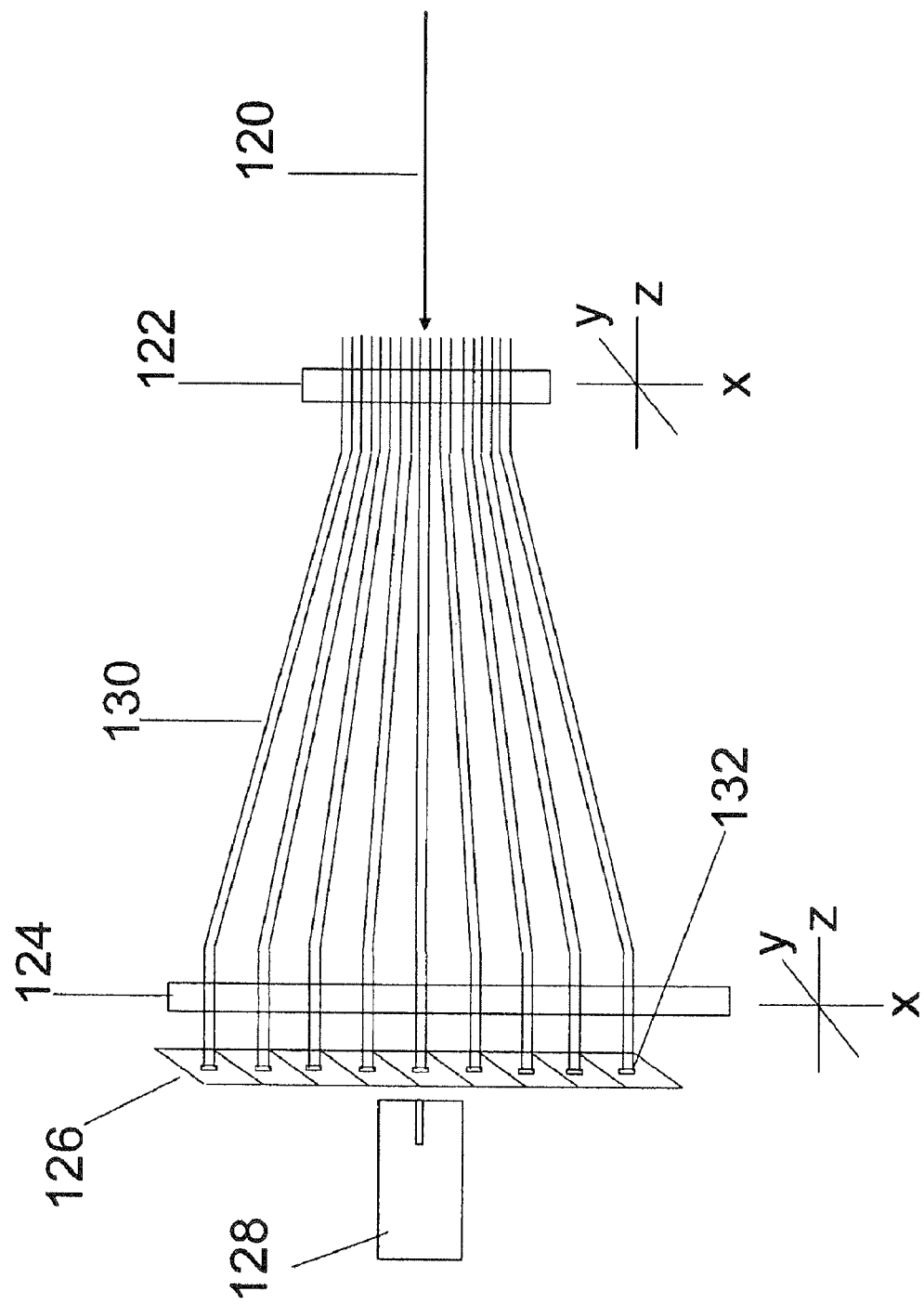
FIG. 15 is a schematic of batch process for parallel extraction and multiple MALDI desorption with positioning devices at both laser source and desorption ends of fibres.

FIG. 15 illustrates x-y-z positioning device for use with a fibre bundle. Individual fibres may be positioned precisely in the separation capillary prior to desorption. In this case the extraction phase would be coated on more than just the very tip of the fibre, as is shown in FIG. 15 (132) and desorption would be accomplished by applying an appropriate electric potential rather than by laser pulsing.

Direct Introduction to MS Through Nanospray Nebulizer

In some instances it is not necessary to chromatographically separate extracted analytes prior to quantification. This is the case where the fibre has very high selectivity such that only the analyte of interest is extracted with no interfering substances. It is also true where mass spectrometry is used for detection/quantification and components are separated by mass rather than by time prior to quantification. For MS applications it is possible to place the fibre directly into a nebulizer needle in an electrospray ionization source.

Figure 16:
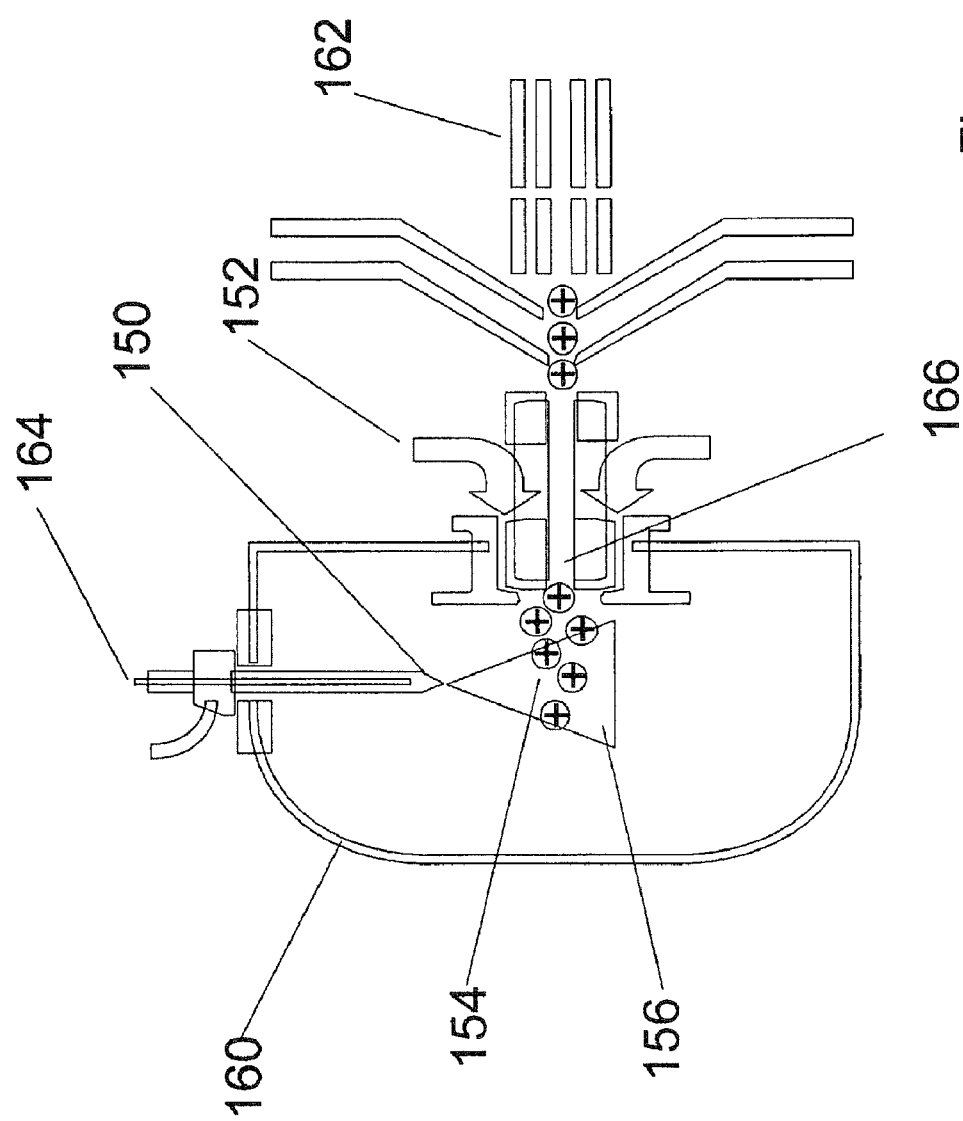
FIG. 16 is a schematic of the inventive device used with nanospray nebulizer and ESI MS.

FIG. 16 describes this process schematically. Solvent flowing through the nebulizer 150 efficiently desorbs analytes from the fibre 164 prior to being nebulized and sprayed in a plume 156 in a mass spectrometer atmospheric pressure ionization source 160. Ionization is then accomplished by standard ESI with MS detection, ie. droplets in the plume 156 are dried and reduced in size by hot gas flow 152 until ions 154 form in the vicinity of the orifice 166. These then pass into the mass analyzer 162 in the instrument.

Application to MALDI Analysis

Matrix-assisted laser desorption/ionization (MALDI) is a technique for ionization of molecules using a laser as the energy source. As a very soft ionization method, MALDI yields primarily the singly charged protonated molecule which are then conveniently quantified by either ion mobility spectrometry or time of flight mass spectrometry. This feature has made MALDI a widespread ionization tool for high molecular weight, nonvolatile and thermally labile analytes. MALDI has enabled the routine determination of large biomolecular such as peptides and proteins (P E. Jackson, P F. Scholl, and J D. Groopman, *Molecular Medicine Today*, 2000, 6, 271.)

The embodiment of the invention wherein the inventive fibre device is coupled to MALDI advantageously allows a combination of sample extraction with the ionization procedure on the very tip of a fused silica optical fibre for bimolecular analysis. The sample end of the fibre was coated for the extraction of peptides and/or proteins in a matrix solution. In the case of enkephalin and substance P the matrix used was alpha-cyano-4-hydroxy cinnaminic acid. The optical fibre thus served as the sample extraction surface, the support for the sample plus matrix, and the optical pipe to transfer the laser energy from the laser to the sample. Laser energy was transferred through the other end of the optic fibre to ionize and desorb the biomolecules for subsequent analysis. This fibre/MALDI combination was coupled with an ion mobility spectrometer and a tandem quadrupole/time-of-flight mass spectrometer (in separate experiments) for the detection of the MALDI signal.

Figure 17:
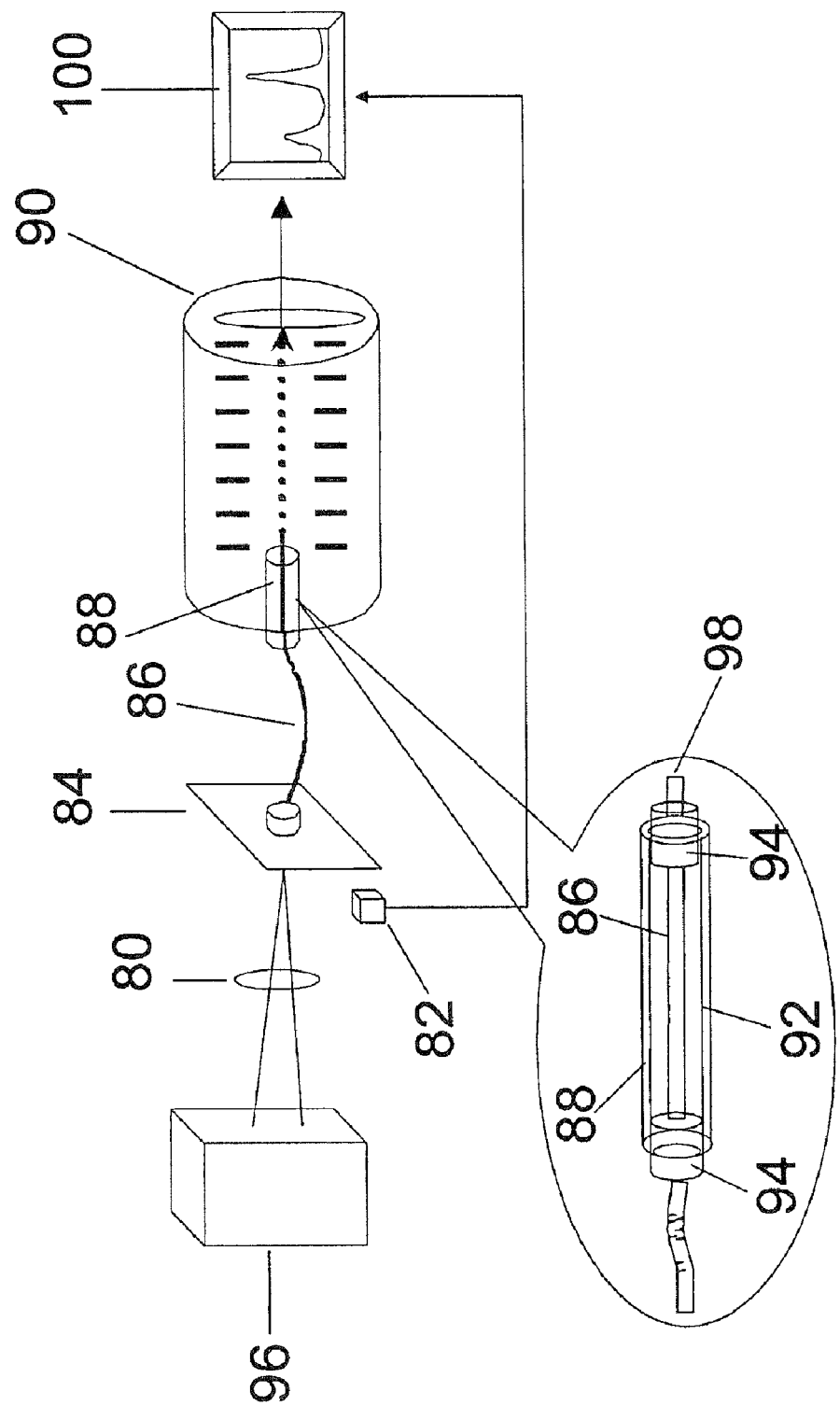
FIG. 17 shows a schematic of fibre/MALDI-IMS system according to the invention.

FIG. 17 shows a schematic of the fibre/MALDI-IMS interface and instrument. This consists of a laser source 96 and focusing lens 80, which focuses the laser light onto the uncoated end of the fibre, held in an x-y-z positioning array 84. The array movement may be manual or automated. The fibre 86 transmits light from the source to the x-y-z positionable inlet 88 of the mass analyser 90, which in this case was an ion mobility spectrometer. In the inlet 88 the coated end of the fibre 86 is held in place by two silicone septa 94 and a section of support tubing 92. Only the very tip 98 of the fibre is coated with extraction phase. A photosensitive diode 82 is positioned at the laser source 84 to sense the desorption laser pulse and initiate data collection 100.

Figure 18:
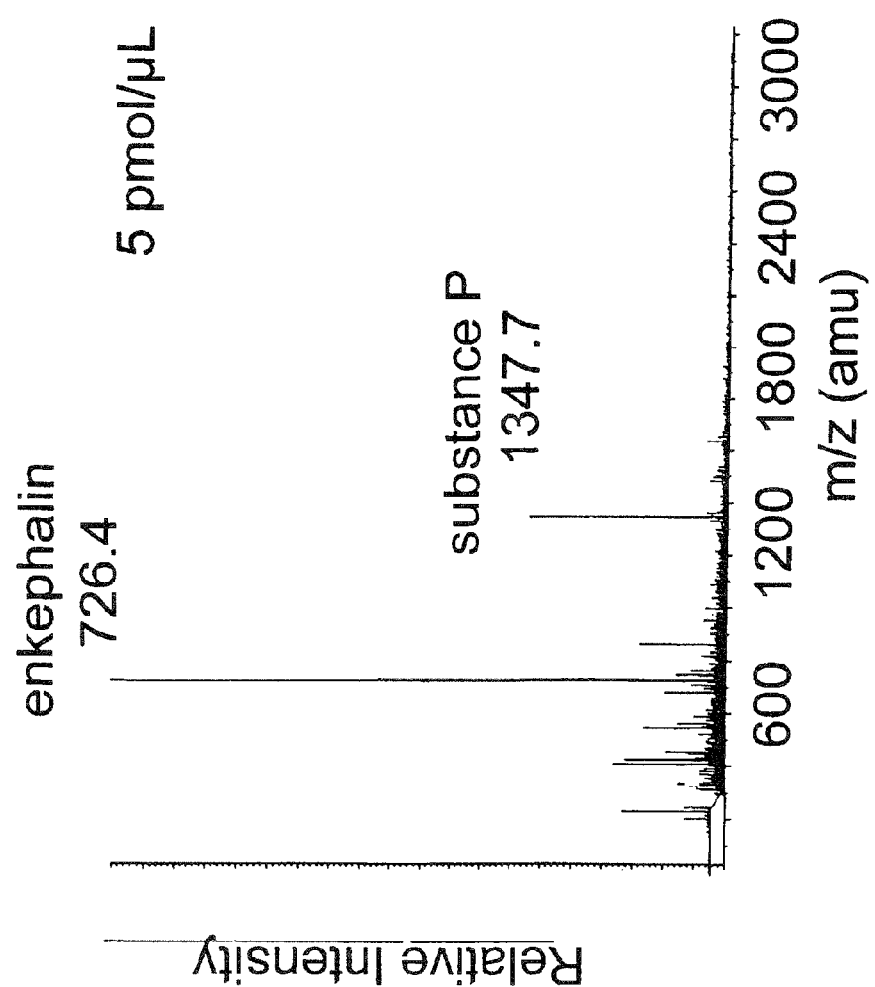
FIG. 18 illustrates an exemplary mass spectrum obtained from a fibre/MALDI-IMS system according to the invention

FIG. 18 shows the ion mobility mass spectrum of enkephalin and substance P were obtained using this system.

One advantage of the MALDI/IMS interface is that the MALDI source is operated at ambient pressure instead of high vacuum, as it is in conventional MALDI/TOF mass spectrometry. Also, loss of sample delivered to the drift tube is negligible at ambient pressure and it has been reported recently that atmospheric pressure MALDI produces a generally uniform ion cloud at atmospheric pressure. The ionization process is even softer than that of the conventional high vacuum MALDI and is capable of producing protonated molecular ions for small proteins. This is convenient for the MALDI analysis of macromolecules because of the relative absence of metastable fragmentation and discrimination in the ionization process compared to conventional vacuum MALDI. The most promising advantage of this ambient interface is the possibility of interchangeably using the same instrument for both electrospray and MALDI sample introduction.

Figure 19:
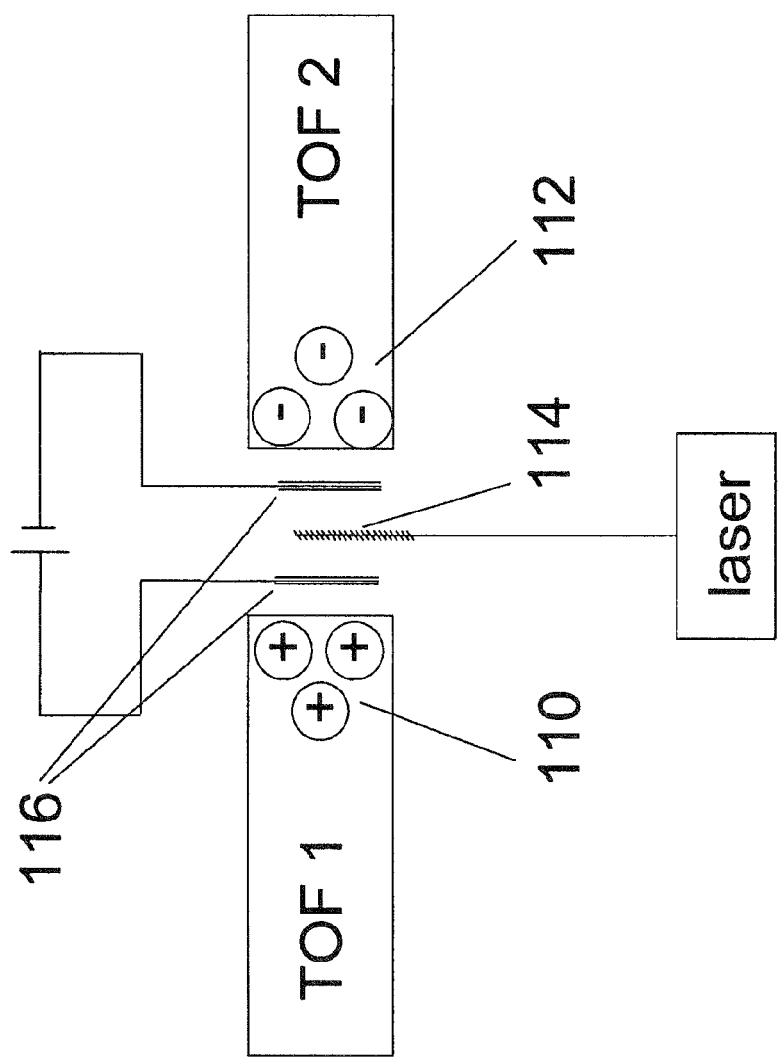
FIG. 19 is a schematic of a fibre/MALDI source.

FIG. 19 shows a schematic of the laser desorption interface an ion formation. In this case two time of flight mass spectrometers (TOF) are used, one to sample positive ions 110 and the other to sample negative ions 112. A laser pulse initiates desorption from the extraction phase 114 and polarized plates 116 accelerate the appropriate ions into the appropriate mass analyzer.

Though MALDI has enabled the routine determination of large biomolecules such as peptides and proteins, it has always been great interest to develop quantitative MALDI analysis. For quantitative work with conventional MALDI analysis, the laser beam is scanned cross the sample area on the target plate, and each sample spot is irradiated with multiple laser shots until a striking decrease in signal detection is observed which indicates the removal of most of the sample loaded on this particular spot. Therefore, tens to hundreds of laser shots must be fired to finish the scanning process, and the final spectrum is typically a sum or an average of all the spectra obtained from each laser shot. This sampling process will lead to the unavoidable poor shot-to-shot and spot-to-spot sample reproducibility, and has been considered as the fundamental limitation for method quantification in MALDI analysis.

The combination of the inventive device with MALDI has technically solved the above problem as it combines sample extraction with the ionization procedure on the tip of a fused silica optical fibre. The optical fibre thus served as the sample extraction surface, the support for the sample plus matrix, and the optical pipe to transfer the laser energy from the laser to the sample. Since the sample was loaded directly on the fibre tip, so the sample size was identical to that of the laser irradiance area and there existed no spot-to-spot desorption difference. In addition, due to the multiple reflections inside the fibre, the primary laser profile is converted into a homogeneous intensity profile at the sample end fibre surface. This means that laser emission is homogeneous through the fibre tip surface. The method was developed as to accomplish all sample desorption that was extracted on fibre tip with a single laser shot. As long as this situation could be satisfied, the spot-to-spot and shot-to-shot spectral disparity would also be minimized. In this way it dramatically improved the quantification aspect of MALDI as well as saved large amount of analytical time and analyte consumed. To explore the quantitative aspects of the fibre/MALDI method TOAB was selected as the analyte compound and all experiments were performed in the matrix DH B. The fibre/MALDI-IMS system described in FIG. 17 was used for quantification.

In the extraction step of the previous experiments, the tip of the fibre/MALDI fibre was dipped into the solution containing both sample and matrix. For this pre-mixed extraction method, the analyte to matrix ratio was pre-optimized and fixed for the best performance and this is almost impossible for the detection of analyte in real samples of unknown concentrations. Meanwhile, due to the very small capacity of the extraction phase, there exists a competition between the analyte and matrix that causes a further limitation for the amount of analyte that can be extracted. A more practical way is to load the matrix in a second step after sample extraction. Spray method with a nebulizer is an ideal candidate for this purpose as it forms very fine solution drops smaller than 100 nm. After sample extraction, matrix solution is loaded with a nebulizer. The fog like matrix drops would help to form more uniform cocrystalline on the fibre tip surface. The amount of matrix loaded on the fibre or matrix to analyte ratio could be easily adjusted by varying the concentration of the matrix solution and the spray time.

Example 2 describes use of a MALDI/IMS interface which is associated with reduced noise. Reduced noise, though convenient, is not necessary. Thus, careful alignment of the laser with the sample surface is optional, as the fibre itself can accomplish this. As an alternative however, it would still be feasible to conduct a conventional MALDI analysis where the laser is directed at the surface of the fibre. This would allow devices to be constructed from non-light conducting fibres, and would eliminate the need to optically couple the device and the laser prior to analysis.

Multiplexing for Parallel Extraction and Quantification

The inventive device described lends itself to parallelization in both the sampling and quantification steps, due to both its cylindrical geometry and simplification of the analytical process.

FIG. 15 illustrates that parallel sampling could be accomplished by bundling multiple fibres, with the same or different coatings, to either probe multiple samples at once or to probe a single sample for multiple analytes. The bundle of fibres could also be used to provide efficient stirring during extraction. The extraction can be from multi-well autosampler plate, each well containing a different sample is extracted by a single fibre facilitating highly parallel determinations. The bundled extraction device could be employed for quantification by the MALDI process described above. The bundle could be multiplexed to a light source, and each individual probe irradiated in sequence by targeting the source at each individual fibre in succession. Simultaneously the sample end of each fibre would be positioned at the instrument for analysis. As shown in FIG. 15, a laser source 120 is irradiated in sequence onto each fibre in a fibre bundle 130 by means of a positioning device 122. The sample ends of the fibres in the bundle are directed into an extraction/desorption mesh 126. In this case only the tips of the fibres are coated with extraction phase 132 as this is the surface that is irradiated by the laser light. The sample end is positionable by means of a second positioning device 124. As each fibre is ready to be desorbed, it is positioned by the positioning device 124 at the sampling orifice of the mass analyzer 128 and the laser 120 is fired to intimate desorption.

Alternatively the probe bundle could be desorbed simultaneously into individual solvent desorption wells, with quantification by LC/MS.

The combination of fiber MALDI analysis with multiwell plates may also involve a positioning device to allow proper placement of the distal end of each coated fibre within a small opening of each well, so as to submerge the extraction phase. This approach requires design of a relatively small and accurate positioning device, to accommodate the large number of wells in a single high density multiwell plate. The technology now allows for over 1,000 wells to reside on one plate. Other introduction techniques may be used to introduce a sample or fibre into a well, specifically by using micromachined microfluidic systems where many microfluidic channels can be placed in one microfluid device to accommodate each fibre. This can be performed in combination with nanospray introduction to MS, where all fibres are desorbed in parallel in a microstructure, and subsequently each desorbed solution is introduced to MS in sequence.

Example 1

Preparation of Polypyrrole Coating on Stainless Steel Wires and Use in a Biological System Stainless steel wires (grade T-304V, 0.005") were from Small Parts Inc. (Miami Lakes Fla.). Lithium perchlorate (95%) and pyrrole (98%) were from Sigma/Aldrich (Mississauga, ON). Pyrrole was used as received for one month after opening, was stored refrigerated and the bottle was layered with nitrogen after each use. Polypyrrole (PPY) films were deposited onto the supporting electrode surface (stainless steel wire) by anodic oxidation of the pyrrole monomer in the presence of an aqueous electrolyte solution (counter ion). A potentiostat/galvanostat (Model 273, EG&G Princeton Applied Research) was used for the electrodeposition. The last 15 mm of the wires were coated potentiostatically at 0.8 V for 20 minutes. The placement of a silicon septum 15 mm from the end of the wire allowed for accurate control of coating length. The coating solution used was pyrrole (0.1M) and lithium perchlorate (0.1 M) in water and was prepared fresh daily. Coating was performed in a custom designed 50 mL flow-through glass compartment. Coating solution was pumped through the compartment continuously to allow for one complete change of solution during each deposition (50 mL/20 min.). The stainless steel wires were cut into 10.7 cm sections with a razor blade and 2-4 cm at the end to be coated was etched with 400 grit silicon carbide polishing paper. Wires were then sonicated in acetone until required to prevent accumulation of oxides or other contaminants on the wire surface. Immediately before use the wires were rinsed briefly with water and were installed as the working electrode. The counter electrode consisted of a ca. 10 cm section of platinum wire (0.75 mm OD) formed into a coil of about 1.5 cm diameter. The stainless steel wire was placed into the coating solution in the centre of this coil. A calomel reference electrode was used. The polypyrrole coating thickness was estimated to be <10 µm thick. Prepared probes were then placed into vials with sufficient buffer to cover the extraction phase and autoclaved for sterilization.

Wires prepared as described above were characterized in a series of in vitro experiments. Benzodiazepine standards (1 mg/mL in methanol) were purchased from Cerilliant (Austin Tex.). These were diluted in methanol to prepare mixtures of various concentrations for use in sample preparation and instrument calibration. Samples were prepared from buffer, dog plasma or dog blood and spiked with an appropriate amount of the analytes of interest. The device was placed directly into the sample contained in an appropriate polypropylene sample vial, for a certain period of time. After extraction the probe was rinsed briefly with a stream of water and either analysed immediately or allowed to dry prior to analysis. Drugs were stable in the extraction phase when stored dry at room temperature for at least 24 hours.

Figure 20:
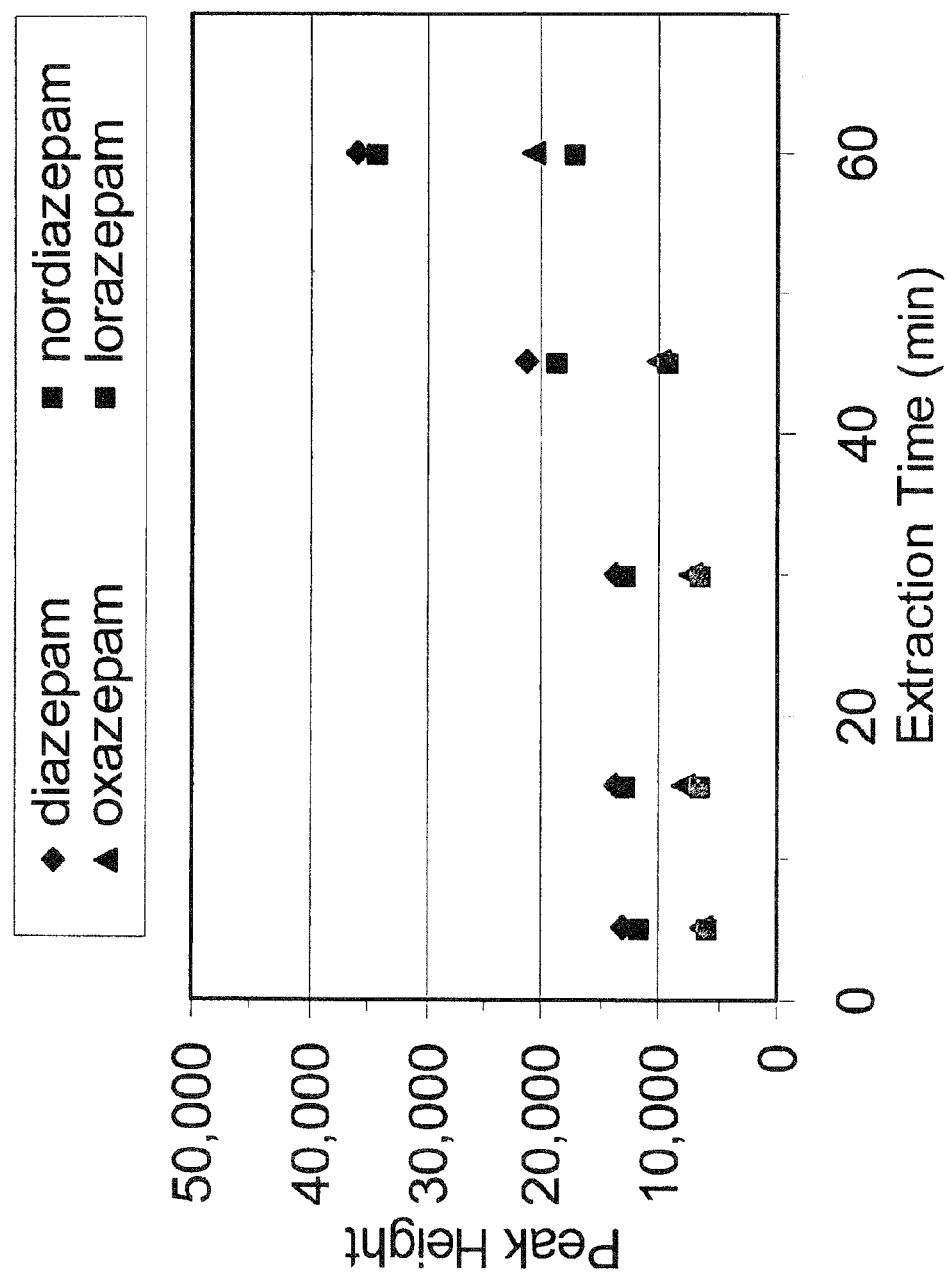
FIG. 20 shows extraction response versus time for standard devices.
Figure 21:
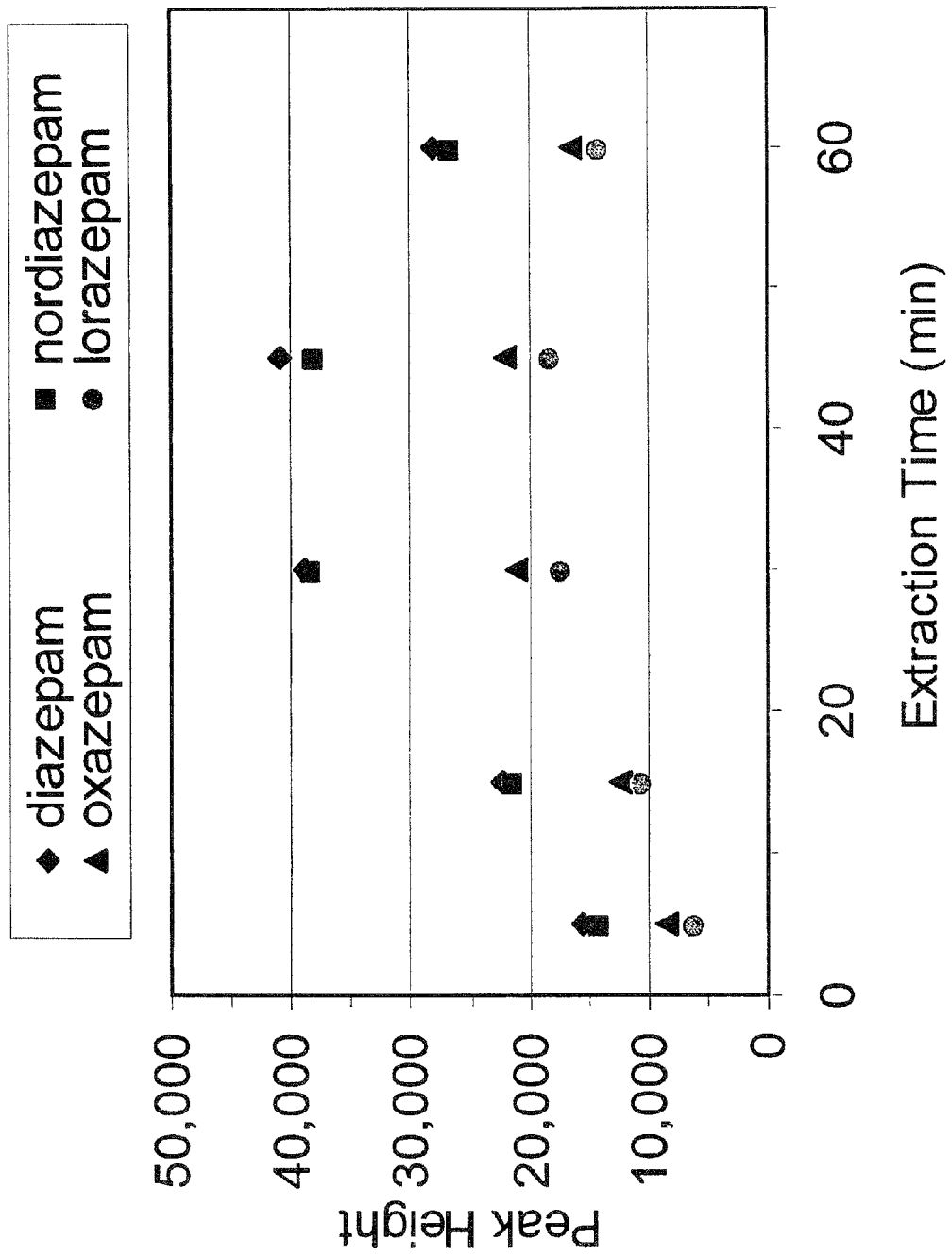
FIG. 21 shows extraction response versus time for preconditioned devices.

FIG. 20 and FIG. 21 show two alternatives for device response that may be achieved by this method. In FIG. 20 it can be seen that a fast initial equilibrium between the sample and native polypyrrole coated wires. After a longer period of time additional analyte is extracted as the polymer swells and exposes additional sites for extraction.

FIG. 21 shows that the polymer was preconditioned with methanol to provide a swelled polymer prior to extraction. The result the elimination of the initial lag time seen in FIG. 20 and an immediate increase in amount extracted with maximal extraction seen after 30 minutes when the analyte has diffused throughout the bulk of the polymer to access the additional sites exposed during swelling. This provides for additional sensitivity at the expense of a slower response time.

Figure 22:
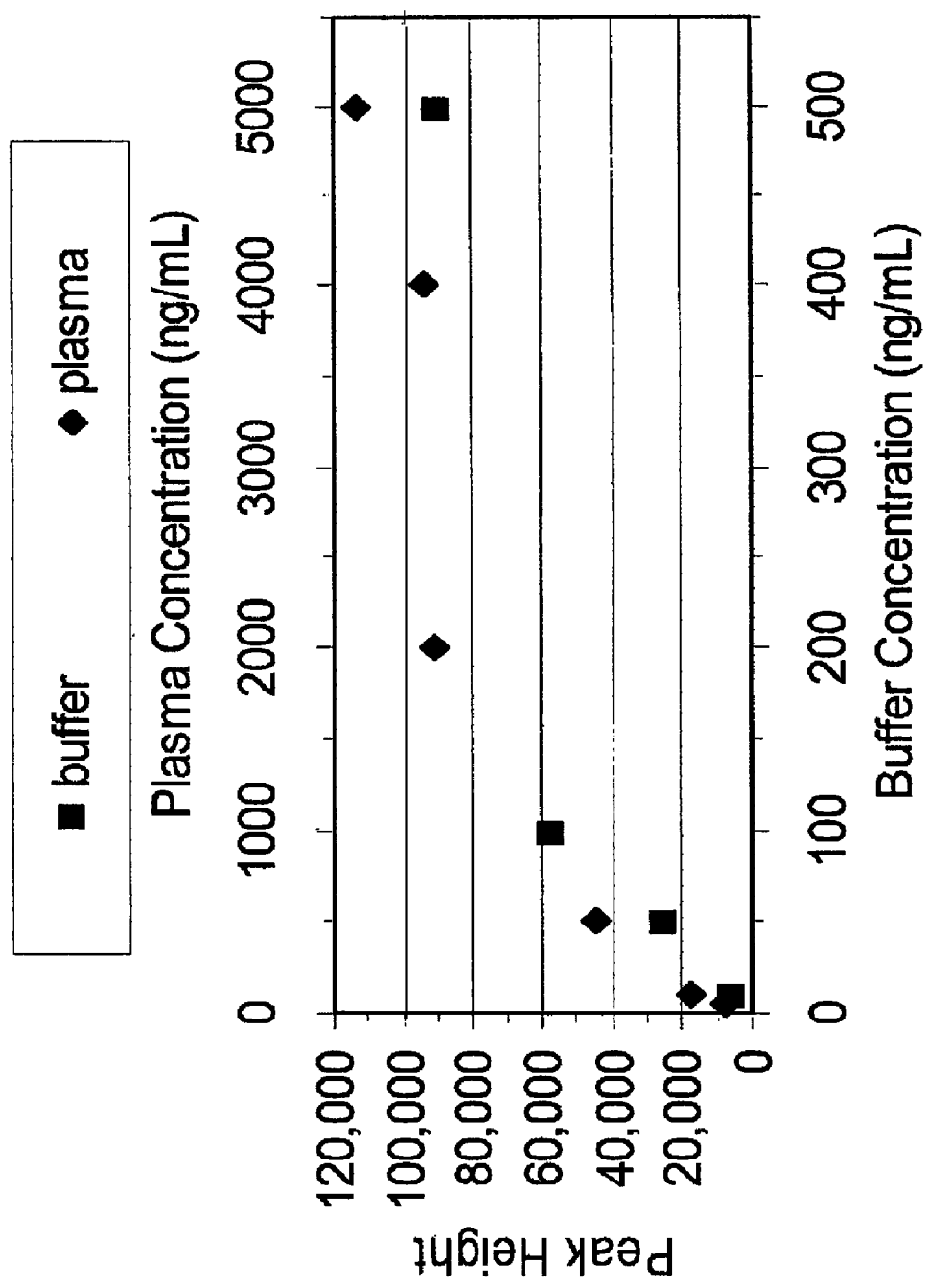
FIG. 22 provides a comparison of calibration in buffer and plasma, demonstration of linear response limit.
Figure 23:
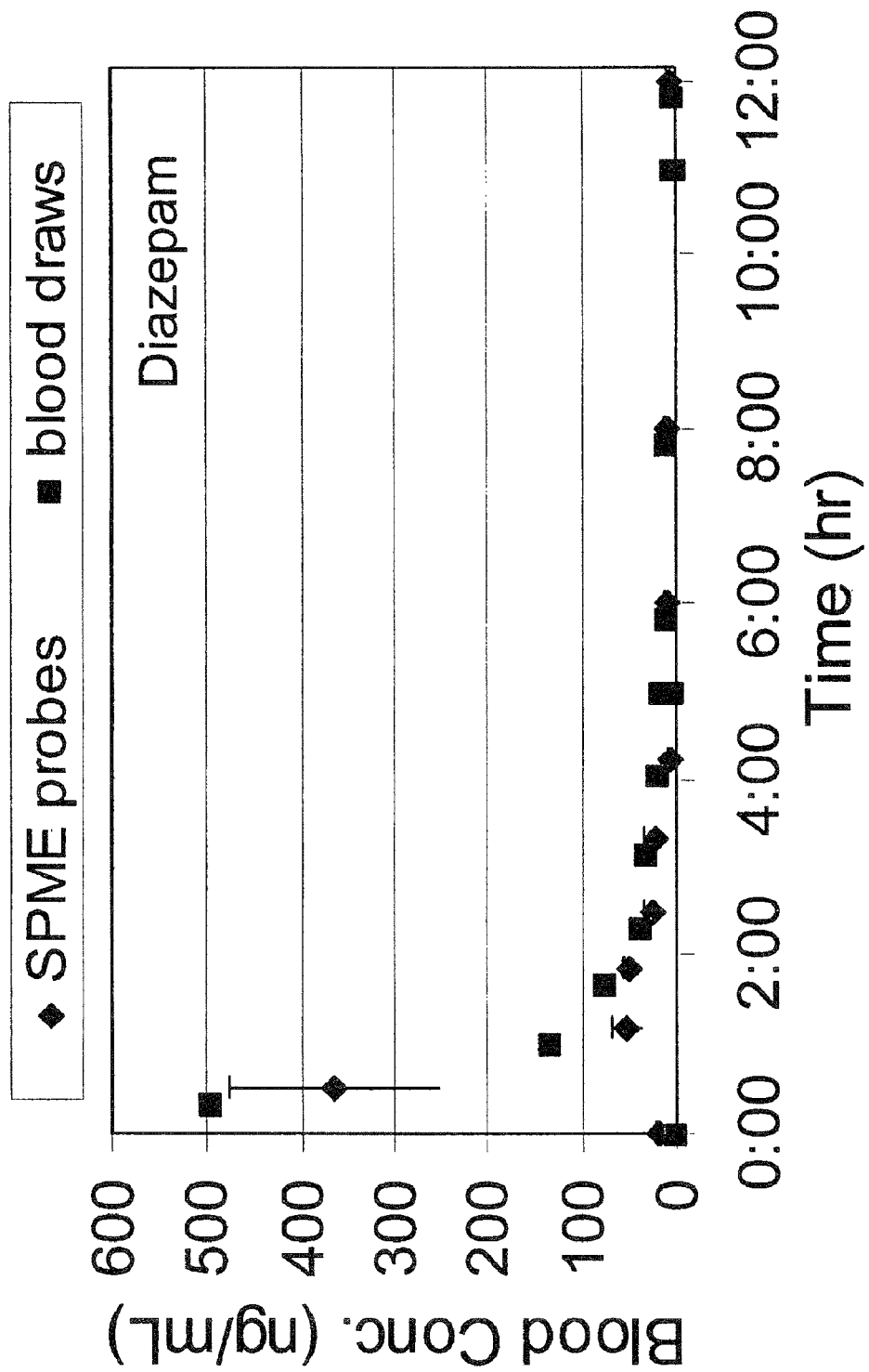
FIG. 23 illustrates an exemplary pharmacokinetic profile of diazepam.
Figure 24:
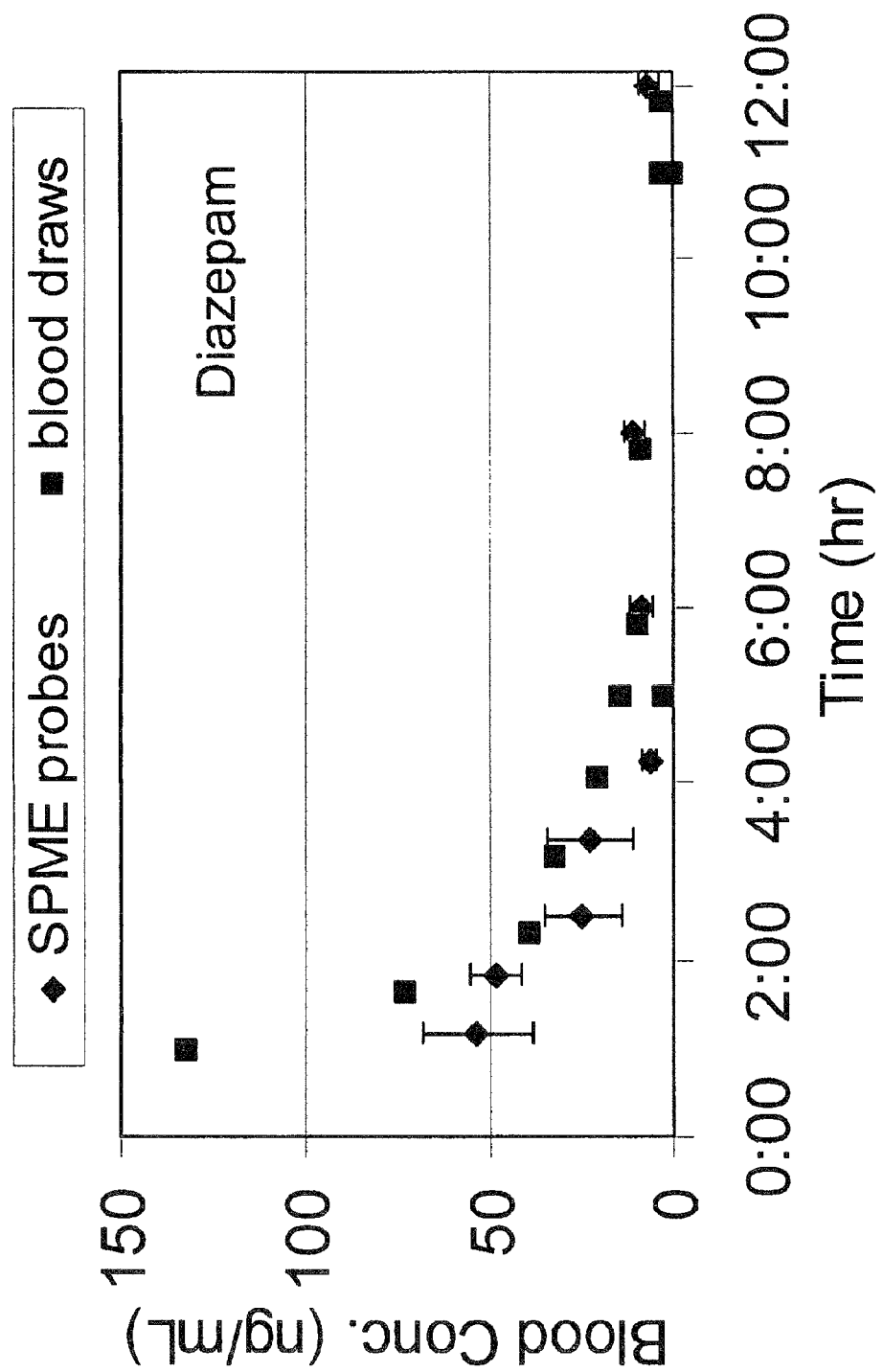
FIG. 24 illustrates an exemplary pharmacokinetic profile of diazepam, with an expanded y-axis.
Figure 25:
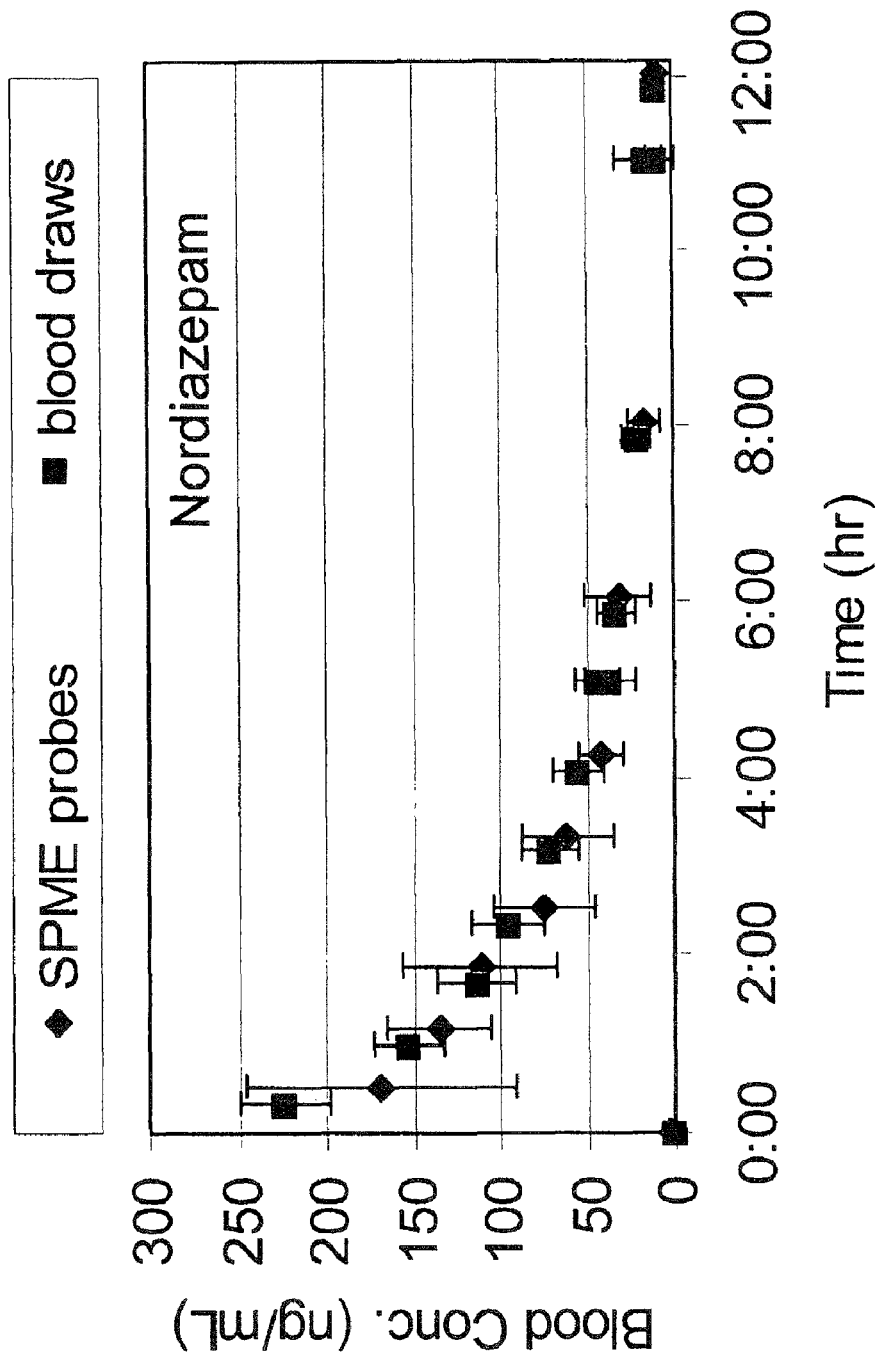
FIG. 25 illustrates and exemplary pharmacokinetic profile of nordiazepam.
Figure 26:
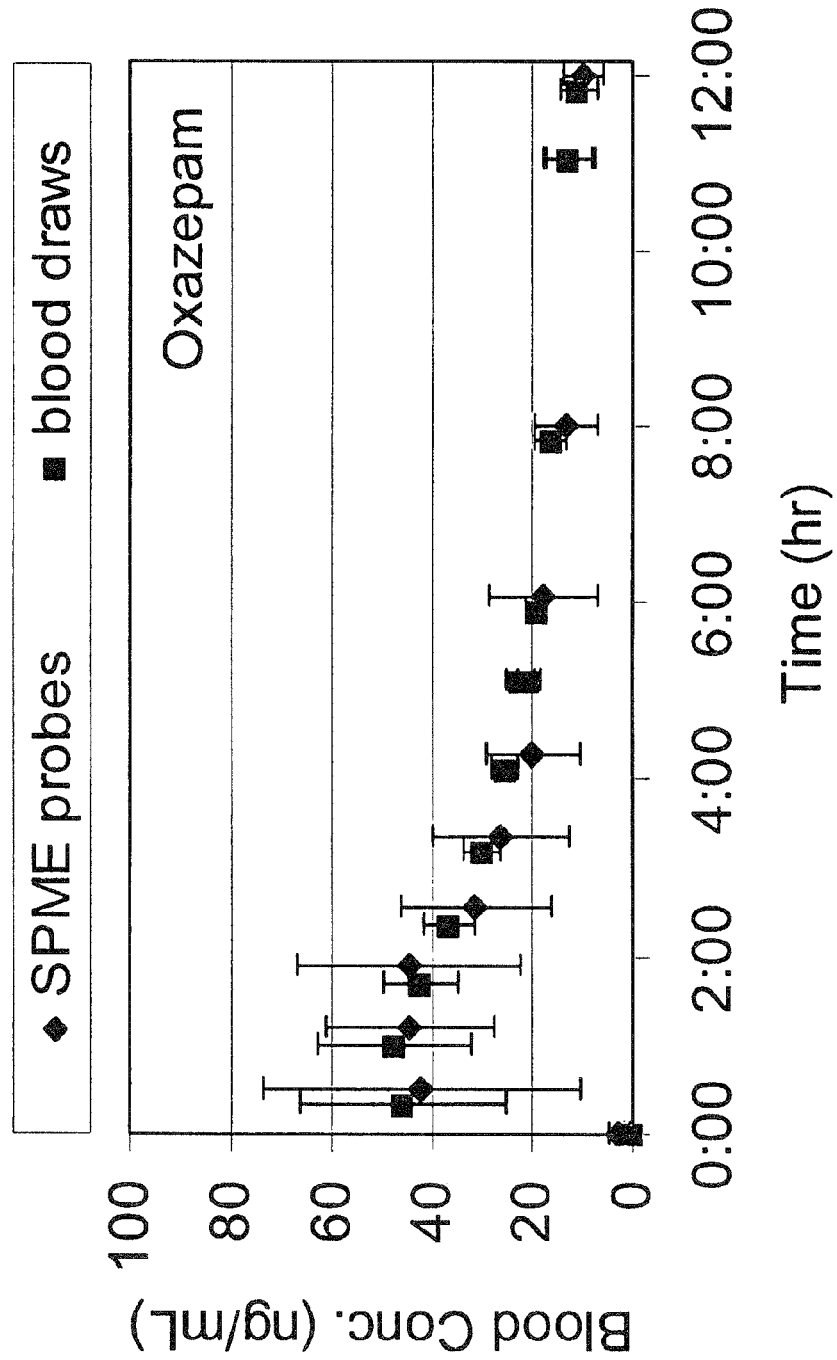
FIG. 26 illustrates an exemplary pharmacokinetic profile of oxazepam.

FIG. 22 shows the result of in vitro extraction calibrations from buffer and plasma. Because the device will only extract unbound drug and because the drugs under study are ca. 90% bound to protein, the plasma concentrations tested were 10× higher than the buffer concentrations. In buffer 100% of drug is free and 0% is bound to protein as no protein is present. In plasma, it is expected that 10% or less of the drug will be free. FIG. 22 demonstrates that the linear range attained is similar in buffer and plasma, based on free drug concentration. The figure also demonstrates that polymer extraction reaches maximal capacity in a solution with 100-200 ng/mL free drug.

After extraction (either in vivo or in vitro) the compounds on the device are desorbed in a small volume (10-20 µL) of desorption solvent, 75% methanol in this case. Maximal desorption is seen in as little as 20 sec. All or a portion of the desorption solvent is injected to an analytical instrument for analysis. This may be accomplished either on-line in a dedicated injection interface that takes the place of the regular injection port on a LC, or off-line in a small desorption chamber, followed by standard syringe injection of the desorption solvent by a commercial autosampler.

Figure 12:
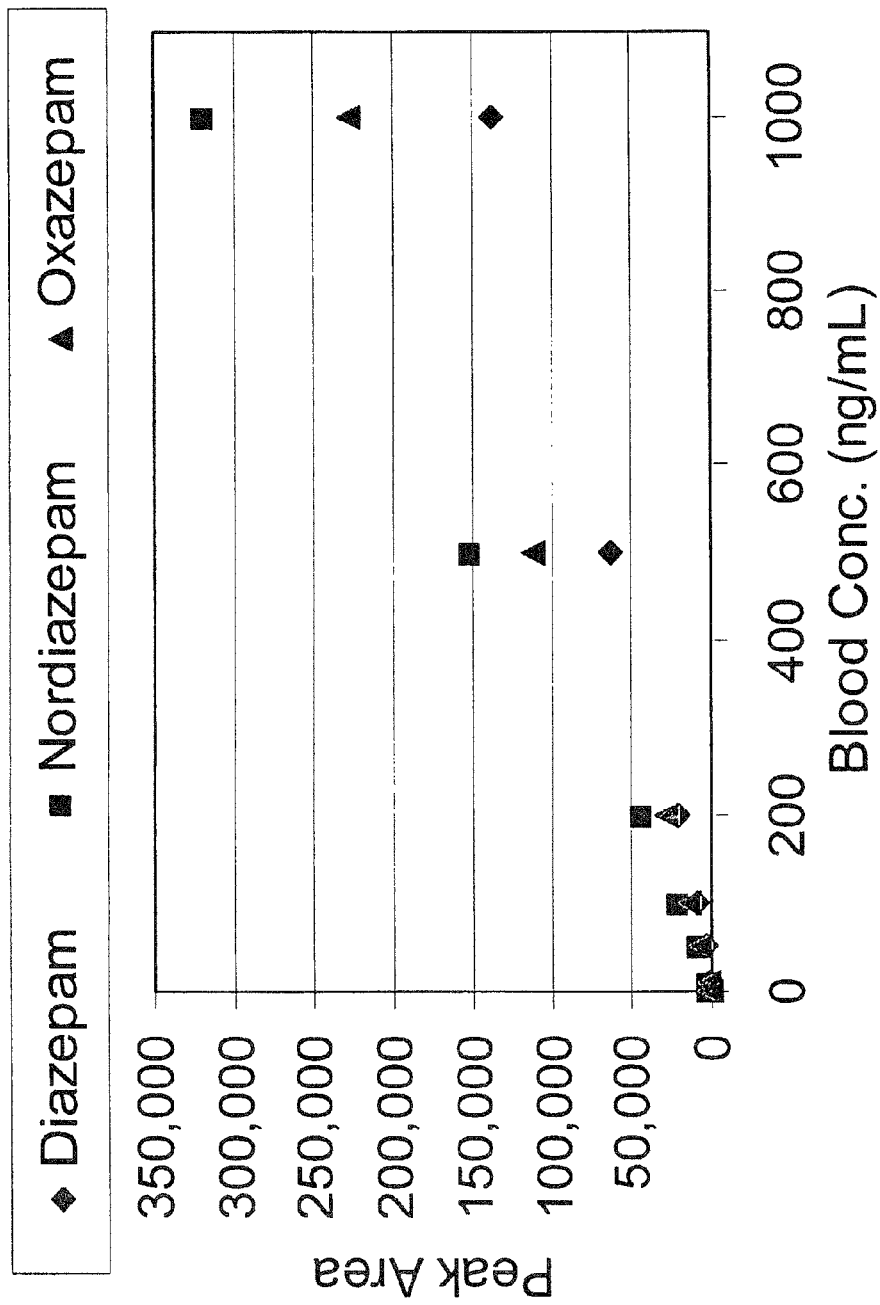
FIG. 12 illustrates calibration in whole blood used to calibrate device response.

FIG. 12 presents the results of a calibration from whole blood treated with an anticoagulant. The figure demonstrates good linearity in extraction over the range of total (bound plus free) drug shown.

FIG. 13 shows a chromatogram obtained after extraction of drugs spiked at 100 ng/mL from dog plasma, demonstrating the good chromatographic peak shape obtainable by the method. In this case the injection volume was ca. 11 µL, using the desorption solvent described above.

FIGS. 23 to 26 show the results of the use of the device by the catheter sampling method described above, for a pharmacokinetic study in dogs. In this case dogs were dosed with diazepam at time 0:00. Multiple samplings were performed from a catheter over the ensuing 12 hours. Calibration was by comparison to results from an external calibration in whole blood similar to that shown in FIG. 12. Also shown is a comparison to results obtained by multiple blood draws over the same time period, with conventional sample preparation and analysis as described in the description of the prior art. These results demonstrate that the device is useful for the application described and that the method described produces results in good agreement with devices and methods using invasive prior art sampling techniques.

Table 1 shows the limits of detection achieved in buffer and whole blood for a "probe" formed according to the invention. As can be seen from these data, the device and method allow an extremely sensitive detection of the analytes of interest, in this case: diazepam, nordiazepam and oxazepam.

TABLE 1

Limits of Detection Achieved in Buffer and Whole Blood

| Compound | Linear Range | detection limit (S/N = 3) ng/mL | slope | linear correlation ($r^2$) |
|---|---|---|---|---|
| SPME probe calibration from whole blood | | | | |
| Diazepam | 1-1000 ng/mL | 7.1 | 215 | 0.999 |
| Nordiazepam | 1-1000 ng/mL | 3.1 | 328 | 0.994 |
| Oxazepam | 1-1000 ng/mL | 2.7 | 258 | 0.996 |
| SPME probe calibration from buffer | | | | |
| Diazepam | 10-100 ng/mL | 0.43 | 306 | 0.999 |
| Nordiazepam | 10-100 ng/mL | 0.24 | 281 | 0.998 |
| Oxazepam | 10-100 ng/mL | 0.35 | 169 | 0.995 |

Example 2

MALDI Analysis

In this Example, a medical aerosol compressor was used as the matrix sprayer, and 10 mg/mL matrix DHB solution was deposited into the nebulizer vial. After analyte extraction the fibre tip was placed 1.5 cm above the nebulizer vial, and by turning on the compressor very fine drops of the matrix DHB solution were formed and attached to the fibre tip. The 800 µm fibre was tested with the spray method for a 0.05 mg/mL TOAB sample solution. The times for matrix application were set at 45 seconds and 30 seconds, respectively, considering the lower analyte concentration. Two 3 minute air-dry times were applied before and after the spray of matrix.

Figure 27:
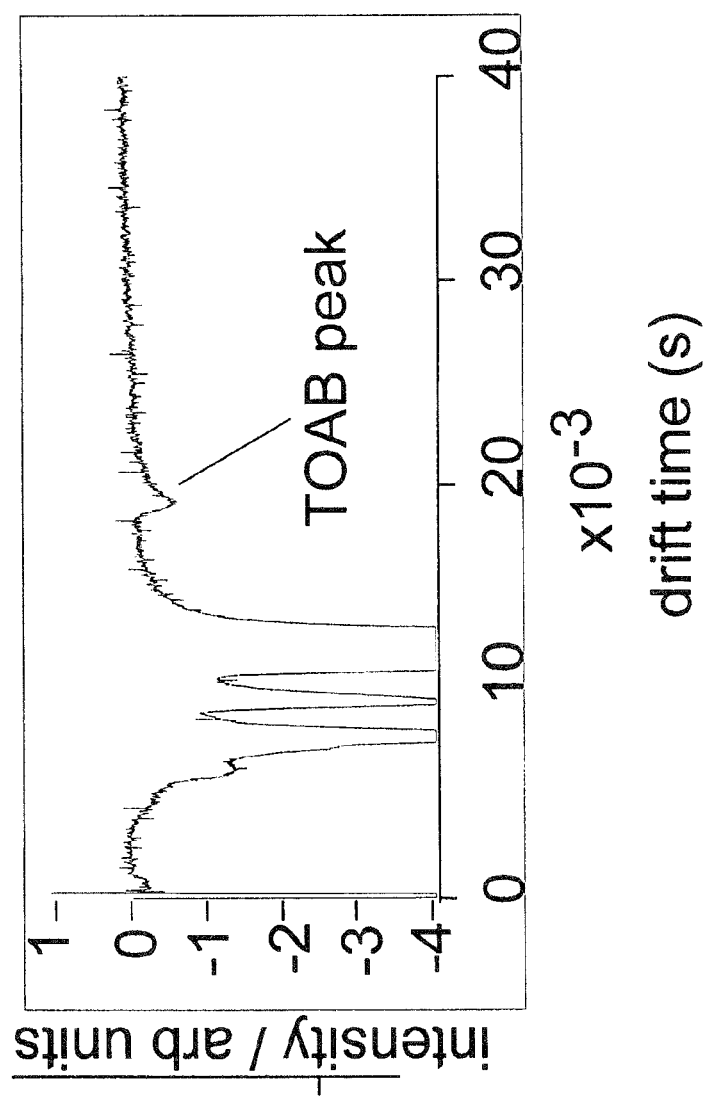
FIG. 27 shows an ion mobility spectrum obtained by matrix spray method at 0.05 mg/mL.

FIG. 27 shows an IMS spectrum from this analysis. The limit of detection was found to be 0.02 mg/mL with S/N ~2. This level is 10 times lower than the previous 0.2 mg/mL established by the 400 µm fibre using the pre-mixed method. The sensitivity has been increased dramatically. This great improvement was attributed to the larger surface area as well as the spray method.

In the work described above the laser pulse was shot down the core of the fibre. In addition to the advantages associated with reduced noise as described above, this is convenient as it is not necessary to carefully align the laser with the sample surface. The fibre itself accomplishes this. As an alternative however, it would still be feasible to conduct more of a conventional MALDI analysis where the laser is directed at the surface of the fibre. This would allow probes to be constructed from non-light conducting fibres, and would eliminate the need to optically couple the probe and the laser prior to analysis.

Example 3

On-Fiber and in-Needle Laboratory

In micromachined devices, controlling flow is not simple since it requires pumps or electroosmontic flow means. In addition it is quite difficult to mix analytes in the small channels. A more efficient approach is to do sample processing on the surface or in thin layers adjacent to the surface. The structures chosen in this Example are the outer surfaces of fibers. Alternatively, the inside surface of a tube fiber could be used. This Example makes use of a small fiber to demonstrate a convenient sampling method to collect analytes from small objects. In this work capillary electrophoresis with fluorescence detection has been used to facilitate detection of small amounts of analytes extracted by the fiber.

Chemicals and materials. 4-fluoro-7-nitro-2,1,3-benzoxadiazole (NBD-F) was purchased from Fluka (Sigma-Aldrich Canada Ltd., Oakville, Ontario). Brij35® and all amino acids (glycine, L-phenylalanine, L-proline, L-glutamate and L-aspartate) were obtained from Sigma-Aldrich Canada Ltd. (Oakville, Ontario, Canada). Sodium borate was from Fisher Scientific (Nepean, Ontario, Canada). All of the solvents used were HPLC grade, filtered and degassed and all the aqueous samples were prepared with deionized water (NANOpure, Ultrapure water system). A manual SPME assembly and replaceable extraction fibers, coated with Carbowax-temprated resin (CW-TPR, 50 um) were purchased from Supelco (Canada).

Instrument. The high voltage power supply for the CE system was from Spellman High Voltage Electronics Cooperation, Plainview, N.Y., USA. The CE separation capillary and silica fibers were purchased from Polymicro Technologies LLC, Phoenix, Ariz., USA.

The fundamental components of the laser induced fluorescence detection (LIF) are the laser, focusing lens, objective lens, interference filter and photomultiplier tube. An Argon ion ($Ar^+$) laser (~5 mW) was the excitation source. It provided an excitation wavelength of 488 nm (its maximum). The microscope objective lens (10×) and the low pass filter (530 nm) as an interference filter were from Melles Griot (Toronto, ON, Canada). The photomultiplier tube (PMT) and its socket including a high voltage power supply were purchased from Hamamatsu (R928 and C6271, Bridgewater, N.J., USA). In the design, the optical chopper and lock-in amplifier were used to enhance the signal indirectly. The optical chopper (SR-540) and lock-in amplifier (SR-510) were from Stanford Research systems (Sunnyvale, Calif., USA). The analog output signal from the lock-in amplifier was read by a plug-in data acquisition card (Star 4.5, Varian), which recorded at 20 Hz followed by the digitalization of the analog signal.

CE system set-up. The CE system was composed of a high voltage power supply and a separation capillary with an effective length of 45 cm (75 um I.D. and 385 um O.D.). The running buffer was 20 mM sodium borate, 10 mM Brij 35® and 2.5% methanol. The capillary was conditioned with 0.1 M sodium hydroxide (NaOH), water and running buffer for 15 minutes each. Between runs, the capillary was reconditioned with 0.1 M NaOH for 4 minutes followed by running buffer for 2 minutes. The running voltage was 12 kV. The injection was done hydrodynamically by raising the capillary inlet by 5 cm for 5 seconds.

In-solution derivatization reaction. The reaction solution was prepared by mixing 10 ul of each amino acid (0.01 mM in water), 10 ul of 1 mg/ml of NBD-F and 60 ul of 10 mM borate buffer at pH 8. This mixture was vortexed for 30 seconds and held in a 60° C. water bath for various periods of time (2, 5, 10, 30 and 60 minutes). The reaction solution was diluted to a final volume of 800 ul with running buffer and stored in an ice bath while waiting to be analyzed.

On-fiber derivatization reaction. A fiber was first cleaned by soaking it in ethanol. It was then dipped into a vial containing NBD-F (2-3 mg/ml in ethanol) for 10 min with magnetic stirring at 1000 rpm. After that it was transferred to a 1-ml Teflon centrifuge tube containing 200 ul of amino acids (0.1 mM) in sodium borate buffer (50 mM, pH 6.0) and dipped in the sample for 20 sec. A 4-ml amber vial containing 1 ml of triethylamine (TEA) was maintained in a 60° C. water bath. The headspace of this vial was basic. When the fiber with extracted analytes was exposed to it, the derivatization reaction took place (15 min).

Whole grape sampling with fiber/CE: interface and off-column desorption. The fiber/CE interface with off-column desorption was described previously. The desorption solvent (2 ul) was placed on the surface of the SPME fiber coating. This small droplet was manually rolled around the surface of the fiber coating. Finally this droplet was placed on top of a section of quartz tubing and it slipped down to the other end of the tubing where the capillary inlet was fixed. The capillary inlet contacted with this droplet for approximately 2 s. Since this quartz tubing was positioned 10 cm above the buffer vials, the droplet was hydrodynamically injected. The capillary electrophoresis was subsequently started. With such an interface, a commercial carbowax/TPR SPME fiber from Supelco could be used.

Fiber/CE interface: on-column desorption. On-column desorption has been described previously for a fiber/CE interface. The SPME micro fibers were made by attaching a 2-cm long silica fiber (100 um diameter) to a 10-cm polyimide coated silica capillary (100 um ID×365 um OD) with epoxy glue. The unit was air-dried overnight. The micro fibers were further etched to approximately 50 um diameter with 50% HF. These fibers were finally housed in stainless steel tubes and were sent to Restek Corporation, Bellefonte, Pa. for coating with carbowax.

Results and Discussion: Separation of amino acid derivatives. The critical micellar concentration (CMC) of Brij 35® is 0.9 mM. The CE running buffer used in these experiments had Brij 35® of 10 mM. Brij 35® not only forms micelles to improve the separation resolution, but also enhances the fluorescence intensity of the amino acid derivatives. Some studies have shown that Brij 35® will enhance the florescence signal of such derivatives by at least three times. The methanol (2.5%) in the running buffer functioned as organic modifier. It helped to increase the solubility of the solutes and enlarged the migration time window. As a result, a better resolution was achieved. Under these conditions, a mixture of five amino acid derivatives (phenylalanine, proline, glycine, glutamate and aspartic acid) was analyzed within 20 minutes.

On-fiber derivatization reaction of amino acids. The on-fiber derivatization of amino acids with NBD-F was first established with fibre/HPLC/fluorescence detector system described. On-fiber derivatization and a CE/LIF detection system has been described in the experimental section. The separation of amino acids derivatives was established. NBD-F reacts with to amines and nucleophiles under a mild basic condition. The peaks observed of sp-a represented the side products of the reaction of NBD-F and TEA. The peaks of sp-b observed are representative of the side products of the reaction of NBD-F with the aqueous buffer components and the sample matrix. NBD-OH is the major side product formed in the reaction of NBD-F with aqueous solution. Glycine could not be analyzed under these conditions because the glycine derivative co-eluted with one of the side-product peaks, sp-b. Glycine has an average migration time of 6.47 min (RSD=1.37%). Using a similar procedure, the fibre/CE/LIF detection system was used for the amino acid analysis. In this study, the fibre/CE with off column desorption was used.

Whole grape sampling: Off-column desorption fibre/CE interface. To demonstrate the application of this technology to the direct analysis of small living objects with on fiber derivatization coupled to a CE/LIF detection system, whole grapes were used as the samples. With a NBD-F doped fiber, the sampling procedure and derivatization reaction took 20 seconds and 20 minutes, respectively. The resulting electropherograms from this method with green grape (G) and red seedless grape (R) illustrate a glutamic derivative found at 7.05 min for the green grape sample and 7.01 min for the red seedless grape sample. These migration times corresponded to the L-glutamate standard 7.04 min. In the fibre/CE experiments, most of the peaks were saturated such that phenylalanine and proline derivatives were hidden in the saturated signal. For further identification of amino acids in the sample, the juice from the grapes was analyzed. The glutamate was also found in the grape juice sample in the form of glutamic acid.

On-column desorption fibre/CE interface. With the off column desorption, fibers with carbowax/TPR coating were used for sampling, while the on-column desorption was used with microfiber having thinner coating. These microfibers had a diameter between 75-50 um, and so could be used to sample smaller living objects. These microfibers were coated with carbowax. Electron microscopy was used to visualize the fibers and the fiber coating was found to be about 10 nm.

The feasibility of using these fibers for the on-fiber labeling reaction coupled to CE/LIF detection system was tested. First, the blank NBD-F solution was extracted with the fiber and desorbed on-column. The doping of NBD-F was successful. After the sampling of amino acid standard and reaction in the TEA headspace, no product was detected.

Example 4

Instrument and Method Calibration Using Fibers Loaded with Calibration Compound

One of the main advantages of the invention is that it allows very convenient introduction of extracted components onto analytical instrumentation, such as gas chromatography, liquid chromatography, supercritical fluid chromatography, capillary electrophoresis, micro-channel devices and even directly to mass spectrometry and detection instruments. This feature can be further explored for delivering calibration standards to analytical instrumentation. Currently standards are delivered to the instrument by injecting the solvent mixture containing appropriate calibration compounds. However, presence of solvent frequently interferes with calibration procedure. Therefore, it would be to user benefit to eliminate solvents from the calibration procedure. It can be accomplished by desorbing standard loaded fiber into appropriate instrument.

The loading of the fiber can be accomplished by exposing sorbent-coated fiber (extraction phase coated) to the source of the standard. The standard is then adsorbed onto the fiber coating. Another approach is to immobilize chemical standards via chemical reaction onto the fiber, which then is released to the instrument under conditions of increased temperature, light, chemical potential, mobile phase, etc. The second approach ensures stability of the calibrant, but as this Example demonstrates the first approach can also be very effective.

Two calibration methods were used. The first approach used solid sorbent coated fibres. One of the methods is to deliver the calibration compound by utilizing SPME fibre to the analytical instrument. The standard is first extracted from the standard mixture using strong sorbent followed by introduction of the standards loaded fibre into analytical system requiring calibration. In this approach liquid injection is avoided and thus solvent interference to the determination of trace VOC (volatile components) is eliminated. Satisfactory calibration curves were obtained for the very volatile compounds namely methanol, acetone, dichloromethane and chloroform when a 75-um Carboxen™/polydimethylsiloxane (CX/PDMS) fiber/coating was used. The standard gases or gas mixtures of VOCs were prepared using the NIST traceable certified permeation tubes combined with gas chambers or by microwave-assisted evaporation. "Stepwise" is the approach to the second calibration method developed during this work for on-site calibration of fibres. In this approach the CX/PDMS coated fibre was loaded with standard followed by exposure to the investigated system and then introduction into GC system for analysis. The accumulation time of analytes can be controlled equal to or different from that of the standard, and the response factors for the analytes can be adjusted accordingly. A good reproducibility of the response factors for BTEX was obtained with the stepwise method. Satisfactory results were obtained by using this method in quantitative analysis of BTEX in the gas station air. The introduction of standard via the stepwise procedure makes the technique more useful in field applications. This approach in some respects resembles standard addition, but also external calibration. It can be used to detect leaks, contaminations and losses from the time of standard loading onto the fibre to introduction to analytical instrument.

Preparation of standard gases or gas mixtures. Up to Now Several Methods have been developed for preparation of standard gas. Two methods were employed in this work to prepare the required standard gases or gas mixtures.

Preparation of gas mixture of BTEX using NIST permeation tubes. The Standard gas mixture of BTEX (benzene, toluene, ethylbenzene, p-xylene and o-xylene) was generated with the NIST traceable certified permeation tubes (Kin-Tech Laboratories, La Marque, Tex.) and the gas chambers build in our laboratory. It was a flow-through system with which a constant concentration of standard gas (or gas mixture) can be gained. The temperature was controlled at 50° C. and the air flow rate was at 300 ml/min. The gas mixture was sampled from the gas chamber.

Microwave-assisted generation of gas standards of VOCs. A domestic microwave oven (1000 W, Model MW5490 W, Samsung, Korea) and 1-L gas sampling bulbs (Supelco, Bellefonte, Pa.) were used for preparation of standard gases and gas mixtures of the investigated VOCs with different concentrations. The inner walls of glass bulbs were deactivated by silanization and the bulbs were cleaned with flushing nitrogen before use. For preparation of standard gases or gas mixtures of BTEX, 1,3-dichlorobenzene, 1,1,2-trichloroethane and tetrachloroethylene, a clean piece of glass wool (ca. 10 mg) was set inside the sampling port of the bulb each time and was moistened with deionized water (15 µL). Water was used to absorb microwave energy and then to prompt the evaporation of the compounds that are poor absorbers of microwave. For preparation of standard gas mixtures of acetone, methanol, dichloromethane and chloroform, no glass wool and water were needed. The port of the glass bulb was sealed with a Teflon-faced silicon rubber septum through which a certain volume of liquid of target compound (or mixture of several compounds) was injected onto the glass wool. Finally, the bulb was placed into the microwave oven to receive microwave radiation for 90 s. The microwave output was always set to the maximum power level. After cooling the Supelco bulb to room temperature, analysis of the standard gas was performed through the sampling port of the bulb where a septum is located.

The device and the "stepwise" procedure. Fiber coatings and conventional samplers used were provided by Supelco (Bellefonte, Pa.). The coatings utilized included 75-µm Carboxen™/Polydimethylsiloxane (CX/PDMS), 85-µm Polyacrylate (PA), 100-µm Polydimethylsiloxane (PDMS) and 65-µm polydimethylsiloxane/divinylbenzene (PDMS/DVB).

The stepwise procedure was conducted as follows: first, the fiber was exposed to tetrachloroethylene standard gas in the bulb, then the fiber was withdrawn into the needle after 2-min extraction and a Thermogreen Septum (LB-2, Supelco) was used to seal the tip of the needle. When using the field SPME sampler, no separate sealing septum is needed. The tetrachloroethylene loaded fiber was then exposed to BTEX standard gas mixture in the chamber or to real air sample for a few minutes. Finally, the fiber was transferred to the GC injector to desorb the standard and analytes at the same time.

GC-FID analysis of analytes. A Varian model 3500 GC equipped with a flame ionization detector (FID) was employed for sample analysis. A SPB-5 capillary column (30 m×0.25 mm×1 µm) from Supelco (Bellefonte, Pa.) was used and hydrogen as carrier gas at 30 psi. The column was programmed as follows: 35° C. initial, held for 1 min, ramp to 135° C. at 10° C./min and held for 1 min. The detector was maintained at 280° C. For the PA, PDMS and PDMS/DVB fibers, the injector was controlled at 250° C. and desorption time was 1 min, while CX/PDMS fiber was desorbed for 2 min at 300° C.

Comparison of introduction of VOCs standards into GC system by syringe injection of standard solution and by standards-loaded fiber. Several very volatile compounds, namely acetone, chloroform, dichloromethane and methanol, were selected for investigation. A standard solution was prepared using methanol as the solvent and the concentration of acetone, dichloromethane and chloroform was 10 µg/ml for each compound. The GC-FID chromatogram obtained by injecting 0.1 µl of the standard solution into the GC system illustrated that the solvent peak was too large to be well separated from peaks of other compounds and thus made it difficult to accurately determine those trace components.

On a contrary, there was no big solvent peak appearing in the chromatograms obtained by injecting a standards-loaded fiber into the GC system and an ideal separation and identification of the VOCs were therefore achieved. The analysis of the standard gas mixture was conducted for 3 min using a 75-μm CX/PDMS fiber and the concentration of acetone, chloroform, dichloromethane and methanol in the standard gas mixture was 50.5 μg/L for each compound. Due to the avoidance of solvent injection, it became easy to get satisfactory chromatograms for the micro amount of VOC standards, even for the very volatile compounds that possess quite short retention times.

In addition, it is difficult to obtain a calibration curve by directly injecting pure liquid of individual VOC or liquid mixture of VOCs into GC system to avoid introduction of plenty of solvent due to the difficulty of accurate injection of a very small volume (<<0.1 μl) of liquid standards into the GC system to match the quantitative ranges of trace analysis.

Calibration curves obtained with this technique for GC analysis of some VOCs. Two different fibers were used to extract the standard gas mixtures of two different groups of VOCs. The very volatile compounds, including acetone, chloroform, dichloromethane and methanol, were extracted with a 75-μm CX/PDMS fiber, which has a high affinity towards to VOCs as described above. BTEX were extracted with a 100-μm PDMS fiber. It is known that the PDMS fiber extract target compounds by absorption while CX/PDMS fiber works by adsorption. By introduction of the VOCs standards into GC system with fibers, satisfactory calibration curves regarding the concentration-response relationship for SPME-GC-FID analysis of the mentioned VOCs were obtained and shown in FIG. 2. The related calibration equations were listed below:

Methanol: $A=767.69C+3564, R^2=0.9937$ (1-a)

Acetone: $A=3234.8C+22693, R^2=0.9952$ (1-b)

Dichloromethane: $A=1004.6C+7271.5, R^2=0.9965$ (1-c)

Chloroform: $A=980.46C+719.5, R^2=0.9993$ (1-d)

Benzene: $A=106.18C-1069.5, R^2=0.995$ (2-a)

Toluene: $A=326.42C-4320.8, R^2=0.9993$ (2-b)

Ethylbenzene: $A=711.53C-6136.8, R^2=0.9958$ (2-c)

p-Xylene: $A=868.43C-10704, R^2=0.9994$ (2-d)

o-Xylene: $A=995.98C-9588.1, R^2=0.9972$ (2-e)

where A is the chromatographic peak area (counts) and C is the concentration of VOCs standard gas (μg/L).

The experimental results demonstrated that the investigated fibers are efficient for introducing VOCs standards into GC system without solvent injection for getting calibration curves and fibre-GC is a highly feasible method for quantitative analysis of VOCs, even for the very volatile compounds.

Moreover, it is also possible to establish the "mass:response" calibration curves for GC analysis of VOCs by introducing standards with SPME fibers. When absorption-type fibres are employed to extract analytes, there is a direct relationship between the initial analyte concentration in the sample ($C_0$) and the amount of the analyte extracted by the fibre at equilibrium (n) according to Equation 3-a:

$$n = \frac{K_{fs}V_sV_fC_0}{V_s + K_{fs}V_f} \quad (3\text{-}a)$$

where $K_{fs}$ is the fibre/sample partition coefficient, $V_f$ is the fibre coating volume and $V_s$ the sample volume. For adsorption-type SPME process, the amount of analyte A extracted by the fibre at equilibrium (n) also grows with the increase of the initial analyte concentration in the sample ($C_{0A}$) before saturated adsorption reached:

$$n = C_{fA}^\infty = \frac{K_A C_{0A} V_s V_f (C_{fmax} - C_{fA}^\infty)}{V_s + K_A V_f (C_{fmax} - C_{fA}^\infty)} \quad (3\text{-}b)$$

where $K_A$ is the adsorption equilibrium constant of analyte A, $C_{fA}$ is the concentration of analyte A on the fibre at steady state, $C_{fmax}$ is the concentration of active sites on the surface (corresponding to the maximum achievable analyte concentration on the surface), $V_s$ and $V_f$ are the volumes of the sample and the fibre coating, respectively.

Stability of VOCs on extraction phase coatings after exposing the coatings to zero air. Analytes present in sample by either absorption or adsorption, collect or enrich the target compounds from samples onto the coatings. However, similar to other extraction procedures, enrichment is followed by an opposite procedure, the release of extracted compounds from the coating phase. Therefore, when a coating loaded with some VOCs is exposed to pure air, a part of extracts will transfer to the air and then the extracts tend to reach an equilibrium distribution between the coating and air phases. The release of the extracts from the coating phase depends on a lot of factors, mainly the compounds' and coatings' properties, the temperature of the environment and the differences of the compounds' concentrations in the coating phase and in the sample or environment. It was shown in Table 2 that the remains of several VOCs (BTEX were included) on the 85-μm PA, 100-μm PDMS and 65-μm PDMS/DVB coatings ranged from 0 to 91.5% after exposing the coatings to zero air for 1 min at room temperature. However, the 75-μm CX/PDMS coating could store the extracts as much as 89.9%-97.2% even through a 6-min exposure to zero air under the same conditions. Actually, no obvious losses could be found for most of the extracts on the 75-μm CX/PDMS coating when exposure time was controlled within 4 min. Thus it is possible to allow a "stepwise" procedure conducted with the CX/PDMS coating—that is, this coating can be used to extract a compound in first step and then transferred to extract other compounds while the compound extracted previously still remains on the coating.

Selection of internal standard for BTEX analysis with stepwise Procedure. 1,3-dichlorobenzene, 1,1,2-trichloroethane and tetrachloroethylene were tested, respectively, as internal standards for BTEX analysis when a 75-μm CX/PDMS coating was used. The CX/PDMS coating has a strong affinity towards these compounds and their storage on the CX/PDMS coating was close to that of BTEX. Considering their chromatographic behaviors, tetrachloroethylene is the best internal standard for BTEX analysis since it can be well separated from BTEX and its peak is located in the central position of the chromatogram. Further investigation demonstrated that, under the selected conditions, the loading of tetrachloroethylene on the fiber did not affect the BTEX, and in turn, the BTEX did not affect the storage of tetrachloroethylene on the fiber either. Tetrachloroethylene as the internal standard for BTEX analysis has another advantage—that is, its background is generally not present in main BTEX sources like petroleum. However, tetrachloroethylene also has its drawbacks: it is a halogenated compound and the GC-FID response for it is not as sensitive as for BTEX. The problem involved in determination sensitivity for tetrachloroethylene can be solved by using selective detectors like MSD or FPD.

Response factors for BTEX when tetrachloroethylene was used as internal standard. For chromatographic analysis, the response factor (F) can be defined as the following form:

$$\frac{Ax}{Cx} = F\frac{As}{Cs}, \quad (4)$$

where Ax and As are the peak areas of analyte X and internal standard, while Cx and Cs the concentrations of analyte X and standard after they have been mixed together. For the use of tetrachloroethylene as internal standard for BTEX analysis following the stepwise procedure described above, the standard is not mixed with analytes before they were extracted onto the SPME fiber. In such a case Cs stands for tetrachloroethylene's concentration of the standard gas and Cx is individual BTEX's concentration in the sample.

For the stepwise GC/FID analysis of BTEX, the response factors were measured. The time for of BTEX was 2 min, equal to that for the standard. It can be seen that the response factors highly coincided for duplicate tests in almost all cases. This reflects that the stepwise procedure is a feasible and practicable method to introduce internal standard for GC analysis of BTEX when the CX/PDMS coating is used.

Effect of extraction time on response factors for stepwise procedure. It should be noticed that the response factors discussed above are not only related to the sensitivity of GC-FID determination to individual BTEX but also depend on the SPME efficiency for them. Since the standard and BTEX were not extracted at the same time during the stepwise procedure, the time for BTEX can be controlled equal to or different from that for the standard. Obviously, time control will significantly affect the response factors. This is one of special features of the stepwise procedure distinguishing with the conventional way to use internal standards. In the conventional way, the extraction of analytes and internal standard is conducted simultaneously. It was found that the response factors varied linearly with the time for SPME of BTEX in the range of 1-5 min when SPME time for tetrachloroethylene (standard) was constantly controlled as 2 min. The linear equations obtained were as follows:

Benzene: $F=4.265t+1.301$, $R^2=0.9979$; (5-a)

Toluene: $F=5.776t+0.402$, $R^2=0.9981$; (5-b)

Ethylbenzene: $F=4.663t-0.031$, $R^2=0.9996$; (5-c)

p-Xylene: $F=4.623t-0.247$, $R^2=0.9993$; (5-d)

o-Xylene: $F=4.767t-0.703$, $R^2=0.9963$, (5-e)

where F is response factor and t is time in minute for BTEX.

The concentrations of both standard and analytes were within the linear ranges when the internal standard was used. GC-FID is known to have a linear response to VOCs during a very wide range and so is the inventive procedure with the CX/PDMS coating. The excellent linearity of the response factors for BTEX varying with the extraction time also reflected that the compounds' concentrations studied were located within the linear range.

Field application—analysis of BTEX in the air of a gas station. The VOCs (BTEX were the interests) were sampled from a gas station that is 5-min walk to our laboratory, using the home-made field sampler with a 75-μm CX/PDMS coating. It was a clear day and the temperature was ca. 24° C. when the sampling was conducted. The glass bulb holding the standard gas of tetrachloroethylene (8.1 μg/L) was carried to the field and analysis of tetrachloroethylene was performed prior to BTEX. The sampling time was 2 minutes for the standard and 4 minutes for the gas station air. As soon as the sampling was finished, the sampler was delivered to the laboratory and then the fiber was immediately introduced to GC-FID. The identification of individual BTEX was based on their retention times as well as GC-MS analysis using a Hewlett-Packard 6890 GC equipped with a 5973 MSD (Agilent Tech., USA). Tetrachloroethylene was not found in the gas station air itself. The separation of standard and BTEX from other components of the extracts was very good, only one peak might contain m- and p-xylenes, which couldn't be separated from each other under the selected chromatographic conditions. Finally, using the peak areas obtained (As and Ax), the standard concentration (Cs) and the response factors (F) given by Equations 5-a-5-e, the concentrations of BTEX in the air were calculated according to Equation 4.

Conclusion. For getting calibration curves in GC analysis of VOCs in air, fiber was successfully used to introduce VOCs standards into GC system without solvent injection. The avoidance of solvent injection with the inventive technique made it easy to obtain satisfactory chromatograms for micro amount of VOC standards, even for the very volatile compounds that possess quite short retention times. Moreover, a stepwise method was developed to introduce internal standard for GC analysis of BTEX in field application. The CX/PDMS was proved to be the only suitable coating to fit this method due to its extraordinary affinity towards VOCs. Tetrachloroethylene was selected as the internal standard for reasons such as its proper retention time compared with those of BTEX for GC analysis, similar behaviors to BTEX on the CX/PDMS coating and very low background in main BTEX contamination sources in the environments. Using the developed method, analytical results can be calibrated without a necessity to spike standard material into samples, hence it makes the inventive procedure even more advantageous in field applications. However, since the standard is not directly added into the sample and the analysis of standard and analytes is conducted stepwise, this method may not meet the need of calibration of the air matrix's effects on the analysis of BTEX. This approach is also suitable to detected problems with fiber storage in filed devices, such as leaks, which will result in analyte and standard losses. Further development of the technology can include chemical immobilization of compounds, which will facilitate production of certified standards.

Example 5

Electrophoresis in Non-Uniform Channel Modulated by Insert

Electrophoretic behavior of analyte in capillary consisted of two parts with different cross-section was investigated. The modulation of the separation path was achieved by inserting into the capillary a cylindrical fiber at different depth. The sample loaded at the end of lower cross-section and the appropriate zone, at it was demonstrated, spatially narrowed in the wide capillary part according to the electric field strength ratio in the two parts of the capillary. Additionally, the low conductive sample buffer can enhance the further signal narrowness and increase the total probe amount, introduced into the capillary by electroinjection. The applications of this concentration technique includes focusing after desorption from SPME fibers into the electrophoretic separation channel prior separation or prior to direct detection using for example UV-Visible, Fluorescence, electrochemical, NMR or mass spectrometry detection. Also, focusing of analytes present in a buffer is possible by inserting different shapes inserts prior to separation or direct detection. Periodic insertion of the insert into the channel will modulate the concentration of analyte, which facilitate separation and monitoring of the system connected to the separation channel. The modulation input could be random and the signal can be then analyzed by multiplex data processing techniques, such as cross-correlation. Modulation of the diameter of the channel can be also accomplished by applying external pressure or electrical pulses, which will also result in focusing without need for movement of the insert in and out of the channel. The results described below indicate that the focusing occur in a cross channel configuration since the channel cross-section diameter increasing substantially in the area where two channels meet. This can be used effectively to facilitate concentration of analyte prior to separation in the second channel, or in two-dimensional separation when the separation in the first channel is followed by focusing at the interface between the two channels prior to second dimension separation in the second channel.

Introduction. Non-constant form of a separation channel in electrophoresis is a way of providing the variance of some parameters (electric field strength, temperature, pH) which can play an important role for the process concerned. Smooth form changing is required should one need to obtain the appropriate smooth function. By varying a cross-section of electrophoretic camera one obtains an electric field gradient, this gradient can be used both in combination with some other force applied, what is used in so-called "gradient focusing techniques" or by itself provided the current density drop and the chamber design are appropriate to form sufficient temperature difference. The latter effect was used in IEF in thermogradients caused by internal Joule heating.

A separation channel, composed of few different parts but each one of constant form, can be used rather for sample introducing, detecting, multi step analysis development in microarray etc. The results described in this paper are also important for the methodologies where the sample application procedure is connected with a long object inserting (e.g. microfiber) into the separation capillary.

Experimental: Apparatus. The whole-column imaging detection (WCID) of UV absorbance was conducted in the iCE280 CIEF instrument (Convergent Bioscience Ltd., Toronto, Canada) with a fixed wavelength of 280 nm. A short fused-silica capillary (5.5 cm long) with an ID. of 100 um, internally coated with fluorocarbon (J&W Scientific, Folsom, Calif.), was assembled in a cartridge format (Convergent Bioscience Ltd.) The entire process of capillary conditioning, sample injection, data collection, and processing was implemented by a PC computer, and the electropherogram was recorded as absorbance versus the distance to the anode.

Materials and Chemicals. Optical fiber with a 50 and 61.5 um core (FHP050055065 & FVP60072082) was purchased from Polymicro Technologies Inc. (Phoenix, Ariz.). pI-markers and buffer chemicals were obtained from Bio-Rad. Water was purified using an ultrapure water system (Barnstead/Thermolyne, Dubuque, Iowa) and was used for all solutions.

Procedures. The fiber was inserted into the capillary at different distances and the capillary was filled with running buffer (Phosphate 5-100 mM, BioRad). Then, the sample was injected electokinetically, with the injection time being specially selected to achieve complete replenish of the first of the first capillary part (containing an inserted microfiber). After, the electrode reservoirs were washed and the desired buffer was placed and the electrophoretic run performed.

Results and Discussion. The initial zone width is an important matter in CZE. For the case the sample concentration is insufficient to provide sensitive detection, a number of on-line preconcentration procedures is developed. The simplest electrophoresis-based techniques are connected with a special conductivity profile creation allowing us to achieve a higher electric field strength value in the sample zone place, although concentration mechanism may be different (e.g., CE- or ITF-based). The similar effect of electric field enhancing can be obtained due to stepwise cross-section change.

In these experiments, by inserting the cylindrical microfiber the cross-section of the separation channel was modulated. Sample was injected electrokinetically at 500 v, the duration of voltage pulse was controlled to achieve complete filling of the first part of the capillary (up to the end of microfiber).

The initial starting zone was rather wide (taking into account the "dead" volume-around one half of the capillary). Then it was effectively compressed, in the same proportion as one could expect starting from cross section difference. In the case of two co-axial cylinders the cross-section ratio ($R=S2/S1$) is: $R=D2/(D2-d2)$, where D is the diameter of the capillary and d is the one of the microfiber inserted. By the assumptions of constant conductivity, the electric field increase in the narrow part ($E1/E2$) is defined by $S2/S1$, and the initial zone length should be narrowed in the same proportion, approximately.

The effect of observed can be combined with methods traditionally used for sample preconcentration. With using low conductivity buffer it was possible to achieve an essential concentration sample increase in the plug introduced, although the peak width change was less evident.

This effect described above does not provide by itself any concentration increase in the introduced probe, since the volume of the sample zone should remain constant and the sample plug narrowing is due to it form change. But this simple and clearly visible effect still opens a lot of important applications to start with to start the separation from "initially wide" zone when it is necessary. For example, working with the inventive technique, one can insert a microfiber into the capillary and obtain a rather wide starting zone, with electric field application the initial zone can effectively be narrowed at the end of microfiber. The latter effect, obviously, depends on the relative size of microfiber inserted, and to achieve high zone narrowing the (D−d) difference should be small enough.

Solid phase microextraction and direct desorption of fluorescent labelled analytes into the separation channel was observed. The process is monitored by the fluorescence whole column imaging detection. The excitation light is delivered to the separation channel using the fiber. This work successfully demonstrates the stacking process that occurs in CE coupling interface with LIF imaging detection. Based on the enhancement in fluorescence intensity, concentration efficiency can be approximated to be as high as a 10-fold. Higher concentration efficiency could be expected with further optimization of configuration of the interface and the experimental conditions used, such as, dimensions of separation capillary and fibre, buffer concentration and applied voltage. The stacking effect generated by such an interface is beneficial to separation efficiency and detection sensitivity of CE separation.

Example 6

Demonstration of Isotropy of Absorption and Desorption

As an alternative to conventional internal standard calibration, a standard may be loaded onto the SPME fibre prior to analysis and the loss of standard from the fibre can be monitored instrumentally. Where the kinetics of absorption of the internal standard analyte to the fibre is equivalent to the kinetics of desorption (binding is reversible), absorption and desorption are controlled by diffusion in the sample and the rate of loss of standard from the fibre will be correlated with uptake of analyte by the fibre. The amount of standard lost and the amount of analyte absorbed may be measured and used to estimate the unknown concentration of analyte. Using this strategy, variation in the sample convection may be controlled for by referencing the unknown analyte to the amount of calibrant lost from the fibre. In other words, the loss of the standard is used in this approach as an "indicator". Extraction of an analyte onto a SPME liquid coating fibre from an agitated sample matrix is theoretically described with Eq 6 [Ai, J. *Anal. Chem.* 1997, 69, 1230-1236]:

$$\frac{n}{n_0} = [1 - \exp(-at)] \quad (6)$$

where n is the amount of extracted analyte, and $n_0$ is the amount of analyte extracted onto the fibre at equilibrium. Constant a is a measure of how fast a desorption/absorption equilibrium can be reached, and is determined by mass transfer coefficients, distribution coefficients, physical dimensions of the sample matrix and the fibre coating. Analogously, desorption of an analyte from a SPME liquid coating fibre into an agitated sample matrix can be theoretically described with Eq. 7:

$$\frac{Q}{q_0} = \exp(-at) \quad (7)$$

where Q is the amount of analyte remaining in the fibre and $q_0$ is the initial amount of analyte extracted onto the fibre.

The isotropy of absorption and desorption of an analyte onto and from a SPME fibre is demonstrated by adding Eq. 6 and Eq. 7. The left side of Eq. 6 represents the fraction of the analyte absorbed on the fibre after absorption time t, while the left side of Eq. 2 represents the fraction of the analyte remaining on the fibre after desorption time t. Constant a in Eq. 6 for absorption has the same definition as constant a in Eq. 7 for desorption. In other words, the value of constant a for the same compound should be the same for both absorption and desorption under the same conditions (sample bulk velocity and temperature). This implies that the sum of $$\frac{Q}{q_0}$$

(desorption) and $$\frac{n}{n_0}$$

Figure 28:
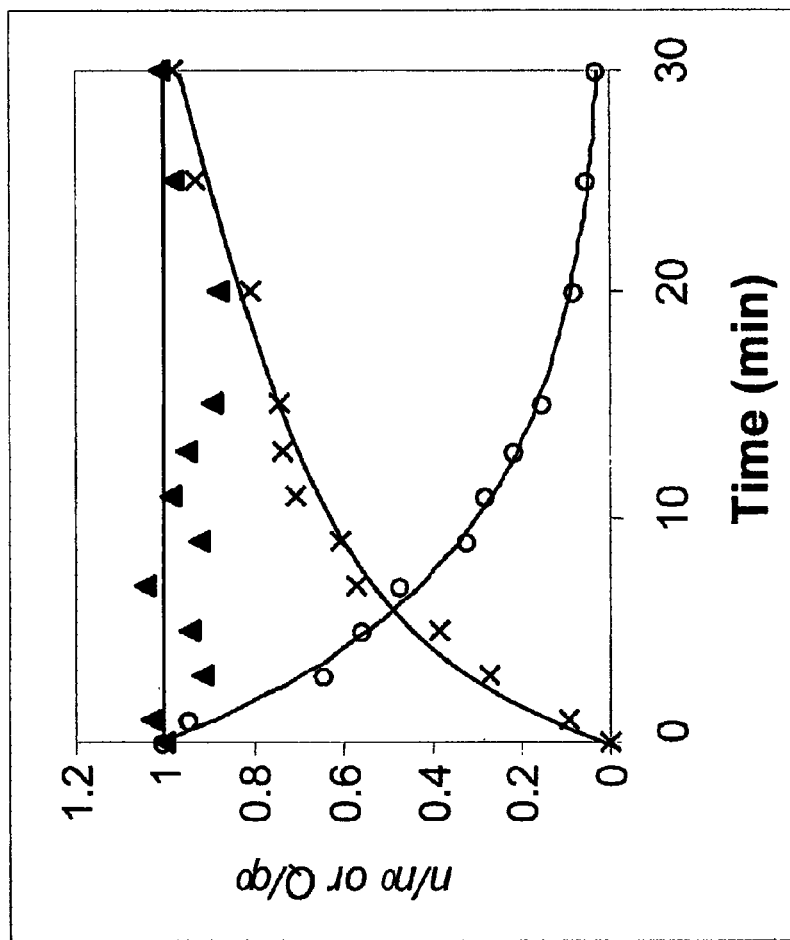
FIG. 28 shows isotropy of absorption of toluene (component) and desorption of deuterated toluene (calibrant) in SPME using PDMS coated fibre.

(absorption) should be 1 at any desorption/absorption time for simultaneous absorption and desorption of the same analyte. Our initial experimental results indicate that this conclusion is correct. It has been confirmed by the simultaneous determination of the desorption time profile of deuterated (d-8) toluene and the absorption time profile of toluene: a 100 µm polydimethylsiloxane (PDMS) fibre was loaded with deuterated toluene, then the fibre was exposed to a flowing standard toluene aqueous solution for different times. FIG. 28 presents the values of $$\frac{Q}{q_0}$$

calculated from the desorption time profile, the values of $$\frac{n}{n_0}$$

calculated from absorption time profile, and the sum of $$\frac{Q}{q_0}$$

and $$\frac{n}{n_0}$$

for simultaneous absorption of toluene and desorption of deuterated (d-8) toluene onto and from a 100 µm PDMS fibre into water of 0.25 cm/s at 25° C. Although the sum of $$\frac{Q}{q_0}$$

and $$\frac{n}{n_0}$$

at any time is close to 1, there is a tendency for the value to be slightly smaller than 1. We ascribe this to the slight difference of physicochemical properties between deuterated toluene and toluene. The difference could be corrected by knowing the difference of the physicochemical properties between the standard and target analytes.

Experimental Details: Chemicals, Supplies, and Standard Mixtures. All chemicals were of analytical grade. Benzene, toluene, ethylbenzene and o-xylene (BTEX) were purchased from Sigma-Aldrich (Mississauga, ON, Canada). HPLC grade methanol was purchased from BDH (Toronto, ON, Canada), and naphthalene, acenaphthene, and fluorene were purchased from Supelco (Oakville, ON, Canada). Deuterated toluene (d-8) was purchased from Cambridge isotope laboratories (Andove, Mass., U.S.A.). The SPME holders and 100 □ m polydimethylsiloxane (PDMS) fibers were obtained from Supelco. The fibers were conditioned at 250° C. for 1 h prior to their use. All preparations involving toluene, ethylbenzene, and p-xylene (flammable and toxic), benzene (suspected carcinogen), naphthalene, acenaphthene, and fluorene (suspected carcinogen) were carried out in a ventilated fume hood. The systems for generating the standard BTEX gas mixture and the standard BTEX and PAHs aqueous solutions have been previously described (Koziel, J. A.; Martos, P. A.; Pawliszyn, J. *J. Chromatogr. A* 2004, 1025, 3-9).

*Gas Chromatography.* A Varian star computer-controlled Varian 3400 CX gas chromatograph (Varian Associate, Sunnyvale, Calif.) equipped with a carbon dioxide cooled septum-equipped programmable injector (SPI) was used for the BTEX analysis. A 0.8 mm i.d. SPI insert was coupled to a RTX-5 column (30 m, 0.25 mm i.d., 1.0 µm film thickness) and the column was coupled to a flame-ionization detector (FID). The injector was maintained at 250° C. for the PDMS fiber injection. The column temperature was maintained at 35° C. for 2 min and then programmed at 30° C./min to a maximum of 230° C. The carrier gas (helium) head pressure was set to 25 psig (~172 kPa).

A Saturn 3800 GC/2000 ITMS system fitted with a HP-5 column (30 m, 0.25 mm i.d., 0.25 µm film thickness) (Hewlett-Packard, Avondale, Pa.) was used for the analysis of deuterated toluene and PAHs. Helium, as the carrier gas, was set to 1 mL/min. The 1079 injector was set to 250° C. for deuterated toluene and 270° C. for PAHs, and a desorption time of 1 min for deuterated toluene and 10 min for PAHs. For the analysis of deuterated toluene, the column temperature was maintained at 45° C. for 2 min and then programmed at 20° C./min to a maximum of 180° C. For the analysis of PAHs, the GC split valve was set to open after 5 min of insertion. The column temperature was maintained at 45° C. for 2 min and then programmed at 20° C./min to a maximum of 280° C., and held for 5 min. The MS system was operated in the electron ionization (EI) mode, and tuned to perfluorotributylamine (PFTBA). A mass scan from 40 to 300 was acquired, and the base peak of each compound was selected and integrated.

Discussion: This experiment discussed above (see FIG. 28) proved the isotropy of the absorption and desorption of an analyte onto and from a SPME fibre. The resulting implication is that by knowing the behaviour of either the absorption or desorption, the opposite process will also be understood. The practical implementation of this approach is straightforward. To determine the concentration of an analyte in a sample matrix, a known amount of isotopically labelled analogue is extracted onto a SPME liquid coating fibre. Then the fibre is exposed to the sample matrix for a certain time, during which a part of the isotopically labeled analogue is desorbed from the fibre and a certain amount of the analyte is absorbed onto the fibre. The constant a from desorption allows for the calibration of absorption. This approach should be, in principle, suitable for calibration extraction of target components from different matrices, including blood and biological tissues. One of the main objectives of this research program would be to demonstrate the suitability of this approach for in-vivo determinations.

In the least disruptive variant of this approach, the standards will be added to balance the analyte loss from the matrix during extraction. This objective is accomplished by adding an amount of the standard equal to the amount of analyte being removed from the matrix. This condition requires a good estimation of the concentrations, but it could be useful in investigations to verify models or previous experiments. The standard can be an isotopically labelled analogue of the target analyte, to minimize impact on the investigated system.

Figure 29:
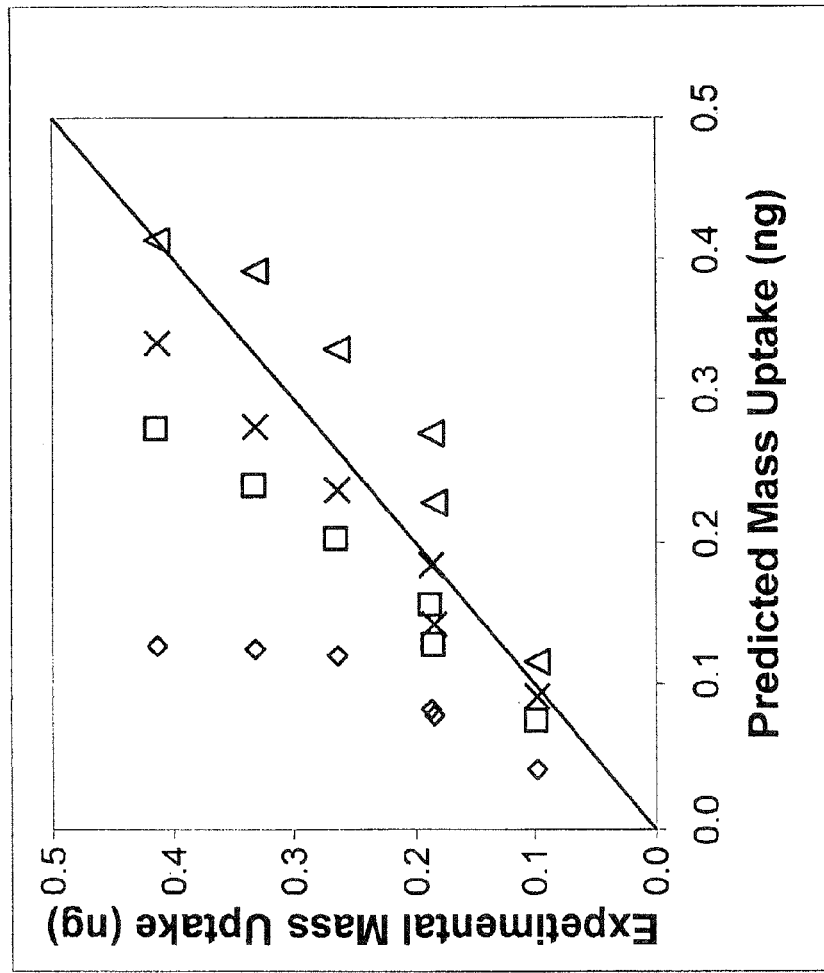
FIG. 29 shows validation of the calibration of uptake of component (fluorine) by use of desorption of calibrants (benzene, toluene, ethylbenzene and xylene).

In case an isotopically labelled analogue of the target analyte is not available, or there is more than one target analyte, a more universal approach will be developed, based on only one reference compound loaded onto the extraction phase, and mass transfer coefficients or constants a of target analytes will extrapolated from that of the standard, based on diffusion mass transfer [Cussler, E. L., Diffusion: mass transfer in fluid systems. New York: Cambridge University Press, 1997.]. However the calibrant physicochemical properties should be similar to the analyte of interest to ensure that the extraction rate limited step is similar for both compound of interest and the calibrant. FIG. 29 shows that calibration for extraction of fluorene works well when toluene, ethylbenzene and xylene is used, but not when benzene is used.

Figure 30:
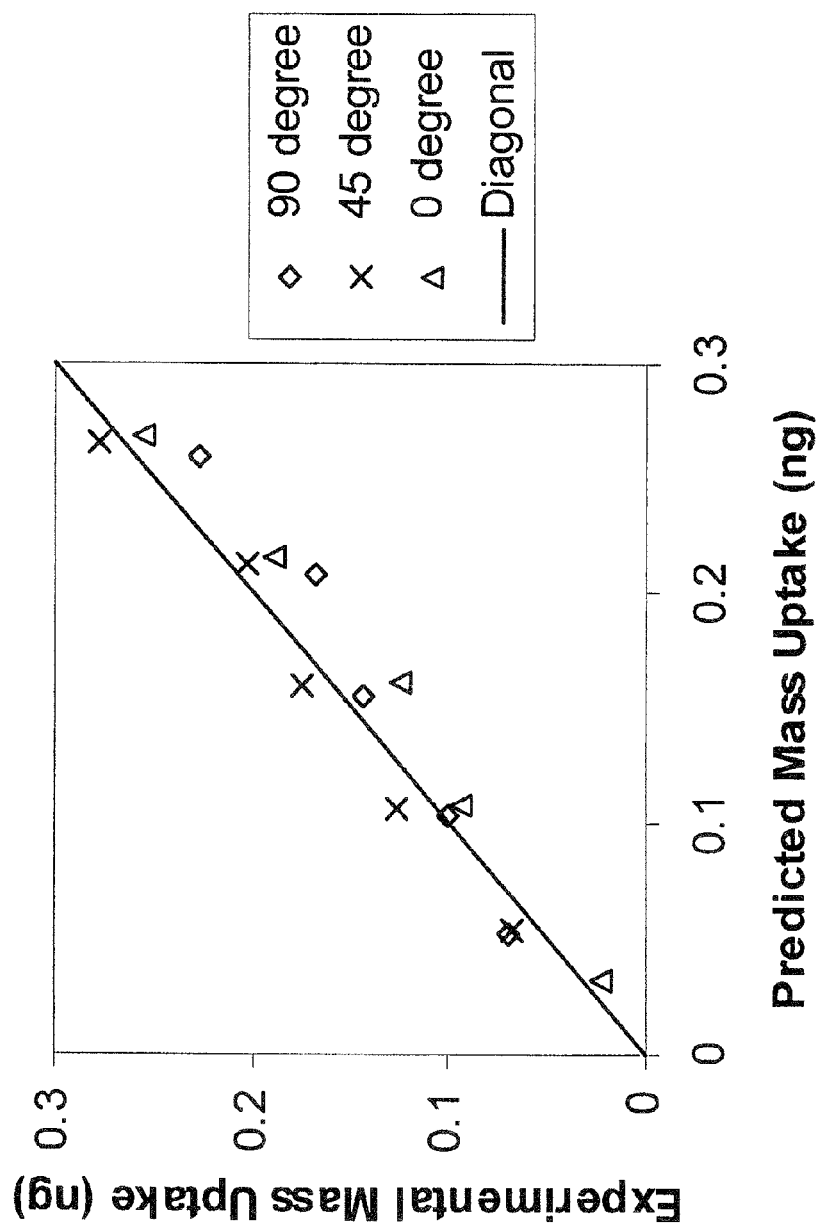
FIG. 30 calibration of the uptake of component (fluorine) at various orientation of PDMS coated fibre by use of desorption of calibrant (xylene).

The isotropy of absorption and desorption of an analyte onto and from an extraction phase is independent of the geometry of the extraction phase and the orientation of the extraction phase and sample matrix, which allows for the use of specially designed extraction phases for some challenging applications, such as in-vivo analysis. FIG. 30 illustrates calibration of the uptake of fluorene onto a 100 µm PDMS fiber by the desorption of o-xylene from the same fiber into a standard PAHs aqueous solution at a rate of 1.2 cm/s (at 25° C.), when the axis of the fiber is in different orientations to the flow direction of the standard solution. This approach to calibration compensate for different orientation of the extraction phase.

Example 7

Time-Weighted Average Field Water Sampling Using Extraction with Rod or Membrane Made of Polydimethylsiloxane (PDMS) with Calibrant in PDMS Studies have been conducted to see if larger volume and capacity samplers, such as PDMS rod or membrane can be used in combination with the calibrant in the extraction phase approach. Comparing to the commercial PDMS fiber, PDMS membrane and PDMS rod, the rod and the membrane configurations have several advantages for on-site monitoring, such as larger capacity, higher sensitivity, more flexibility and lower cost. The advantage membrane is higher rate of extraction because of the high surface area to volume ratio. To calibrate the environmental factors, such as temperature, turbulence etc., the on-rod internal standardization method is applied, in which the standard was loaded to the rod or membrane before introducing to the field sample. The isotropy of absorption and desorption in PDMS rod allows for the calibration of absorption using desorption. In the other word, the absorption of the target analytes can be calibrated by the desorption of the calibrant preloaded on the rod or membrane. In the example below we discuss the performance of the rod configuration. Membrane configuration gives similar results with benefits of the higher rates.

Experimental: Chemicals and Supplies

All chemicals were of analytical grade. The solvent methanol was obtained from BDH (Toronto, ON, Canada) with HPLC grade. The 100 ppm stock solution in methanol was prepared using pure solid standard of d10-pyrene purchased from Sigma-Aldrich (US). PAHs were purchased from Supelco (Oakville, ON, Canada). Milli-Q water was obtained by purification and deionization of tap water immediately prior to use with a Deralpur PRO 90 CN (Seral, Germany). The pure PDMS rod was also supplied by Supelco which has the diameter of 1 mm. The length of 1 cm, which corresponds to about 7.85 µl of PDMS, was chosen in the current study with the consideration of the length of the liner. The PDMS rod was conditioned at 250° C. for 4 hours prior to its first use. The blank run showed that there is no target PAHs on the rod after the conditioning. For the flow-through system, the temperature of the mixer chamber is controlled at 30° C. by using a temperature controller (Omegalux, US) to minimize the effect of the temperature on the system.

GC-MS: A Saturn 3800GC/2000 ITMS (Varian Associate, Sunnyvale, Calif.) system equipped with a carbon dioxide-cooled septum-equipped programmable injector (SPI) was used for the PAHs analysis. A SPI liner (2.4 ID*4.6 OD*54 mm) with buffer coupled to a SPB-5 column (30 m, 0.25 mm i.d., 0.25 μm film thickness) (Supelco, Mississauga, ON, Canada) was used. Helium was used as the carrier gas with the flow rate of 1 mL/min. In order to put the rod into the injector, temperature program is applied with the initial temperature at 40° C. and then increased to 250° C. at a rate of 100° C./min. The column temperature was maintained at 40° C. for 2 min and then programmed at 30° C./min to 250° C., and held for 5 min and them programmed at 30° C./min to 280° C., and held for 15 min. The total run time is 30 min. The MS system was operated in the electron ionization (EI) mode, and tuned to perfluorotributylamine (PFTBA). Mass scan from 40 to 300 was acquired, and the base peak of each compound was selected and integrated.

The instrument was checked on a daily basis by calibration with a liquid midpoint calibration standard. Any deviation in area counts greater than 15% required re-injection of that standard; if then the deviation was still greater than 15% the instrument was recalibrated with a six-point calibration plot. Peak shape quality, resolution, and retention times were also carefully monitored to ensure all chromatography was within all required specifications.

Discussion: Standard Loading Method:

The first challenge to perform the current research is to find out a suitable standard loading method, which is fast, simple and reproducible. The headspace extraction of the calibrant dissolved in solvent or pumping oil used previously for more volatile calibrants is not very suitable in the current study since the extraction amount would be too low and the extraction time would be extremely long to obtain enough loading amount due to the low volatility of PAHs. Development of an appropriate method was performed using deuterated pyrene as the standard for loading. To load the appropriate amount of deuterated pyrene with high reproducibility, the loading was performed by putting the rod directly in the standard solution with agitation in this study. The extraction time was set as half an hour and the reproducibility was good which was lower than 7%. Three rods were involved in this study and the RSDs for the extraction by all the three rod are listed in Table 3. The amount of the standard loaded onto the rod can be also adjusted by changing the concentration of standard loading solution and extraction time.

Absorption of the PDMS Rod:

In order to determine the sample concentration, $q_0$ need to be clarified before the sampling. To perform the extraction, 10 ppb standard solution was prepared by spiking 1 μl 100 ppm deuterated pyrene (calibrant) into 10 ml deionized water containing in 10 ml vial. The rod was introduced into the vial with a stir bar stirring at 1000 rpm. After certain extraction time, the rod was taken out form the solution with tweezers, dried with lint-free tissue and then immediately transferred to the GC injector for analysis. It was found that the extracted mass of deuterated pyrene increases linearly initially and reached stable level after extracting for more than 2 hrs. Comparison with the results of direct syringe injection of 1 μl 100 ppm pyrene-d10 into the GC injector indicates that the extraction is an exhaustive extraction due to the high capacity of the rod.

Figure 31:
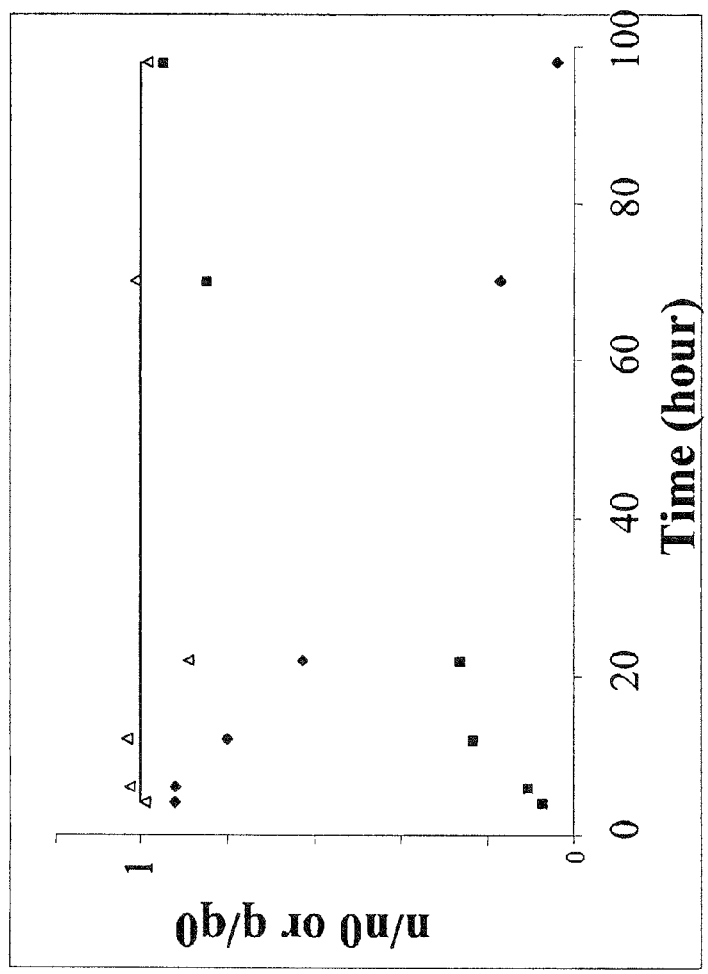
FIG. 31 shows isotropy of absorption of pyrene (component) and desorption of deuterated pyrene (calibrant) for long exposure of PDMS rod.

Isotopic of the Absorption of the Analytes and Desorption of the Standard:

Experiments were conducted to validate the existence of the isotopic of the absorption of the analytes and the desorption of the standard. The experiment involved the simultaneous determination of the desorption time profile of deuterated pyrene as the calibrant and the absorption time profile of pyrene as the component. The rod was preloaded with deuterated pyrene and then exposed to the flow-through system with different exposure time. FIG. 31 shows the value of $$\frac{q}{q_0}$$

calculated from the resulting desorption time profile, the value of $$\frac{n}{n_0}$$

calculated from the resulting absorption time profile, and the sum of $$\frac{q}{q_0}$$

and $$\frac{n}{n_0}$$

at any time is close to 1, which demonstrate the isotopic of the absorption and desorption for long times (100 h). The isotropy of the absorption and desorption on the rod allows the calibration of absorption of the analytes by the desorption of the standard. This approach is especially important for the calibration of on-site analysis. In particular if the thick extraction phase is used this example demonstrates that the desorption of the calibrant from high capacity extraction phase can persist for long period of time, which facilitate calibration of long exposure times including TWA sampling. The concentrations of PAHs in the flow-through system were determined by using PDMS rod extraction and on-rod internal standardization method. The concentrations determined by this new calibration approach agree well with the results obtained from external calibration method, which demonstrated the feasibility of this approach to the field water sampling.

Example 8

Equilibrium In-Fibre Standardisation Technique for Solid-Phase Microextraction

This example describes an exemplary solid phase microextraction using a standard loaded into the fibre coating as a means of internal standardisation for the analysis of samples contained in vials. Reproducible amounts of standards were loaded into a SPME non-porous fiber. It was found that spiking a few microliters of liquid standards such as benzene, toluene, ethylbenzene, and xylenes (BTEX) and/or adding a few milligrams of solid standards such as naphthalene into few grams of pump oil sealed in a 20 milliliter vial provided an excellent standard generator, and allowed for reproducible loading of standards (RSD<4%) up to hundreds of times. When standards were introduced into a sample vial together with a fiber, extraction of analytes into the fiber and desorption of the standards into the sample matrix occurred simultaneously. Quantification was then based on the equilibrium distribution of the standards and the analytes between the fibre coating and the sample matrix in the vial. A comparison of equilibration profiles obtained using traditional internal standardisation and the in-fibre approach generally showed the same equilibration behaviour. This method, according to one aspect of the invention was successfully used to correct for matrix effects in the BTEX analysis of a wine sample.

Introduction. Internal standardisation is a well known calibration approach in analytical chemistry that is used to improve the accuracy and precision of experimental data to account for such factors as sample matrix effects, losses during sample preparation, and irreproducibility in such parameters as sample injection in GC (Haefelfinger, Chromatogr, 1981, 218, 73-81). Solid-phase microextraction (SPME) as a sample preparation and extraction technique is no exception, with internal standardisation often used for quantification particularly when analysing complex samples. However, the addition of an internal standard provides an additional step in sample preparation. For completely automated analysis, two robotic arms are required, one to provide the standard spike and the other for SPME. There are also situations in which the addition of an internal standard is not practical, such as on-site or in-vivo applications.

SPME is a solvent free technique designed for rapid sampling and sample preparation. (Pawliszyn, J. Solid Phase Microextraction Theory and Practice; Wiley-VCH: Chicester, 1997). The most common form of the technique uses a fibre coated with a liquid polymeric film, which is exposed to the sample, extracting analytes from it until equilibrium is reached. The amount of analyte absorbed by the coating at equilibrium ($n_f$) is linearly proportional to the initial concentration in the sample ($C_0$) by eq 8:

$$n_f = \frac{K_{fs} V_f V_s}{K_{fs} V_f + V_s} C_0 \qquad (8)$$

where $K_{fs}$ is the fibre/sample distribution coefficient, $V_f$ is the volume of the fibre coating and $V_s$ is the volume of the sample. For analysis in a vial containing headspace this equation should be expressed as shown in eq 9:

$$n_f = \frac{K_{fs} V_f V_s}{K_{fs} V_f + K_{hs} V_h + V_s} C_0 \qquad (9)$$

where $K_{hs}$ and $V_h$ represent the headspace/sample distribution coefficient and the volume of the headspace, respectively.

The fact that SPME is an equilibrium rather than an exhaustive extraction technique means that even after the extraction process has been completed a substantial portion of the analytes usually remain in the matrix. This presents an opportunity for quantification based on internal standardisation, namely that the standard is loaded onto the fibre prior to the extraction step, instead of spiked into the sample. Example 6 have explored the kinetics of the technique, demonstrating that the absorption and desorption processes are isotropic, which allows for calibration of the rate of absorption using the rate of desorption.

The current example aimed to expand on this technique to fundamentally assess the in-fibre standardisation approach with systems reaching equilibrium. The in-fibre standardisation approach was developed for automated sampling from milliliter quantities of liquids in vials and used for the analysis of BTEX in a wine sample.

Theoretical Considerations. The equilibrium equation for SPME, most generally described by eq 7 is derived from the knowledge that the amount of analyte in the system will remain the same before and after the extraction. This mass balance equation can therefore be expressed by eq 10:

$$n_T = n_f + n_h + n_s \qquad (10)$$

where $n_T$ is the total number of moles of analyte in the system, and the remaining terms denote the amount of the analyte in the fibre, headspace and sample respectively at equilibrium. Using this form of expressing the mass balance, leads to eq 11:

$$n_f = \frac{K_{fs} V_f}{K_{fs} V_f + K_{hs} V_h + V_s} n_T \qquad (11)$$

From this equation, it is apparent that no matter where the standard or analyte of interest starts in the system, at equilibrium the amount in the fiber should be the same.

A further consideration is the kinetics of the process. For traditional SPME the kinetics for both direct and headspace extraction can be described by eq 12 (Ai, J. Anal. Chem. 1997, 69, 3260-3266; Ai, J. Anal. Chem. 1997, 69, 1230-1236):

$$\frac{n}{n_f} = 1 - \exp(-at) \qquad (12)$$

where n is the moles of analyte in the coating at time t, a is a constant that is dependant on the volumes of the fibre, headspace and sample, mass transfer coefficients, distribution coefficients and the surface area of the fibre. The kinetic processes involved for desorption of analytes from the fibre coating is defined by eq 13:

$$q = n_0 \frac{V_s}{K_{fs} V_f + V_s} [1 - \exp(-at)] \qquad (13)$$

where q is the moles of the analyte lost from the coating at time t and $n_0$ represents the moles of the compound originally loaded. For the case of in-vial analysis the moles remaining on the fibre (n) at time t can be expressed as $$n = n_0 - q \qquad (14)$$

From eqs 13 and 14 it is apparent that $$n = n_0 - n_0 \frac{V_s}{K_{fs} V_f + V_s} + n_0 \frac{V_s}{K_{fs} V_f + V_s} \exp(-at) \qquad (15)$$

However, as the exponential term disappears as time goes to infinity, therefore $$n_f = n_0 - n_0 \frac{V_s}{K_{fs} V_f + V_s} \qquad (16)$$

Substituting eq 16 into eq 15 and rearranging gives $$\frac{n - n_f}{n_0 - n_f} = \exp(-at) \qquad (17)$$

Comparing eq 17 with eq 12, it can be concluded that for in-vial analysis the isotropy of absorption and desorption of an analyte from the fibre still maintains. A similar expression can be derived for headspace analysis with a suitable adjustment in the definition of a.

Experimental: Materials. Ethylbenzene-$d_{10}$ (99+%), ethyl benzene, o-xylene (98%, HPLC grade), naphthalene (99+%, scintillation grade) and carbon disulfide (99.9+%, HPLC grade) were purchased from Sigma-Aldrich (Milwaukee, Wis., USA). Benzene (analytical reagent) was from BDH Inc. (Toronto, ON, Canada), toluene (Guaranteed Reagent) from EMD (Gibbstown, N.J., USA), $D_8$-Naphthalene (99%) from Cambridge Isotope Laboratories Inc. (Andover, Mass., USA). HPLC grade methanol was obtained from Fisher Scientific (Nepean, ON, Canada), the vacuum pump oil was supplied by BOC Edwards (Wilmington, Mass., USA), and the poly(dimethylsiloxane) (PDMS) membrane material was supplied by Specialty Silicone Products Inc. (Ballston Spa, N.Y., USA). PDMS (100 μm) SPME fibres and Tenax (TA80/100 mesh) were purchased from Supelco (Bellefonte, Pa., USA). Water purified from a Barnstead ultrapure water system (Dubuque, Iowa USA) was used throughout. All gases were supplied by Praxair (Kitchener, ON, Canada) and were of ultra high purity. Ten or twenty milliliter sample vials were used for automated analysis with magnetic crimp caps and PTFE coated silicone septa (Microliter Analytical Supplies, Suwanee, Ga., USA). The dry white wine sample was obtained from a local liquor store.

GC Analysis. Gas chromatography was performed on a Varian™ (Mississauga, ON, Canada) 3800 gas chromatograph coupled with a Saturn™ 2000 MS system controlled by computer using Varian Saturn Workstation software (ver. 5.51) or with a FID detector using Star Chromatography Workstation (ver 5.51). Automated analysis was performed using a CTC CombiPal™ autosampler (Zwingen, Switzerland) using the associated Cycle Composer™ software (ver 1.4.0). The PAL was equipped with a SPME fibre holder, a temperature controlled six vial agitator tray and a fibre conditioning device. Separation was performed using a 30 m×0.25 μm×0.25 mm I.D. Rtx-5MS fused silica column from Restek (Bellefonte, Pa., USA). For analysis of BTEX the column was initially set at 40° C. for 4 minutes and then ramped at 15° C./min to 130° C. giving a total run time of 10 minutes. The injector was set at a temperature of 250° C. and helium was used as the carrier gas at a flow rate of 1 mL/min. For analysis of naphthalene, the column was initially set at 40° C. for 1 min and then ramped at 20° C./min to 220° C. giving a total run time of 10 min. The temperature of the injector was set at 250° C. and helium was used as the carrier gas at a constant pressure of 12 psi. For both analytes a 1 minute desorption time in the GC injection port was used, which was immediately followed by a 2 minute bake-out at 250° C. in the autosampler fibre conditioning device.

FID was used at a temperature of 300° C. with gas flows for hydrogen, high purity air and make-up gas (nitrogen) set at 300, 30 and 25 ml/min respectively. For the mass spectrometry detection experiments, electric ionisation was used with temperatures of 170, 50 and 260° C. for the trap, manifold and transfer line respectively. A scan range of 70 to 125 m/z was used and quantification was performed using 78 m/z for benzene, 91 for toluene, 98 and 116 for deuterated ethyl benzene and 91 and 106 for ethyl benzene and o-xylene. For naphthalene, a scan range of 100 to 160 m/z was used and quantification was performed using 128 m/z for naphthalene and 136 m/z for deuterated naphthalene.

For the automated analysis a sampling temperature of 35° C. was used. The internal standard was loaded onto the fibre by exposure to the headspace of a 20 mL sample vial containing 4.00 g of vacuum pump oil spiked with deuterated ethyl benzene at a concentration of 0.47 mg/g. The loading time was 1 minute with an agitation speed of 500 rpm. The fibre was then immediately exposed to the headspace of a 10 mL vial containing the sample for 5 minutes, again using a 500 rpm agitation speed. The sample volume used unless otherwise specified in these experiments was 3.0 mL. A 6 minute pre-extraction equilibration of the sample was performed in the agitation unit at 500 rpm. For loading of naphthalene, a 2.00 g solution pump oil was used containing 2.0 mg/g naphthalene. All other conditions were the same as in the ethyl benzene experiments unless otherwise specified.

Addition of Standard Spike to Vials. Standards used for constructing calibration curves and sample "spikes" to test the method were prepared by spiking the sample with a standard of the target compounds prepared in methanol. Initially this was done after the vial had been capped by means of a 10 or 100 μL syringe. However, using this approach a steady decline in peak areas for the analytes was observed that was related to the amount of time between spiking and sampling. The decline was worse with ethyl benzene and xylene than with benzene and toluene. This suggested the behaviour was caused by absorption of the compounds into the small part of the vial septum silicone layer exposed through addition of the standard spike. To overcome this difficulty it was necessary to spike the solutions prior to capping. To minimise evaporation it was necessary to add the spike below the level of the solution in the vial, a similar approach to that adopted for standard preparation in EPA method 5021A (US Environmental Protection Agency, Method 5021A: Volatile Organic Compounds in Various Sample Matrices Using Equilibrium Headspace Analysis, 2003).

Results and Discussion: Internal Standard Loading on Fiber. The first challenge was to find a method that would allow, automated, fast and reproducible loading of the standard into the fiber. Development of an appropriate method was performed using ethyl benzene as the "standard" for loading. Sampling from the headspace of a vial containing pure ethyl benzene resulted in unmanageably high loading on the fiber coating even for extremely short absorption times. This was true even when cooled to 5° C. in the sample tray. The use of diluted solutions of ethyl benzene in water to reduce the loading to an acceptable level showed that the mass of ethyl benzene withdrawn from the vial during each loading step was a significant percentage of the total. This made it impossible to reuse a "loading" vial, which is not practical in terms of the number of standard solution vials required for a automated sample list. The use of alternative techniques, such as vials containing ethyl benzene absorbed onto Tenax, or PDMS membrane showed similar problems. Injecting the needle into a headspace of a vial containing pure ethyl benzene, but not exposing the fiber coating showed a workable and reproducible loading, except the needle sometimes being blocked with a piece of septum.

Finally, a system was adopted whereby the ethyl benzene was dissolved in vacuum pump oil, to reduce the $K_{fs}$ partition coefficient for the standard into the fiber. Using this method gave an acceptable and reproducible loading with 1 min exposure to the standard solution headspace. This also worked well for naphthalene. The amount loaded into the fiber can be further adjusted by spiking different amount of the standard into the vacuum pump oil and/or exposing the fiber for different time. Using this approach, each loading cycle only withdrew 0.0087% of the ethyl benzene in the vial, making it possible to use the vial for at least 115 injections before 1% of the vial contents had been removed. Reproducibility of the loading step for ethyl benzene determined by FID was 1.9% for 40 injection cycles, whilst the value was 2.6% for loading followed by equilibration with a vial containing 3 mL of water for 10 minutes in 20 injection cycles. For naphthalene loading reproducibility was 2.0% for 30 injection cycles, whilst the value was 3.6% for loading followed by equilibration with a vial containing 3 mL water for 10 min in 20 injection cycles. In theory, the standard solution can be used at least 300 times before 1% of the vial contents had been removed.

Comparison of Equilibrium Curves. As a first investigation of the approach, equilibration profiles using traditional SPME and in-fiber standardisation SPME for ethyl benzene and naphthalene were compared when exposed to empty 10 mL headspace vials, (actual volume was determined to be 11.5 mL). The two processes were also investigated using direct immersion of the fiber in vials filled with water and headspace experiments in vials containing 3 mL of water. Under the conditions studied the equilibration time was not influenced by the location of the standard at the beginning of the equilibration process.

Applications to Real Sample Matrices. To test the in-fibre standardisation method, the technique was used to examine BTEX in spiked white wine with MS detection. The method was linear for BTEX compounds over the tested range of 0.09-73 µg/L. For all of the compounds, the linearity was higher than 0.9998 in both the calibration curves and the curves normalized by internal standard. The recoveries from wine spiked with 7.3 µg/L BTEX, calculated using external calibration and the in-fibre standardisation approach are given in Table 2. Deuterated ethyl benzene was used as the internal standard.

TABLE 2

Recoveries for BTEX in White Wine

| Compound | Recovery calculated using external calibration (%) | Recovery calculated using internal standard in the fibre (%) |
| --- | --- | --- |
| Benzene | 81.2 ± 5.2 | 102.3 ± 5.8 |
| Toluene | 83.2 ± 0.7 | 105.1 ± 0.2 |
| Ethyl Benzene | 76.8 ± 1.0 | 99.3 ± 0.6 |
| o-Xylene | 72.1 ± 1.5 | 91.2 ± 1.3 |

It was demonstrated that the in-fibre technique gives improved recovery for the determination of these compounds than seen using external calibration. With $d_{10}$-ethylbenzene as internal standard, 99% recovery was obtained for ethylbenzene. The slightly higher deviations from 100% recovery for the other analytes can largely be attributed to differences in the interactions of these compounds with the matrix compared to the internal standard.

Conclusions. From this example, it is confirmed that the in-fibre standardisation approach works successfully under equilibrium conditions and can be easily automated. The developed procedure requires only a single arm autosampler, unlike SPME with traditional internal standardisation that requires a dual arm system. Equilibration time was not affected by where the standard commenced in the system. The technique was applied to the analysis of BTEX in wine, successfully correcting for matrix effects. This method can also be used with other equilibration extraction techniques, such as liquid phase microextraction (LPME) or membrane extraction.

Example 9

Standards in Liquid Phase for Liquid-Phase Microextraction

This example describes an exemplary liquid phase microextraction (LPME) using a standard loaded into extraction liquid as a means of internal standardisation for the analysis of samples contained in vials. Information about LPME techniques can be found in following references: E. Psillakis and N. Kalogerakis. Developments in single-drop microextraction. *Trends Anal. Chem.* 2002, 21, 54-64 and K. E. Rasmussen and S. Pedersen-Bjergaard Developments in hollow fiber-based, liquid-phase microextraction. *Trends Anal. Chem.* 2004, 23, 1-10. The kinetics of the absorption and desorption of analytes for a variant of LPME single-drop headspace liquid-phase micoextraction (SD-HS-LPME) were studied. Procedures used in other variants of the LPME technique are analogues. It was found that the desorption of calibrant from the extraction phase into sample matrix is isotropic to the absorption of analyte (component) from the sample matrix into the extraction phase under the same conditions, which allows for the calibration of absorption using desorption. The calibration was accomplished by exposing the extraction phase, pre-added with a standard, to the sample matrix. The information from the desorption of standard, i.e., time constant a, could be directly used for estimating the concentration of the target analyte in the sample matrix. The developed kinetics calibration method of headspace LPME was successfully used to correct the matrix effects in the BTEX analysis of orange juice sample. In this study, headspace LPME technique, for both static and dynamic, was successfully automated by using a CTC CombiPal autosampler. All operations of headspace LPME, include sample transfer and agitation, filling of extraction solvent, exposing the solvent in the headspace, withdrawing the solvent to syringe and introducing the extraction phase into injector, were auto performed by the CTC autosampler. The fully automated headspace LPME technique is more convenient and improves the precision and sensitivity. This automated headspace LPME technique can be also used to obtain the distribution coefficient between the sample matrix (aqueous or other solution) and the extraction phase (1-octanol or other solvent). The distribution coefficient between 1-octanol and orange juice at 25° C. was obtained by using this technique.

Chemicals and Supplies. All chemicals were of analytical grade. Benzene, $d_6$-benzene, toluene, $d_8$-tuluene, ethylbenzene, o-xylene, 1-octanol (HPLC, 99+%) were from Sigma-Aldrich (Mississaga, ON, Canada). HPLC grade methanol was purchased from BDH (Toronto, ON, Canada). Hamilton Model 701N10 µL syringes (26s gauge, no. 2 point style bevel tip) were purchased from Hamilton (Reno, Nev., USA). 10 mL screw vials with magnetic crimp caps and PTFE coated silicone septa (Supelco, Oakville, ON, Canada) were used for automated analysis. Water purified from a Nanopure filter (Barnstead, Dubuque, Iowa, USA) was used throughout. Ultra high purity helium was supplied by Praxair (Kitchener, ON, Canada). The orange juice sample was purchased from a local supermarket.

Instrument. A Saturn 3800 GC/2000 ITMS system fitted with a SPB-5 column (30 m, 0.25 mm i.d., 0.25 µm film thickness) (Supelco, Mississauga, ON, Canada) was used for the analysis of BTEX. Helium as the carrier gas was set to 2 mL/min. The column temperature was maintained at 80° C. for 1 min and then programmed at 20° C./min to 120° C., and then programmed at 50° C./min to 250° C., and held for 4.4 min. The total run time was 10 min. An i.d. 2 mm liner packed with glass wool was used for the 1079 injector. The injector was set to 250° C. with a split ratio of 10:1. The syringe will hold 10 second in the injection after sample was injected. The MS system was operated in the electron ionization (EI) mode, and tuned to perfluorotributylamine (PFTBA). The EI was set to turn on at 1 min and turn off at 3 min (before the elution of solvent). A mass scan from 40 to 120 was used and quantification was performed using m/z 78 for benzene, m/z 84 for $d_6$-benzene, m/z 98 for $d_8$-toluene and m/z 91 for toluene, ethylbenzene, and o-xylene.

Extraction and desorption procedure. All extraction procedure was performed with a CTC CombiPal autosampler (Zwingen, Switzerland) using the associated Cycle Composer software (ver 1.4.0). An 870 ppm stock solution of BETX components was prepared in methanol. 870 ppb standard solutions of BTEX were prepared daily by spiking the stock solution to pure water with a CTC autosampler. To avoid the effect of time, the solution was spiked prior to capping and the spike was added below the level of the water in the vial.

The extraction of analytes in the sample and the desorption of internal standard were performed in a 10 mL vial, containing 3 mL 870 ppb BTEX aqueous solution, for the determination of adsorption profile, or 3 mL pure water, for the determination of desorption profile. The single-drop extraction phase were 1 μL 1-octanol, for the determination of adsorption profile, or 1 μL 1-octanol containing 870 ppm internal standard (BTEX or $d_6$-benzene and $d_8$-toluene), for the determination of desorption profile.

For static SD-HS-LPME, the 10 mL sample vial was transferred from sample tray to the vortex agitator with temperature controller, shaking 2 min at 500 rpm, then the Hamilton 701 10 μL syringe, filled with 1 μL 1-octanol, pierced the septum and slowly exposed the 1 μL 1-octanol (0.1 μL/s) in the headspace of sample vial. After different extraction time, the 1 μL 1-octanol was slowly withdraw to the barrel (0.1 μL/s) and was introduced to GC/MS to analysis.

For dynamic SD-HS-LPME, the sample vial was also shook 2 min at 500 rpm in the vortex agitator, then the Hamilton 701 10 μL syringe, filled with 1 μL 1-octanol, pierced the septum and the plunger was slowly depressed to expose the 1 μL 1-octanol (0.1 μL/s) in the headspace of sample vial and then the 1 μL 1-octanol were immediately withdrew to the barrel of the syringe. The sample vial was then shook 10 second at 500 rpm, the 1 μL 1-octanol was exposed and withdrew again. This procedure was repeated different times before the 1 μL 1-octanol were introduced to GC/MS. (Caution: due to the needle of the syringe will shaking with sample vial when perform the dynamic operation, the dynamic program must to be carefully set, otherwise the needle of syringe will be easy damaged. The best program is like the operation of CTC autosampler for headspace SPME. The syringe can be used hundreds times still keep good condition if the program was optimized.)

Quantification. The solvent for preparing standard solution will obviously affect the sample transfer into the column of GC, especially the standard solution was introduced to high temperature injector. In this study, it was found that the peak areas of BTEX for 870 ppm methanolic solution, compared with the peak areas of BTEX for 870 ppm 1-octanolic solution, were just about 50%. To avoid the effect of solvent for the quantification, the standard solutions for calibration also were prepared with 1-ocatanol. Good precision (RSD<5%) and linearity ($R^2$>0.999) were obtained for the calibration curves.

Analysis of BTEX in Orange Juice. The recoveries from orange juice spiked with 870 ppb BTEX calculated against with external calibration (standards prepared in water) and kinetics calibration approach (time constant a was determined at first, and the exposition-withdrawal-agitation procedure was repeated 5 times when perform the determination of real sample) are given in Table 3. The results demonstrate that the kinetic calibration technique gives more accurate determination of these compounds than external calibration.

TABLE 3

Calculated recoveries of BTEX from orange juice with and without calibration with single drop extraction.

| | Relative recovery (%) (RSD, %; n = 3) | |
|---|---|---|
| Compound | Using external calibration | Using kinetic calibration |
| Benzene | 121 (5.3) | 99 (5.8) |
| Toluene | 97 (4.6) | 94 (3.5) |
| Ethylbenzene | 73 (5.7) | 91 (5.6) |
| o-Xylene | 73 (6.3) | 95 (3.5) |

Example 10

Membrane Extraction with Calibrant in the Stripping Fluid

This example describes a new technique for calibration in membrane extraction processes, by adding an analytically non-interfering internal calibrant in the stripping fluid. Description of membrane techniques can be found in the following reference: Jönsson, J. Å., Mathiasson, L. *J. Chromatogr. A* 2000, 902,205-225. A membrane extraction with sorbent interface (MESI) system was used to evaluate this approach. Description of membrane techniques can be found in the following reference: Lord, H., Yu, Y., Segal A., Pawliszyn J. *Anal. Chem.* 2002, 74, 5650-5657. During membrane extraction, the internal calibrant from within the carrier (stripping) gas and the target analyte from the sample matrix will permeate simultaneously through the membrane in opposite directions. The change of the accumulation amounts of internal calibrant in the microtrap can be used as a means of calibration to correct for the variation of the extraction rate due to variable environmental factors, such as the sample feed velocities and the temperature of the membrane. Thus, this approach should allow for more accurate estimates of target analyte concentrations for complicated sampling conditions.

Figure 32:
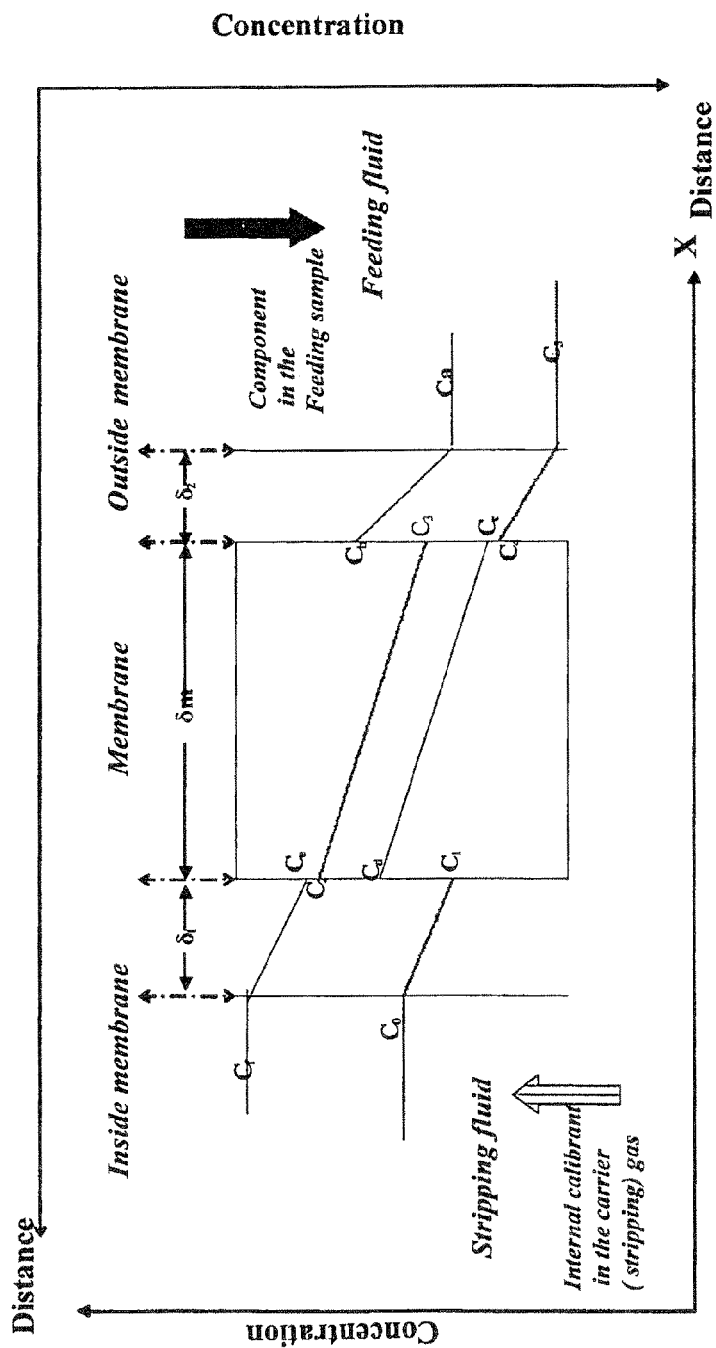
FIG. 32 illustrates concentration profiles in membrane extraction.

Theory: The permeation of analytes through a nonporous polymer membrane is generally described in terms of a "solution-diffusion" mechanism, which consists of seven consecutive steps (FIG. 32). Permeation rates are independent of whether the receiving chamber contains a vacuum or a gas other than the penetrant. Therefore, the internal calibrant, from the carrier(stripping) gas, and the target analyte, from the sample matrix, will permeate simultaneously through the membrane in opposite directions. When the diffusion reaches a steady state, these processes follow Fick's first law of diffusion.

For the internal standard:

$$J_I \equiv \frac{1}{A}\frac{dn_I}{dt} = -D_{c,I}\frac{dC^{c,I}}{dx} = -D_{m,I}\frac{dC^{m,I}}{dx} = -D_{s,I}\frac{dC^{s,I}}{dx} \quad (18)$$

Where $J_I$ is the mass flux of the internal calibrant from the carrier(stripping) gas to the sample matrix; A is the surface area of the membrane; $dn_1$ is the amount of the internal calibrant that permeated from the carrier(stripping) gas during the time period dt; $D_{c,I}$, $D_{m,I}$, and $D_{s,I}$ are diffusion coefficients of the internal calibrant in the carrier(stripping) gas, membrane, and sample matrix, respectively, and $C^{c,I}$, $C^{m,I}$, and $C^{s,I}$ are concentrations of the internal calibrant in the carrier(stripping) gas, membrane, and sample matrix, respectively. A linear concentration gradient in the boundary layers and membrane is assumed:

$$J_I \equiv \frac{1}{A}\frac{dn_I}{dt} = -\frac{D_{C,I}}{\delta_{1,I}}(C_1 - C_0) \quad (19)$$

$$= -\frac{D_{m,I}}{\delta_{m,I}}(C_3 - C_2)$$

$$= -\frac{D_{s,I}}{\delta_{2,I}}(C_5, C_4)$$

Where $\delta_{1,I}$, $\delta_{m,I}$ and $\delta_{2,I}$ are the thickness of the inside boundary layer, the membrane, and the outside boundary layer, respectively; $C_0$ is the concentration of the internal calibrant in the bulk of the carrier(stripping) gas; $C_1$ is the concentration of the internal calibrant in the inside boundary layer at the interface of the membrane and the inside boundary layer; $C_2$ is the concentration of the internal calibrant in the membrane at the interface of the membrane and the inside boundary layer; $C_3$ is the concentration of internal calibrant in the membrane at the interface of the membrane and the outside boundary layer; $C_4$ is the concentration of the internal calibrant in the outside boundary layer at the interface of membrane and the outside boundary layer; and $C_5$ is the concentration of the internal calibrant in the bulk of the sample matrix. The mass transfer coefficients of the internal calibrant in the inside boundary layer $h_{c,I}$, membrane $h_{m,I}$, and outside boundary layer $h_{s,I}$ are defined as $$h_{c,I} = \frac{D_{c,I}}{\delta_{1,I}}, \; h_{m,I} = \frac{D_{m,I}}{\delta_{m,I}}, \text{ and } h_{s,I} = \frac{D_{s,I}}{\delta_{2,I}}.$$

Equation 19 can then be written in the forms:

$$J = -h_{c,I}(C_1 - C_0) \quad (20)$$

$$J = -h_{m,I}(C_3 - C_2) \quad (21)$$

$$J = -h_{s,I}(C_5 - C_4) \quad (22)$$

Assuming a quick partition equilibrium exists at the interfaces of membrane and the gas boundary layer:

$$K_I = \frac{C_2}{C_1} = \frac{C_3}{C_4} \quad (23)$$

Where $K_I$ is the distribution coefficient of the internal calibrant between the membrane and the gas phase.
Substitution of Equation 8 into Equation 6 yields:

$$J = -h_{m,I}K_I(C_4 - C_1) \quad (24)$$

Combining and rearranging Equations 5, 6, and 9 leads to:

$$J_I = \frac{1}{\left(\frac{1}{h_{c,I}} + \frac{1}{h_{s,I}} + \frac{1}{K_I h_{m,I}}\right)}(C_0 - C_5) = h_{total,I}(C_0 - C_5) \quad (25)$$

Where $h_{total,I}$ is the total mass transfer coefficient for the internal calibrant, and it is defined as $$\frac{1}{h_{total,I}} = \frac{1}{h_{c,I}} + \frac{1}{h_{s,I}} + \frac{1}{K_I h_{m,I}} \quad (26)$$

Using the same procedure, the flux equation for analyte in the sample matrix into the carrier(stripping) gas can be deduced as:

$$J_s = \frac{1}{\frac{1}{h_{c,s}} + \frac{1}{h_{s,s}} + \frac{1}{K_s h_{m,s}}}(C_a - C_f) = h_{total,s}(C_a - C_f) \quad (27)$$

Where $h_{c,s}$, $h_{m,s}$ and $h_{s,s}$, are the mass transfer coefficient of the target analyte in the inside boundary layer, membrane, and outside boundary layer, respectively. $K_s$ is the distribution constant of the target analyte between the membrane and the gas phase. $C_a$ is the concentration of target analyte in the bulk of the sample matrix; $C_f$ is the concentration of the target analyte in the bulk of the carrier(stripping) gas. $h_{total,s}$ is the total mass transfer coefficient for the target analyte and it is defined as $$\frac{1}{h_{total,s}} = \frac{1}{h_{c,s}} + \frac{1}{h_{s,s}} + \frac{1}{K_s h_{m,s}} \quad (28)$$

$h_{c,s}$, $h_{s,s}$, $h_{c,I}$ and $h_{s,I}$ are mass transfer parameters that reflect the effects of the boundary layer between the two sides of the membranes. As a simplified model, for the sample feed or the carrier(stripping) gas extraction side, gas can be regarded as a laminar flow past the flat plate and the following equation can be used to quantify the mass transfer through the boundary layer.

$$h = 0.626\frac{D}{L}\left(\frac{Lv^0}{\nu}\right)^{1/2}\left(\frac{\nu}{D}\right)^{1/3} \quad (29)$$

Where D is the diffusion coefficient of the analyte being transferred; L is the membrane effect length; $v^0$ is the bulk velocity of the sample or carrier (stripping) gas; and $\nu$ is the kinematic viscosity.

In most cases, $C_5$ and $C_f$ remained negligibly small during the experiment. This is because (1) the amounts of penetrant (internal calibrant or target analyte) were very small, (2) the carrier(stripping) gas continuously purged the inner surface of the membrane to prevent an increase in penetrant concentration near the inner surface of the membrane, and the penetrant of the calibrant was immediately released to the surrounding sample matrix, minimizing the possibility of accumulation on the outer surface of the membrane.

Thus, Equations 25 and 27 can be simplified as:

$$J_I = \frac{1}{A}\frac{n_I}{t} = h_{total,I}C_0 \quad (30)$$

-continued $$J_s = \frac{1}{A}\frac{n_s}{t} = h_{total,s}C_a \quad (31)$$

If r is defined as $$r = \frac{h_{total,s}}{h_{total,I}} \quad (32)$$

and Equation 31 is divided by Equation 15, the target analyte concentration can be expressed as $$C_a = \frac{n_s}{n_I r}C_0 = \frac{f_s H_s}{f_I H_I r}C_0 \quad (33)$$

In Equation 33, $C_0$ is the known concentration of the internal standard in the carrier (stripping) gas; r can be calibrated based on different scenarios, which is addressed below. $n_s$ is the extracted amount of the target analyte in the microtrap. $n_I$ is the permeated amount of internal calibrant in the matrix which is a difference between the accumulation of internal calibrant with and without membrane module. During calibration in the lab, the amount of penetrated internal calibrant can be conveniently measured using the SPME-GC system discussed as below. Both $f_s$ and $f_I$ are GC calibration factors for the target analyte and internal calibrant, respectively, and $H_s$ and $H_I$ are the peak areas of the target analyte and the internal calibrant, obtained individually by GC analysis.

Experimental details: MESI-portable GC with Internal Calibrant System. A general scheme of the MESI-portable GC internal calibrant system has been designed. The main components of this system include the membrane module, the microtrap (sorbent interface), the control unit of the cooler and heater, the gas chromatograph, and a silanized Pyrex glass cylinder with a permeation tube for the production of a stable flow of chemical vapour as the internal calibrant. The design of the membrane module, microtrap, and control unit of the cooler and heater have been presented in previous work. The PDMS membrane was mounted inside the module and the effective membrane surface area was 3.63 cm². Microtraps for this study were made from a small diameter Silicosteel® coated tubing (5 cm×0.75 mm i.d.) packed with PDMS material. The control unit kept the microtrap at −5° C. during preconcentration and heated to 200° C. during injection procedure. A Model 08610 SRI portable gas chromatograph (SRI Instruments, Torrance, Calif., USA) was, equipped with a FID detector and a MXT-Volatiles column (10 m×0.53 mm i.d., with 3.0 µm phenylmethylpolysiloxane film) (Restek Corp., Bellefonte, Pa., USA). The detector temperature was maintained at 250° C. The initial column temperature was set at 80° C., held for 10 minutes, and then increased at a rate of 20° C./min to 180° C. Nitrogen was used as the carrier (stripping) gas at a flow rate of 10.0 ml/min. The internal calibrant (o-xylene)-$N_2$ mixture gas was generated by the permeation method.[17] The Pyrex glass cylinder was wrapped with the heating tape and a home-built temperature controller was used to maintain the temperature at 35° C. The flow rate of the carrier (stripping) gas, which also served as a dilute gas to generate the internal calibrant, was controlled by the EPC unit in the SRI GC. Thus, the concentration of the internal calibrant can be calculated by the usual permeation method.

SPME-GC System for Studying Mass Transfer through a Membrane. In this study, a was designed specifically to facilitate the analysis of the mass transfer behaviours of the internal calibrant and the target analyte through a membrane. In this system, the membrane module was covered with a cell base for sample introduction (specific details are presented in a previous paper).[18] During the experiment, the expected gas flow rates of the sample stream and carrier (stripping) gas were controlled by two EPC control units in the portable model 8610C GC. The silicosteel tube (0.75 mm id) was used to connect the individual units of the system. The sample gas (at a constant concentration) was obtained by purging nitrogen through a silanized Pyrex glass cylinder ($\phi$=3 cm, 13 cm length), within which the permeation tube was kept filled with the target analytes. This cylinder was also wrapped with heating tape for temperature control. The exit of the stream was connected with a silanized Pyrex glass sampling vial ($\phi$=0.5 cm, 10 cm length with 2 cm branch tube). The vial was sealed with a Teflon lined half-hole-type Thermogreen LB-1 septa (Supelco, Bellefonte, Pa., USA) for SPME sampling and was located close to the membrane module. The actual concentration of the analyte-enriched stream, prior to entering the membrane module, could be measured in this sampling glass vial via SPME fibre sampling and then analyzed using GC under the conditions described below. A T-tee with a metering valve (Restek Corp., Bellefonte, Pa., USA) was installed in front of a SPME sampling vial to achieve the desired feed velocity. The outlet of the sample side of the membrane module was also connected to a silanized sampling vial, through which the permeate of the internal calibrant and the remaining sample were sampled by SPME and analyzed by GC. As constant concentration of the internal calibrant gas was produced by the same method used to generate the target analyte. The concentrations of internal calibrant, before and after the membrane module, and the target analyte permeate concentration were also measured by SPME through the sampling vial. The gas flowrates in both sides of membrane were set up the same value as that used in MESI-portable GC internal calibrant system and monitored using a calibrated gas flowmeter (Brooks Instrument Division, Emerson Electric Canada, ON, Canada).

GC analyses with SPME were performed using a Varian (Varian Associate, Sunnyvale, Calif.) GC 3400 CX gas chromatograph equipped with a RTX-5 capillary column (30 m×0.25 mm i.d.×1.0 µm)(Restek Corp., Bellefonte, Pa., USA), a septum-equipped programmable injector (SPI) with SPME inset and a flame ionization detector (FID). The carrier gas (nitrogen) headpressure was set at 25 psig (~172 kPa). The initial column temperature was set at 50° C., held for 1.0 min, and then increased at a rate of 20° C. min⁻¹ to 180° C. The temperatures of the injection port and detector were set at 250° C. and 300° C., respectively.

The total mass transfer coefficients of the internal calibrant and the target analyte can be calculated individually based on the following equation:

$$h_{total} = \frac{QH_{permeant}}{A(H_{feed} - H_{permeant})} \quad (34)$$

Where Q is the gas flow rate in the permeate side, A is the surface area of the membrane, $H_{permeant}$ and $H_{feed}$ are peak areas for the target analyte or internal calibrant between the two sides of the membrane. Using suitable permeate and feed velocities, the permeability (P) of the internal calibrant or target analyte can also be measured according to the following equation:

$$P = \frac{\delta_m H_{permeant}}{AQ(H_{feed} - H_{permeant})} \tag{35}$$

Where $\delta_m$ is the thickness of the membrane.

Materials and Procedures. PDMS membrane (dimethylsilicone membrane, SSP-M100C 0.001, 25 µm thickness) was obtained from Specialty Silicone Products Inc. (Ballston Spa, N.Y., USA). All chemicals were of analytical grade. Benzene, toluene, ethylbenzene, o-xylene and p-xylene were purchased from Sigma-Aldrich (Mississauga, ON, Canada). The SPME holders and 100 µm polydimethylsiloxane (PDMS) fibres were obtained from Supelco (Oakville, ON, Canada). The fibres were conditioned at 250° C. for 1 hr prior to use.

During the experiments to examine the effect of gas flow rate on the total mass transfer coefficient, analytes with different feed velocities were obtained by adjusting the metering valve (attached to the T-tee) prior to entrance into the sampling vial, which was located immediately upstream of the membrane module. The concentrations were verified by SPME analysis prior to experimental trials were initiated. To study the effect of the membrane temperature on the extraction efficiency, an Omegalux™ heating tape (Omega, Stamford, Conn., USA) was used to wrap the membrane module. A thermocouple sensor wire was placed in one hole near the membrane and sealed with asbestos. Both the heating tape and the thermocouple sensor were connected to an electronic heat control device designed and constructed by the Electronics Science Shop at the University of Waterloo. To simplify this experiment, the boundary layers between inside and outside membrane were reduced to be neglected level by using high flowrate (15 cm/s). o-Xylene and p-xylene was used as the internal calibrant and the sample, respectively.

The determination of the FID response factor was performed by injecting a standard mixture (in methanol) into the same instrument for analysis. For the measurement, the GC conditions, including the carrier gas flow rate, the oven temperature, and the detector temperatures, were maintained constant to the portable GC-MESI internal calibrant analysis conditions.

Figure 33:
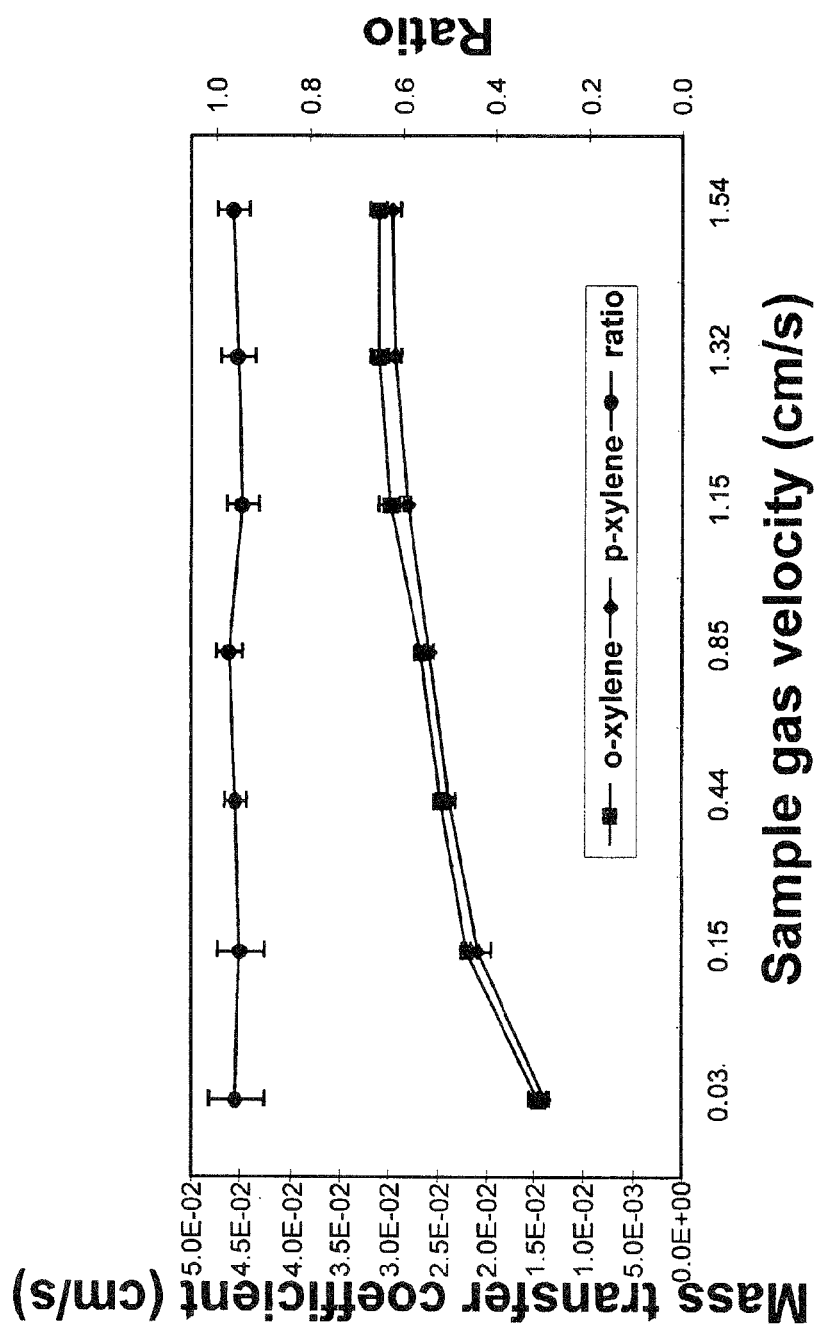
FIG. 33 shows the impact of flow rate of the sample on mass transfer coefficient of p-xylene (component). and o-xylene (calibrant) and mass transfer coefficient ratio between p-xylene and o-xylene.

Discussion: FIG. 33 presents the total mass transfer coefficients of o-xylene and p-xylene and the ratios (r) of the mass transfer coefficients of p-xylene to that of o-xylene. As expected, when the feed velocity of the sample increased, the total mass transfer coefficients of the internal calibrant and the sample increased simultaneously until a plateau was reached. This illustrated that changing the total mass transfer coefficients of the internal calibrant could reflect the aerodynamic variation of the outside membrane. The observed ratio was 0.954±0.009, and likely did not equal one due to the slight differences of the physicochemical properties of p-xylene and o-xylene.

Effect of Membrane Module Temperatures on the Mass Transfer Coefficient: During on-site (or field) analyses, sometimes the environmental temperature cannot be maintained constant and can change from day to day and from place to place. Thus, the temperature of the membrane module that lacks a thermostatic device will vary with temperature of its surroundings. Membrane extraction efficiency is a function of temperature. For the correct estimation of chemical concentrations from the field MESI and for the development of a suitable calibration method, it is necessary to sufficiently characterize the potential effects of temperature on the mass transfer through the membrane.

Figure 34:
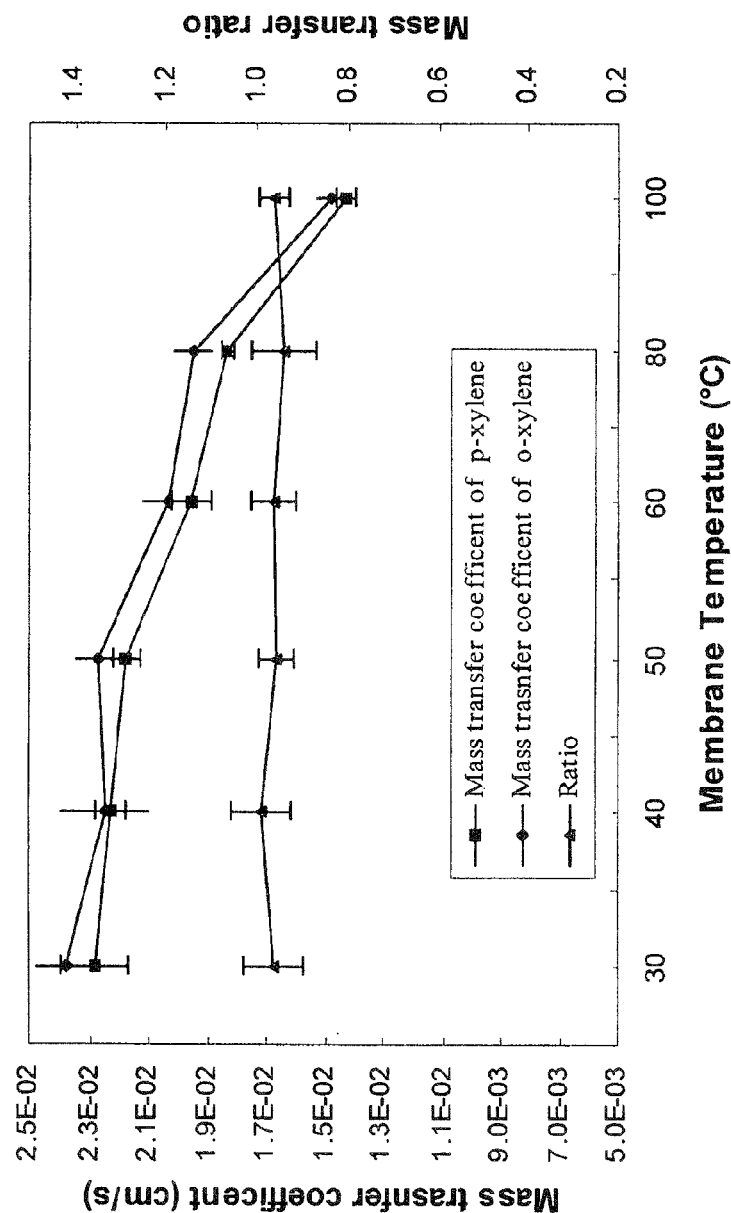
FIG. 34 shows the impact of temperature of the sample on mass transfer coefficient of p-xylene (component). and o-xylene (calibrant) and mass transfer coefficient ratio between p-xylene and o-xylene.

Temperature can change the mass transfer rate by influencing the distribution constant, the diffusion coefficient, and the boundary layer between the membrane and gas. For example, a polyethylene membrane exhibited a permeability increase of about 100% for a 10° C. increase in temperature. PDMS is far superior but still exhibits a decrease in permeability as the temperature increases. As FIG. 34 illustrates, when the temperature of the membrane module was changed from 30 to 100° C., the mass transfer coefficients of p-xylene and o-xylene varied. Within ambient temperature ranges (30-50° C.), the observed changes were not as great. When the temperature continued to increase, the variations of mass transfer coefficients were no longer insignificant. As noted above, under good convection conditions the mass transfer coefficient through the membrane is determined by the permeability (P), and it is a temperature dependent function that obeys the Arrhenius relation:[21]

$$P = D \times K \tag{36}$$

$$= D_0 \times K_0 \times \left(-(E_d + \Delta H_s) \times \left(\frac{1}{RT} - \frac{1}{RT_0}\right)\right)$$

$$= P_0 e^{\left[-E_P\left(\frac{1}{RT} - \frac{1}{RT_0}\right)\right]}$$

Where $D_0$ and $K_0$ represent the diffusion constant and the distribution constant at some initial temperature, $T_0$. $E_d$ refers to the activation energy for a diffusion step and the $\Delta H_s$ are the difference in the solution heat between the membrane and the sample matrix. In general, $E_d$ is larger than zero, which means that the diffusion constant increases with temperature. Conversely, the $\Delta H_s$ are less than zero, which means that the distribution constant between the membrane and the sample matrix decreases with the temperature. The overall effect depends on the sum of the effects of K and D during a temperature change. Experimental results indicated that the temperature effect on an increase in the diffusion coefficient was a trade-off against a decrease in the distribution constant within the observed temperature ranges (30-50° C.). However, the increase of D could not offset the decrease of K when the temperature of the membrane module was raised beyond 50° C., and the mass transfer coefficient decreased. On the other hand, within the limits of experimental error, the ratio of the mass transfer coefficient of p-xylene to o-xylene was kept constant within the entire experimental temperature range. This is because o-xylene and p-xylene are isomers, and they have close values of $E_d$ and $\Delta H_s$, which exhibit similar trends due to a variation in temperature. This means that o-xylene, as an internal calibrant, can also be used to correct the fluctuation of the signal intensity due to a shift in the temperature of the membrane module.

FIGS. 33 and 34 demonstrated that effect of flow rates and temperature variation can be successfully corrected by introducing the calibrant in the striping phase and then using ratio between the mass transfer rates corresponding to the target component (p-xylene) and the calibrant (o-xylene). This indicate suitability of the calibrant in the stripping phase approach for on-site or in-vivo continuous monitoring.

Example 11

Hydrophilic Polypyrrole Coatings on Wires, Standards in the Extraction Phase, and Fabrication of Fiber-in-Hypodermic-Needle for Use in a Biological System An alternative method is described herein, encompassing the preparation of hydrophilic PPY coatings, new samplers based on fiber-in-hypodermic-needle and in-vivo calibration based on the standard on the fiber approach. Use of new metal fiber coating consisting of mixture of poly(ethylene glycol) and octadecylchlorosilane derivatised silica (PEG/C18) coatings is also presented. Methods used herein that are identical to those in Example 1 are not described.

Figure 35:
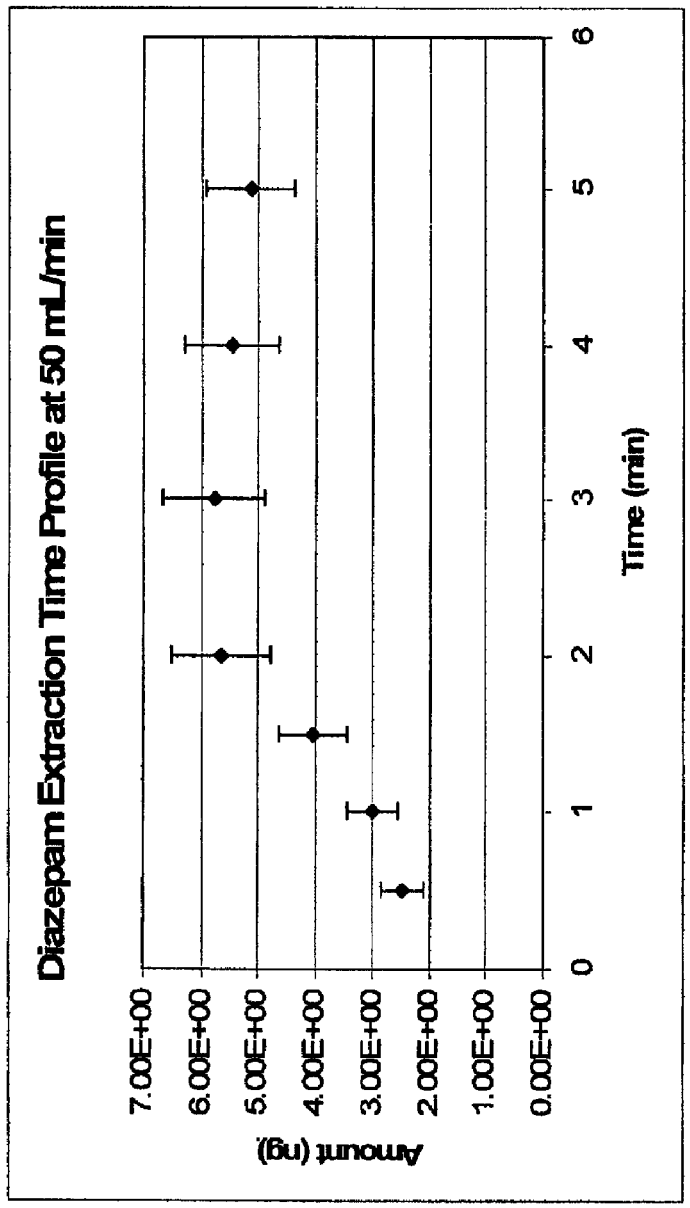
FIG. 35 illustrates Diazepam extraction at an intermediate to low flow rate of 50 mL/min.

PPY coating technology is the same as in Example 1, except for the addition of triethylene glycol to the coating solution. This modification results in the preparation of a more hydrophilic and porous PPY; whereas the equilibration time for PPY fibers described in Example 1 is 30 min, hydrophilic PPY fibers reach equilibrium in as little as 2 min, at a low blood flow rate FIG. 35 illustrates Diazepam extraction at an intermediate to low flow rate of 50 mL/min. Normal blood flow rate in the cephalic vein of the beagle dog can be as high as 300 mL/min. Accordingly, 2 min extraction time ensures that the coating reaches equilibrium.

The reduction of the sampling time to 2 min provides many advantages: convenience of sampling, possibility to monitor drugs with short in-vivo life time, and better correlation with conventional plasma analysis.

An in-vivo sampling device was built inside a stainless steel hypodermic needle (21G by 2 in, BD Canada). The 0.005" wire coated with polypyrrole was introduced in a suitable hypodermic tube for reinforcement, leaving the coated part outside. The hypodermic tube was then introduced inside the needle, sealed with silicone glue, and the upper part was formed into a handle. The new device build in medical-grade hypodermic needles offers sampling convenience, guaranteed biocompatibility, minimal exposure to blood, and ease of use in conjunction with the multiwell plate.

Figure 36:
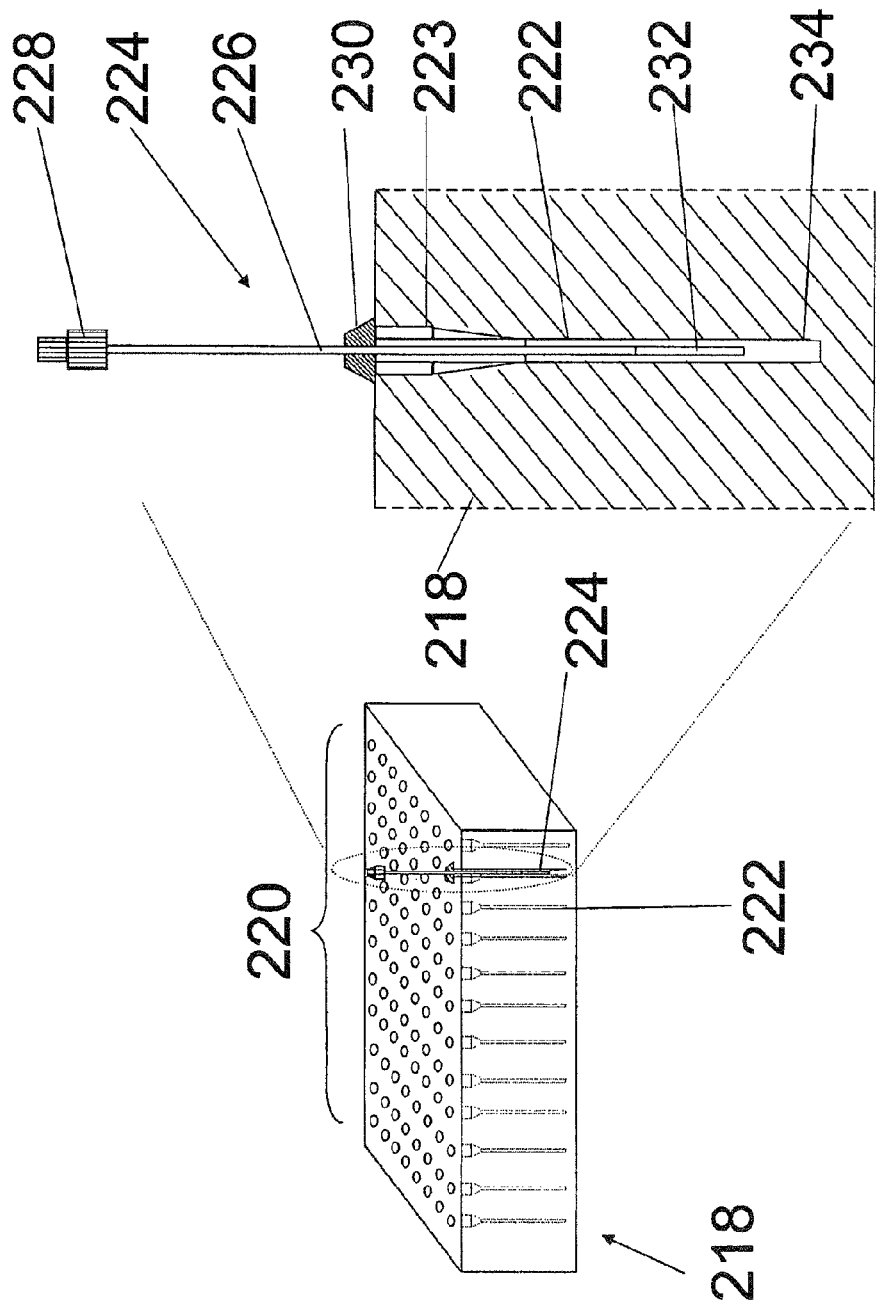
FIG. 36 shows a multiwell plate for performing parallel SPME fibre assemblies sealing operations.

In particular, FIG. 36 illustrates how the fiber assemblies 224 consisting of the fiber contained in the needle are transported in multiwell plate 218 to the sampling site in the sealed position to prevent contamination of sterile fibers and to prevent loss of calibrant if present in the coating. FIG. 36 shows multiwell plate 218 having multiplicity of wells 220, each of the wells having the narrow part 222, which is able to seal needle 234 of the SPME fiber assembly 224. Each of the wells also possesses tapered guiding neck 223 in the upper portion of the well. The SPME module contains fiber 226 containing the coating 232 in the lower portion of the fiber located in the needle. The upper end of the fiber contains the attachment module 228, which can be used to operate the fiber assembly. The SPME fiber assembly also contains sealing septa 230, which seals the upper portion of the needle. As FIG. 36 indicates when the SPME fiber assemblies are placed inside wells of the multiwell plate, the coated part of the fibers are completely sealed in the needle and surrounded well. The sealing plate can be used after fiber has been exposed to investigated systems to prevent loss of analytes or calibrant from the extraction phase. The plate can be placed in the robot to facilitate automated introduction of the fibers to the analytical instrument to prepare them for parallel desorption in multiwell plate.

Figure 37:
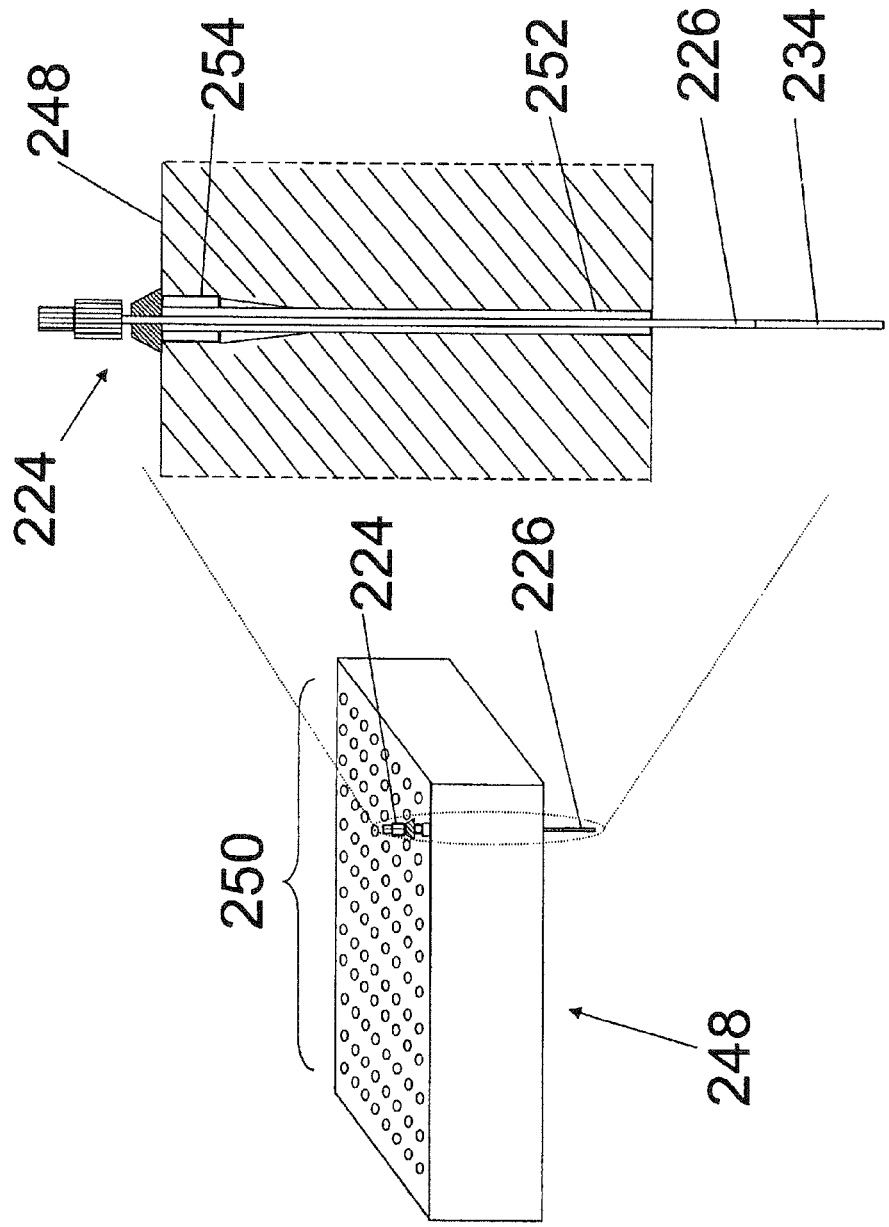
FIG. 37 shows a holding cover for a multiwell plate for SPME fibre assemblies.

After the experiment is completed the fiber assemblies can be alternatively placed in the holding cover 248 as FIG. 37 illustrates. FIG. 37 illustrates holding cover 248 for the multiwell plates having multiple openings 250 consisting of a guiding portion 254 in the upper part of the well and lower portion 252 to position SPME fiber assemblies correctly with respect to multiwells containing samples. FIG. 37 illustrates the fiber exposed from the needle ready for placement in the well.

Figure 38:
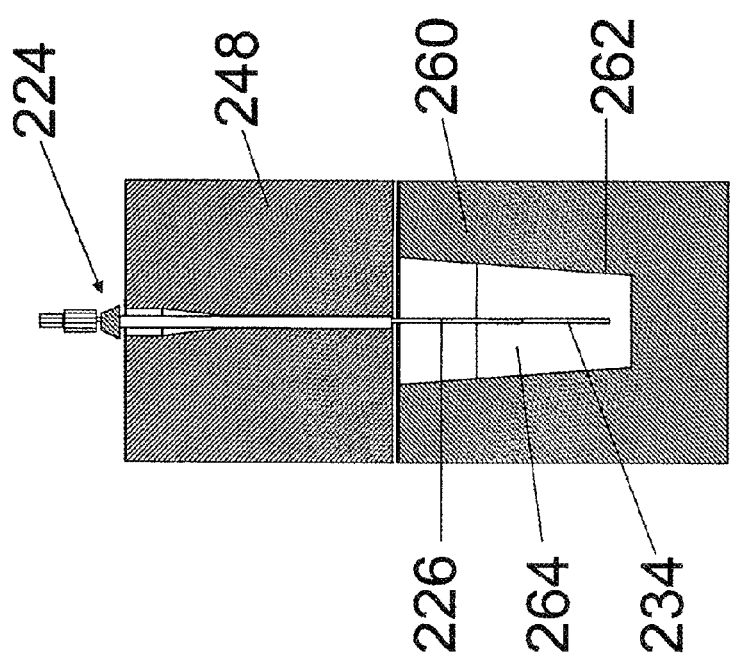
FIG. 38 shows an exposed fibre in a holding cover placed in a well of a multiwell plate.
Figure 39:
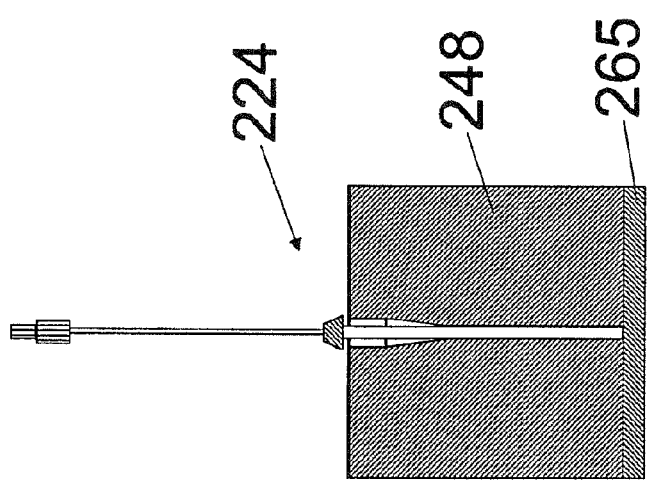
FIG. 39 shows a fibre in a holding cover retracted into a needle and sealed.

FIG. 38 shows the exposed fiber being placed in the well 262 of the multiwell plate 260 containing desorption solvent or a sample 264. After extraction the fibers containing analytes can be desorbed for determinations as FIG. 38 shows, or as FIG. 39 illustrates, the fiber 226 can be retracted into the needle located in the openings of the holding cover 248 and sealed by the sealing plate 265. In that arrangement the fibers are sealed in the holding plate. The sealing prevents loss of extracted components of interests, calibrant or contamination of the fiber. The fibers are then transported to laboratory for determination in this state. In the laboratory the sealing plate 265 is removed and placed on top of the multiwell plate 260 as FIG. 38 illustrates each well containing desorption solvent. The fibers are lowered to the desorption solvent simultaneously. The desorption can be accelerated by agitating the holding cover/multiwell plate system using for example the orbital shaker. Then the desorption solvent with desorbed components of interest is introduced to LC/MS instrumentation or optionally reconstituted to be more compatible with the mobile phase. Optionally the fibers could be desorbed directly into analytical instrument.

Calibration in the in-vivo experiment was done by using two procedures: (1) a comparison with results from an external calibration in whole blood similar to that shown in FIG. 12; and (2) a standard in the fiber approach. For the second approach, the fibers (PPY and PEG/C18) were pre-loaded with labeled diazepam (diazepam-D5, Cerilliant, Austin Tex.) by extraction from a solution with 50 ng/mL diazepam-D5 in PBS. On average, PPY fibers were preloaded with 129 ng and PEG/C18 fibers with 770 ng diazepam-D5.

The fibers pre-loaded with standard were exposed to the blood flow in-vein for 0.5 min in the case of PPY and 1 min in the case of PEG/C18 fibers. Even though the equilibration time is a little longer for PEG/C18, these fibers offer a 5-fold increase in sensitivity because of higher capacity of the coating.

Figure 40:
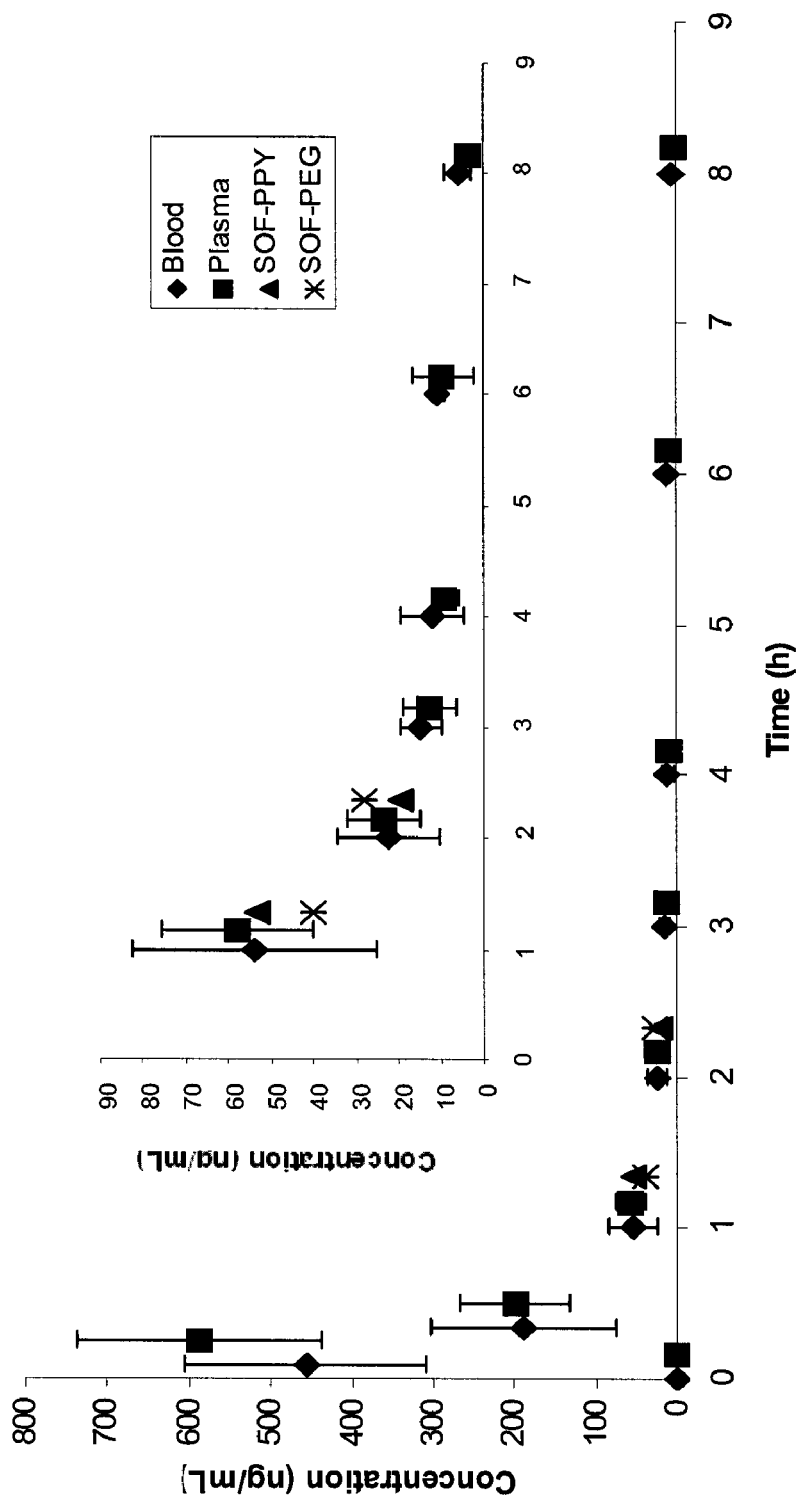
FIG. 40 illustrates a pharmacokinetic profile for Diazepam.
Figure 41:
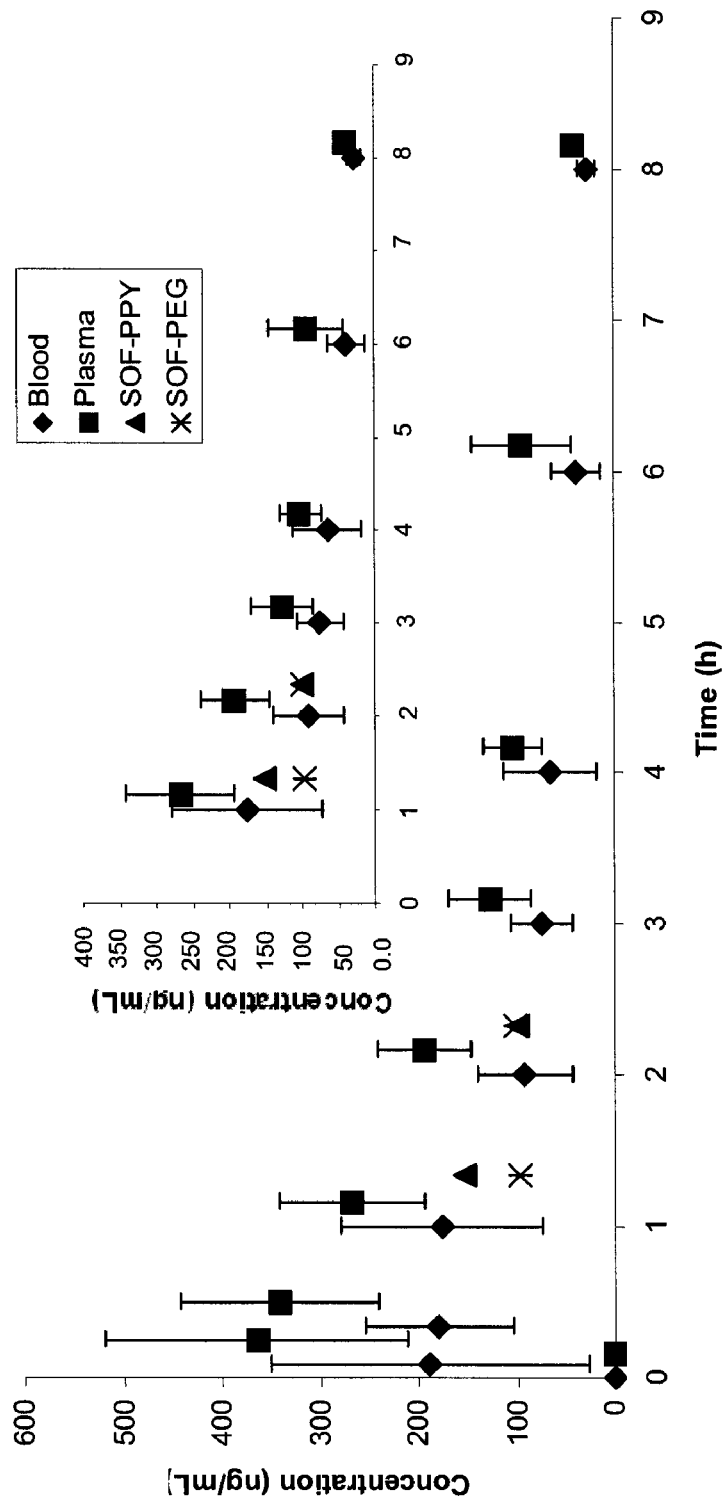
FIG. 41 illustrates a pharmacokinetic profile for Nordiazepam.
Figure 42:
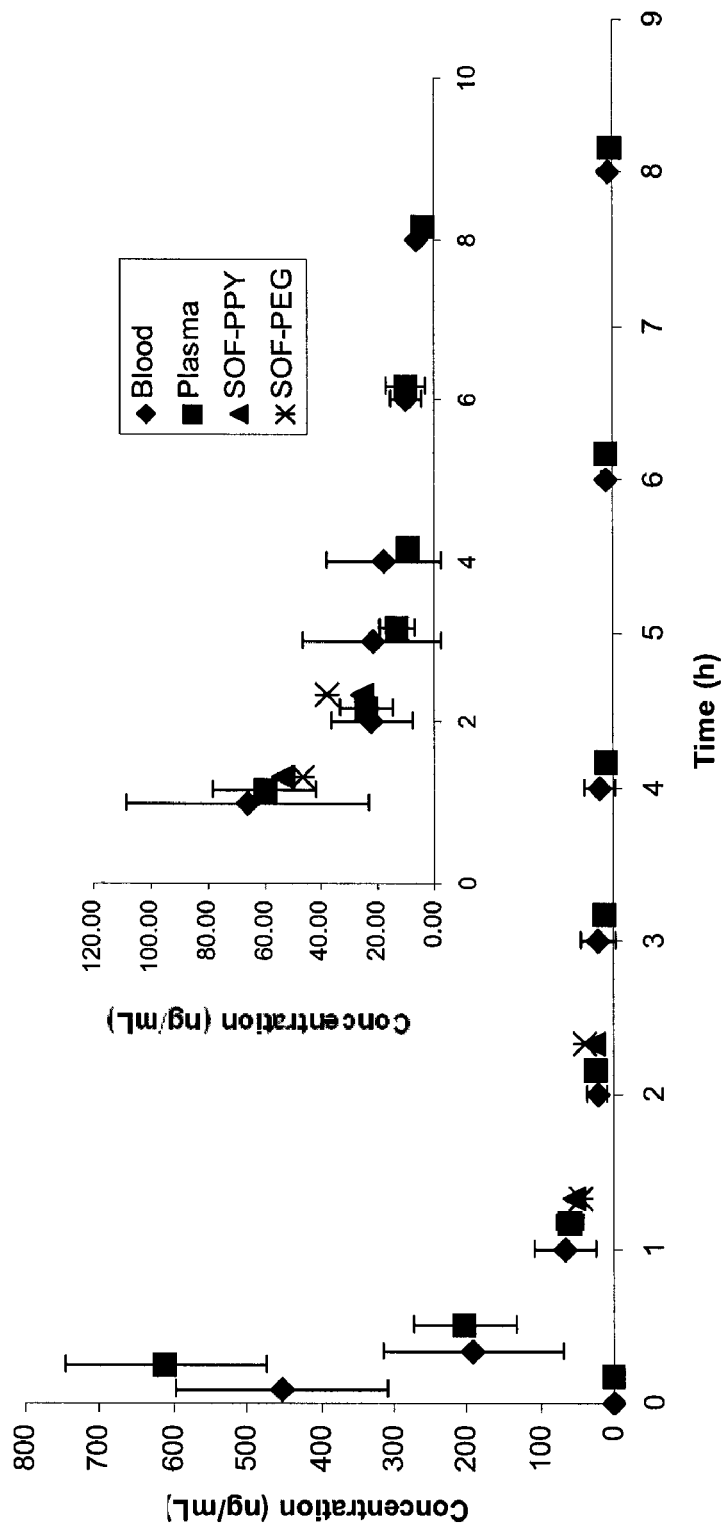
FIG. 42 illustrates a pharmacokinetic profile for Oxazepam.

FIG. 40, FIG. 41 and FIG. 42 show the results of the use of the fiber-in-hypodermic needle device for the catheter sampling method described above, for a pharmacokinetic study in dogs. In this case dogs were dosed with 0.5 mg diazepam per kg at time 0:00. Multiple samplings were performed from a catheter over an interval of 8 hours. Besides the results obtained with external calibration and standard on the fiber calibration, also shown is a comparison to results obtained by multiple blood draws over the same time period, with conventional sample preparation and analysis.

FIG. 40 illustrates a pharmacokinetic profile for Diazepam based on an average of 9 experiments (3 times on 3 dogs). FIG. 41 illustrates a pharmacokinetic profile for Nordiazepam based on an average of 9 experiments (3 times on 3 dogs). FIG. 42 illustrates a pharmacokinetic profile for Oxazepam based on an average of 9 experiments (3 times on 3 dogs).

These results demonstrate that the device is useful for the application described and that the method described produces results in good agreement with devices and methods using more invasive prior art sampling techniques. PEG/C18 phase showed similar biocompatibility during the experiment compared to PPY coating. The calibrant in the fiber approach was investigated for both PPY and PEG/C18 coating for quantification of concentration of components of interests (Diazapam, Oxazapam and Nordiazapam). The internal standard calibration with calibrant (Diazapan D5) in the fiber coating gave results similar to that obtained by using external calibration in blood matrix within the RSD of the measurement for these time points.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A liquid phase microextraction device for extracting components contained in a sample said device comprising a flowable liquid extraction phase and an inert calibrant in said liquid extraction phase, said liquid extraction phase contained in a sheath.

2. The device as claimed in claim 1 wherein said sheath is a needle.

3. The device as claimed in claim 1 wherein said sheath is a porous hollow fiber membrane.

\* \* \* \* \*